(12) United States Patent
Lyden et al.

(10) Patent No.: US 9,816,998 B2
(45) Date of Patent: Nov. 14, 2017

(54) CIRCULATING EXOSOMES AS DIAGNOSTIC/PROGNOSTIC INDICATORS AND THERAPEUTIC TARGETS OF MELANOMA AND OTHER CANCERS

(75) Inventors: David C. Lyden, New York, NY (US); Hector Peinado Selgas, New York, NY (US)

(73) Assignee: Cornell University, Ithaca, NY (US)

( * ) Notice: Subject to any disclaimer, the term of this patent is extended or adjusted under 35 U.S.C. 154(b) by 88 days.

(21) Appl. No.: 14/009,311

(22) PCT Filed: Apr. 2, 2012

(86) PCT No.: PCT/US2012/031879
§ 371 (c)(1),
(2), (4) Date: Oct. 23, 2013

(87) PCT Pub. No.: WO2012/135844
PCT Pub. Date: Oct. 4, 2012

(65) Prior Publication Data
US 2014/0038901 A1 Feb. 6, 2014

Related U.S. Application Data

(60) Provisional application No. 61/590,174, filed on Jan. 24, 2012, provisional application No. 61/470,936, filed on Apr. 1, 2011.

(51) Int. Cl.
*G01N 33/68* (2006.01)
*C12Q 1/68* (2006.01)

(52) U.S. Cl.
CPC ....... *G01N 33/6893* (2013.01); *C12Q 1/6886* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,685,911 B1 | 2/2004 | Zitvogel et al. | |
| 7,598,043 B2 | 10/2009 | Lyden et al. | |
| 8,465,738 B2 | 6/2013 | Lyden et al. | |
| 2008/0286825 A1* | 11/2008 | Bottaro et al. | 435/29 |
| 2009/0148460 A1 | 6/2009 | Delcayre et al. | |
| 2009/0220944 A1 | 9/2009 | Fais et al. | |
| 2010/0203529 A1* | 8/2010 | Kuslich et al. | 435/6 |

FOREIGN PATENT DOCUMENTS

| | | |
|---|---|---|
| EP | 1417229 B1 | 6/2011 |
| WO | 2009100029 A1 | 8/2009 |

OTHER PUBLICATIONS

Jagadeeswaran et al. (Cancer Res, 66: 352-361, 2006).*
Clayton et al. (J. Immunol., 180: 7249-7258, 2008).*
Rabinowits et al. (Clinical Lung Cancer, 10: 42-46, 2009).*
Boccaccio et al. (Nature Reviews, Cancer, 6: 637-645, 2006).*
Bertolini et al. (Cancer Research, 63: 4342-4346, 2003).*
Peinado et al. (Nature Medicine, 18, 883-891, publication date: May 27, 2012).*
Helfrich et al. (Clin. Cancer Res., 15: 1384-1392, 2009).*
Kaplan et al., "VEGFR1-Positive Haematopoietic Bone Marrow Progenitors Initiate the Pre-Metastatic Niche," with Supplementary Materials, Nature 438(8):820-827 (2005).
Castellana et al., "Membrane Microvesicles as Actors in the Establishment of a Favorable Prostatic Tumoral Niche: A Role for Activated Fibroblasts and CX3CL1-CS3CR1 Axis," Cancer Research 69(3):785-793 (2009).
Christensen et al., "c-Met as a Target for Human Cancer and Characterization of Inhibitors for Therapeutic Intervention," Cancer Lett. 225:1-26 (2005).
Hood et al., "Exosomes Released by Melanoma Cells Prepare Sentinel Lymph Nodes for Tumor Metastasis," Cancer Research 71(11):3792-3801 (2011).
Hao et al., "Epigenetic Transfer of Metastatic Activity by Uptake of Highly Metastatic B16 Melanoma Cell-Released Exosomes," Exp. Oncol. 28(2):126-131 (2006).
Jung et al., "CD44v6 Dependence of Premetastatic Niche Preparation by Exosomes," NeoPlasia 11(10):1093-1105 (2009).
Lima et al., "Tumor-Derived Microvesicles Modulate the Establishment of Metastatic Melanoma in a Phosphatidylserine-Dependent Manner," Cancer Lett. 283:168-175 (2009).
Ostrowski et al., "Rab27a and Rab27b Control Different Steps of the Exosome Secretion Pathway," Nature Cell Biology 12(1):19-30 (2009) abstract only.
Peinado et al., "The Secreted Factors responsible for Pre-Metastatic Niche Formation: Old Sayings and New Thoughts," Seminars in Cancer Biology 21(2):139-146(2011).
Wang et al., "Enhanced Expression of Rab27A Gene by Breast Cancer Cells Promoting Invasiveness and the Metastasis Potential by Secretion of Insulin-Like Growth Factor-II," Mol. Cancer Research 6(3):372-382 (2008).
Whiteside et al., "Tumour-Derived Exosomes or Microvesicles: Another Mechanism of Tumour Escape From the Host Immune System?," British Journal of Cancer 92:209-211 (2005).
Wu et al., "Anti-Angiogenic Therapeutic Drugs for Treatment of Human Cancer," J. Cancer Mol. 4(2):37-45 (2008).
Wysoczynski et al., "Lung Cancer Secreted Microvesciles: Underappreciated Modulators of Microenvironment in Expanding Tumors," Int J. Cancer 125(7):1595-1603 (2009).
Lagozzi et al., "High Levels of Exosomes Expressing CD63 and Caveolin-1 in plasma of Melanoma Patients," PLoS One 4:e5219 (2009).
Skog et al., "Glioblastoma Microvesicles Transport RNA and Proteins That Promote Tumour Growth and Provide Diagnostic Biomarkers," Nat. Cell Biol. 10:1470-1476 (2008).

(Continued)

*Primary Examiner* — Brad Duffy
*Assistant Examiner* — Nelson B Moseley, II
(74) *Attorney, Agent, or Firm* — LeClairRyan, a Professional Corporation

(57) ABSTRACT

The present invention is directed to methods of diagnosing, preventing, and treating metastatic disease in a subject. The present invention is also directed to a method of inhibiting primary tumor growth in a subject. Methods of identifying candidate compounds useful for preventing and treating metastatic disease and primary tumor growth in a subject are also disclosed.

11 Claims, 41 Drawing Sheets
(24 of 41 Drawing Sheet(s) Filed in Color)

(56) References Cited

OTHER PUBLICATIONS

Baj-Krzyworzeka et al., "Tumour-Derived Microvesicles Carry Several Surface Determinants and mRNA of Tumour Cells and Transfer Some of These Determinants to Monocytes," Cancer Immunol. Immunother. 55:808-818 (2006) abstract only.

Liu et al., "Contribution of MyD88 to the Tumor Exosome-Mediated Induction of Myeloid Derived Suppressor Cells," Am. J. Pathol. 176(5):2490-2499 (2010).

Xiang et al., "Induction of Myeloid-Derived Suppressor Cells by Tumor Exosomes," Int. J. Cancer 124(11):2621-2633 (2009).

Ratajczak et al., "Embryonic Stem Cell-Derived Microvesicles Reprogram Hematopoietic Progenitors: Evidence for Horizontal Transfer of mRNA and Protein Delivery," Leukemia 20:847-856 (2006).

Wada et al., "Surface-Bound TGF-Beta1 on Effusion-Derived Exosomes Participates in Maintenance of Number and Suppressive function of Regulatory T-Cells in Malignant Effusions," AntiCancer Research 30:3747-3758 (2010).

International Search Report and Written Opinion for PCT/US2012/031879, filed Apr. 2, 2012 (dated Sep. 25, 2012).

* cited by examiner

Figure 5A

| | Rab27a | Rab5b | Rab7 | Rab1a | Rab27b | Rab5a |
|---|---|---|---|---|---|---|
| SK-Mel-161 | | | | | | |
| SK-Mel-28 | | | | ++ | | |
| SK-Mel-202 | | | | ++ | | |
| SK-Mel-265 | | | | ++ | | |
| SK-Mel-23 | | | | | | |
| SK-Mel-264 | | | | ++ | | |
| SK-Mel-35 | | | | ++ | | |
| SK-Mel-202 | | ++ | | ++ | | |
| SK-Mel-197.2 | | ++ | ++ | ++ | | |
| SK-Mel-90 | | ++ | ++ | ++ | ++ | |
| SK-Mel-246 | | ++ | ++ | ++ | | |
| SK-Mel-230 | | ++ | ++ | ++ | | |
| SK-Mel-192 | | | | ++ | | |
| SK-Mel-267 | | | | ++ | | |
| SK-Mel-73 | ++ | ++ | ++ | ++ | | |
| SK-Mel-271 | ++ | ++ | ++ | ++ | | |
| SK-Mel-256 | ++ | ++ | ++ | ++ | | |
| SK-Mel-17 | ++ | ++ | ++ | ++ | | |
| SK-Mel-39 | ++ | ++ | ++ | ++ | | |
| SK-Mel-146 | ++ | ++ | ++ | ++ | ++ | |
| SK-Mel-176 | ++ | ++ | ++ | ++ | | |
| SK-Mel-103 | | ++ | ++ | ++ | | ++ |
| SK-Mel-12 | ++ | ++ | ++ | ++ | | |
| SK-Mel-155 | ++ | | | | ++ | ++ |
| SK-Mel-229 | ++ | | | | | ++ |
| SK-Mel-266 | | ++ | ++ | ++ | ++ | ++ |
| SK-Mel-199 | | ++ | | ++ | ++ | ++ |
| SK-Mel-7 | ++ | ++ | ++ | ++ | | |
| SK-Mel-228 | ++ | ++ | ++ | ++ | | |
| SK-Mel-191 | | ++ | ++ | ++ | | ++ |
| SK-Mel-110 | | ++ | ++ | ++ | | |
| SK-Mel-249 | | ++ | ++ | ++ | | |
| SK-Mel-131 | | ++ | ++ | ++ | | |
| SK-Mel-37 | | ++ | ++ | ++ | | |
| SK-Mel-75 | | ++ | ++ | ++ | | |
| SK-Mel-147 | | ++ | ++ | ++ | | |
| SK-Mel-24 | | ++ | ++ | ++ | | |
| SK-Mel-225 | | ++ | ++ | ++ | | |
| SK-Mel-170 | | ++ | ++ | ++ | | |
| AsPc1 | | ++ | ++ | ++ | ++ | |
| MCF7 | | ++ | ++ | ++ | ++ | |
| MDA231 | | ++ | ++ | ++ | ++ | |
| SkBr3 | | ++ | ++ | ++ | ++ | |

| Gene | Fold 24h | Fold 48h | Function | Description |
|---|---|---|---|---|
| Apc | | 1.29 | Tumor supressor | Adenomatosis polyposis coli |
| Atp6v0a2 | | | Vesicular traffic | ATPase, H+ transporting, lysosomal V0 subunit A2 |
| Atrx | | 1.45 | Transcription | Alpha thalassemia/mental retardation syndrome X-linked homolog (human) |
| Ccnc | | 1.48 | Cell Cycle | Cyclin C |
| Ccnd2 | | | Cell Cycle | Cyclin D2 |
| Cdkn1a | | | Cell Cycle | Cyclin-dependent kinase inhibitor 1A (P21) |
| Cdkn1b | | 1.69 | Cell Cycle | Cyclin-dependent kinase inhibitor 1B |
| Chd7 | | 0.57 | Transcription | Chromodomain helicase DNA binding protein 7 |
| Clec4d | | | Vesicular traffic | C-type lectin domain family 4, member d |
| Cyp1a1 | | 1.23 | Vesicular traffic | Cytochrome P450, family 1, subfamily a, polypeptide 1 |
| Dusp18 | | 1.48 | Signal transduction | Dual specificity phosphatase 18 |
| Eif3c | | | Transcription | Eukaryotic translation initiation factor 3, subunit C |
| Eif4ebp2 | | | Transcription | Eukaryotic translation initiation factor 4E binding protein 2 |
| Eln | | 1.22 | ECM protein | Elastin |
| Endod1 | 0.58 | | Inflammation | Endonuclease domain containing 1 |
| Epha3 | | 1.41 | Membrane receptor | Eph receptor A3 |
| Gypa | | | Membrane receptor | Glycophorin A |
| Hlf | | 0.87 | Transcription | Hepatic leukemia factor |
| Hsp90ab1 | | 1.40 | Heat shock protein | Heat shock protein 90kDa alpha (cytosolic), class B member 1 |
| Hspa1a | | 1.76 | Heat shock protein | Heat shock protein 1A |
| Hspa1b | | | Heat shock protein | Heat shock protein 1B |
| Hspg2 | | 0.95 | ECM protein | Perlecan (heparan sulfate proteoglycan 2) |
| Id4 | | | Transcription | Inhibitor of DNA binding 4 |
| Igh | | | Membrane receptor | Immunoglobulin heavy chain complex |
| Igh-6 | | | Immune response | Immunoglobulin heavy chain 6 (heavy chain of IgM) |
| Igkv14-111 | | | Membrane receptor | Immunoglobulin kappa chain variable 14-111 |
| Isoc1 | | | ECM protein | Isochorismatase domain containing 1 |
| Itsn2 | | | Vesicular traffic | Intersectin 2 |
| Marcks | 0.90 | | Cytoskeleton rearragement | Myristoylated alanine rich protein kinase C substrate |
| Marco | | 0.58 | Immune response | Macrophage receptor with collagenous structure |
| Mettl7a | | 0.98 | Transcription | Methyltransferase like 7A |
| Mmp9 | | | ECM protein | Matrix metallopeptidase 9 |
| Mpo | | 0.54 | Immune response | Myeloperoxidase |
| Myh11 | | 0.74 | Cytoskeleton rearragement | Myosin, heavy polypeptide 11, smooth muscle |
| Nfatc3 | | 1.51 | Transcription | Nuclear factor of activated T-cells, cytoplasmic, calcineurin-dependent 3 |
| Npnt | | | Cell adhesion | Nephronectin |
| Nr2c2 | | | Transcription | Nuclear receptor subfamily 2, group C, member 2 |
| Nr4a1 | | | Transcription | Nuclear receptor subfamily 4, group A, member 1 |
| Nrip1 | | | Transcription | Nuclear receptor interacting protein 1 |
| Pi4k2b | | 0.50 | Vesicular traffic | Phosphatidylinositol 4-kinase type 2 beta |
| Polr3f | | | Transcription | Polymerase (RNA) III (DNA directed) polypeptide F |
| Psg28 | | | Signal transduction | Pregnancy-specific glycoprotein 28 |
| Pten | | | Tumor supressor | Phosphatase and tensin homolog |

Figure 16

CIRCULATING EXOSOMES AS DIAGNOSTIC/PROGNOSTIC INDICATORS AND THERAPEUTIC TARGETS OF MELANOMA AND OTHER CANCERS

This application is a national stage application under 35 U.S.C. §371 of PCT Application No. PCT/US2012/031879, filed Apr. 2, 2012, which claims the benefit of U.S. Provisional Patent Application Ser. Nos. 61/470,936, filed Apr. 1, 2011, and 61/590,174, filed Jan. 24, 2012, which are hereby incorporated by reference in their entirety.

FIELD OF THE INVENTION

The present invention is directed to methods of diagnosing, preventing, and treating metastatic disease in a subject.

BACKGROUND OF THE INVENTION

Diffusible factors such as cytokines and growth factors, and insoluble factors such as extracellular matrix (ECM) molecules are thought to be the principle mediators of crosstalk between the cellular constituents of the tumor microenvironment (Joyce et al., "Microenvironmental Regulation of Metastasis," *Nat. Rev. Cancer* 9:239-52 (2009); Kenny et al., "Targeting the Tumor Microenvironment," *Front. Biosci.* 12:3468-74 (2007); and Peinado et al., "The Secreted Factors Responsible for Pre-Metastatic Niche Formation Old Sayings and New Thoughts," *Semin. Cancer Biol.* 21(2):139-146 (2011)). However, accumulating evidence suggests that the release of membrane vesicles also mediate communication between cells on both a local and systemic level (Peinado et al., "The Secreted Factors Responsible for Pre-Metastatic Niche Formation: Old Sayings and New Thoughts," *Semin. Cancer Biol.* 21(2):139-146 (2011); Iero et al. "Tumour-Released Exosomes and their Implications in Cancer Immunity," *Cell Death Differ.* 15:80-8 (2008); Ratajczak et al., "Membrane-Derived Microvesicles: Important and Underappreciated Mediators of Cell-To-Cell Communication," *Leukemia* 20:1487-95 (2006); Muralidharan-Chari et al., "Microvesicles: Mediators of Extracellular Communication During Cancer Progression," *J. Cell Sci.* 123:1603-11 (2010); Cocucci et al., "Shedding Microvesicles: Artefacts no More," *Trends Cell Biol.* 19:43-51 (2009); and van Niel et al., "Exosomes: A Common Pathway for a Specialized Function," *J. Biochem.* 140:13-21 (2006)).

Although, microvesicles and exosomes were initially thought to be products of a pathway used to release excess material from cells; they have been shown to mediate morphogen signaling, immunological signaling, cell recruitment, and horizontal transfer of genetic material (Ratajczak et al., "Membrane-Derived Microvesicles: Important and Underappreciated Mediators of Cell-To-Cell Communication," *Leukemia* 20:1487-95 (2006) and Valadi et al., "Exosome-Mediated Transfer of mRNAs and MicroRNAs is a Novel Mechanism of Genetic Exchange Between Cells," *Nat. Cell Biol.* 9:654-9 (2007)). Exosomes are small vesicles (30-100 nm) derived from the luminal membranes of late endosomes/multivesicular bodies (MVB), and are constitutively released via the fusion of MVBs with the cell membrane (Thery et al., "Exosomes: Composition, Biogenesis and Function," *Nat. Rev. Immunol.* 2:569-79 (2002) and Fevrier et al., "Exosomes: Endosomal-Derived Vesicles Shipping Extracellular Messages," *Curr. Opin. Cell Biol.* 16:415-21 (2004)). Exosomes secreted by tumor cells have been recently implicated in all stages of tumor progression (Peinado et al., "The Secreted Factors Responsible for Pre-Metastatic Niche Formation: Old Sayings and New Thoughts," *Semin. Cancer Biol.* 21(2):139-146 (2011); Iero et al. "Tumour-Released Exosomes and their Implications in Cancer Immunity," *Cell Death Differ.* 15:80-8 (2008); and van Niel et al., "Exosomes: A Common Pathway for a Specialized Function," *J. Biochem.* 140:13-21 (2006)). Studies have found that tumor exosomes are involved in the cell-cell communication, such as the horizontal transfer of information (i.e. mRNAs, microRNAs and proteins) between stem cells (Ratajczak et al., "Embryonic Stem Cell-Derived Microvesicles Reprogram Hematopoietic Progenitors: Evidence for Horizontal Transfer of mRNA and Protein Delivery," *Leukemia* 20:847-56 (2006) and Janowska-Wieczorek et al., "Platelet-Derived Microparticles Bind to Hematopoietic Stem/Progenitor Cells and Enhance their Engraftment," *Blood* 98:143-9 (2001)), endothelial cells (Al-Nedawi et al., "Endothelial Expression of Autocrine VEGF upon the Uptake of Tumor-Derived Microvesicles Containing Oncogenic EGFR," *Proc. Natl. Acad. Sci. U.S.A.* 106:3794-9 (2009) and Nazarenko et al., "Cell Surface Tetraspanin Tspan8 Contributes to Molecular Pathways of Exosome-Induced Endothelial Cell Activation," *Cancer Res.* 70:1668-78 (2010)), fibroblasts (Webber et al., "Cancer Exosomes Trigger Fibroblast to Myofibroblast Differentiation," *Cancer Res.* 70:9621-30 (2010)), bone marrow-derived cells (BMDCs) (Valadi et al., "Exosome-Mediated Transfer of mRNAs and MicroRNAs is a Novel Mechanism of Genetic Exchange Between Cells," *Nat. Cell Biol.* 9:654-9 (2007); Ratajczak et al., "Embryonic Stem Cell-Derived Microvesicles Reprogram Hematopoietic Progenitors Evidence for Horizontal Transfer of mRNA and Protein Delivery," *Leukemia* 20:847-56 (2006); Baj-Krzyworzeka et al., "Tumour-Derived Microvesicles Carry Several Surface Determinants and mRNA of Tumour Cells and Transfer some of these Determinants to Monocytes," *Cancer Immunol. Immunother.* 55:808-18 (2006); Liu et al., "Contribution of MyD88 to the Tumor Exosome-Mediated Induction of Myeloid Derived Suppressor Cells," *Am. J. Pathol.* 176:2490-9 (2010); Xiang et al., "Induction of Myeloid-Derived Suppressor Cells by Tumor Exosomes," *Int. J. Cancer* 124:2621-33 (2009); and Yu et al., "Tumor Exosomes Inhibit Differentiation of Bone Marrow Dendritic Cells," *J. Immunol.* 178:6867-75 (2007)), and tumor cells (Al-Nedawi et al., "Intercellular Transfer of the Oncogenic Receptor EGFRvIII by Microvesicles Derived from Tumour Cells," *Nat. Cell Biol.* 10:619-24 (2008); and Hao et al., "Epigenetic Transfer of Metastatic Activity by Uptake of Highly Metastatic B16 Melanoma Cell-Released Exosomes," *Exp. Oncol.* 28:126-31 (2006); and Skog et al., "Glioblastoma Microvesicles Transport RNA and Proteins that Promote Tumour Growth and Provide Diagnostic Biomarkers," *Nat. Cell Biol.* 10:1470-6 (2008)).

It is now well recognized that BMDCs play a crucial role in the generation of a suitable microenvironment for the primary tumor and the development of metastasis through a process called "pre-metastatic niche formation" (Joyce et al., "Microenvironmental Regulation of Metastasis," *Nat. Rev. Cancer* 9:239-52 (2009); Wels et al., "Migratory Neighbors and Distant Invaders: Tumor-Associated Niche Cells," *Genes Dev.* 22:559-74 (2008); Psaila et al., "The Metastatic Niche: Adapting the Foreign Soil," *Nat. Rev. Cancer* 9:285-93 (2009); Kaplan et al., "VEGFR1-Positive Haematopoietic Bone Marrow Progenitors Initiate the Pre-Metastatic Niche," *Nat.* 438:820-7 (2005); Guise, T., "Examining the Metastatic Niche: Targeting the Microenvironment," *Semin. Oncol.* 37 Suppl. 2:S2-14 (2010); and Gao et al., "Bone Marrow-Derived Endothelial Progenitor Cells Contribute to the Angiogenic Switch in Tumor Growth and Metastatic Progression," *Biochim. Biophys. Acta.* 1796:33-40 (2009)). Although secreted factors such as vascular endothelial growth factor-A (VEGF-A), placental growth factor (P/GF), transforming growth factor-beta (TGF-β), tumor necrosis alpha (TNF-α), and lysyl oxidase (LOX) are known contributors to BMDCs recruitment to both primary tumor and pre-metastatic niches (Kaplan et al., "VEGFR1-Positive Haematopoietic Bone Marrow Progenitors Initiate the Pre-Metastatic Niche," *Nat.* 438:820-7 (2005); Erler et al., "Hypoxia-Induced Lysyl Oxidase is a Critical Mediator of Bone Marrow Cell Recruitment to Form the Premetastatic Niche," *Cancer Cell.* 15:35-44 (2009); and Hiratsuka et al., "Tumour-Mediated Upregulation of Chemoattractants and Recruitment of Myeloid Cells Predetermines Lung Metastasis," *Nat. Cell. Biol.* 8:1369-75 (2006)), the potential contribution of exosomes to this process has yet to be evaluated.

The present invention is directed to overcoming these and other deficiencies in the art.

SUMMARY OF THE INVENTION

A first aspect of the present invention is directed to a method of inhibiting metastatic disease progression in a subject. This method involves selecting a subject having metastatic disease and administering, to the selected subject, an agent that inhibits primary cancer cell exosomes under conditions effective to inhibit metastatic disease progression in the subject.

Another aspect of the present invention is directed to a method of inhibiting pre-metastatic niche formation in a subject. This method involves selecting a subject at risk for metastatic disease and administering to the selected subject, an agent that inhibits primary cancer cell exosomes under conditions effective to inhibit pre-metastatic niche formation in the subject.

Another aspect of the present invention is directed to a method of inhibiting primary tumor growth in a subject. This method involves selecting a subject having a primary tumor and administering to the selected subject, an agent that inhibits primary tumor cell exosomes under conditions effective to inhibit primary tumor growth in the subject.

Another aspect of the present invention is directed to a method of determining the prognosis of a subject having cancer. This method involves obtaining a sample from the subject and measuring the exosome level in the sample. The method further involves comparing the measured exosome level in the sample to a reference exosome level and determining the subject's prognosis based on the comparing, where an increase in the measured exosome level in the sample compared to the reference exosome level indicates the subject has an unfavorable prognosis. The method further involves modifying the course of treatment for the subject where warranted by the determined prognosis.

Another aspect of the present invention is directed to a method of determining the prognosis of a subject having cancer. This method involves obtaining an exosomal sample from the subject and measuring the exosome expression level of one or more proteins selected from the group consisting MET, TYRP2, VLA-4, Hsp-90, and Hsp-70. The method further involves comparing the exosomal expression level of the one or more proteins in the sample to reference exosomal expression levels of the one or more corresponding proteins, and determining the subject's prognosis based on said comparison, where an increase in the measured exosomal protein expression level in the sample compared to the reference exosomal expression level indicates an unfavorable prognosis for the subject. The method further involves modifying the course of treatment for the subject where warranted by the determined prognosis.

Another aspect of the present invention is directed to a method of determining the prognosis of a subject having cancer. This method involves obtaining a blood sample from the subject and measuring the MET expression level in bone marrow derived progenitor cells. The method further involves comparing the MET expression level in the bone marrow derived progenitor cells from the sample to a reference MET expression level in bone marrow derived progenitor cells and determining the subject's prognosis based on said comparing, where an increase in the measured MET expression level in bone marrow derived progenitor cells in the sample compared to the reference MET expression level identifies an unfavorable prognosis for the subject. The method further involves modifying the course of treatment for the subject where warranted by the determined prognosis.

Another aspect of the present invention is directed to a method of diagnosing metastatic disease type in a subject. This method involves obtaining an exosomal sample from the subject and detecting one or more biomarkers of metastatic disease type in the sample. The method further involves identifying the metastatic disease type in the subject based on said detecting and administering a therapeutic agent to the subject that is suitable for treating the identified metastatic disease type.

Another aspect of the invention is directed to a method of monitoring metastatic disease treatment in a subject. This method involves obtaining first and second samples, at different points in time, from the subject being treated for a metastatic disease and measuring the exosome level and/or the exosomal expression levels of one or more protein biomarkers of metastatic disease in each sample. This method further involves comparing the exosome level and/or the exosomal expression levels of the one or more protein biomarkers of metastatic disease in the first sample to corresponding levels in the second sample, and determining whether the subject is responding to the metastatic disease treatment based on this comparison.

Another aspect of the present invention is directed to an in vitro method of identifying candidate compounds useful for inhibiting primary tumor growth or preventing the formation and progression of metastatic disease in a subject. This method involves providing a test compound and contacting the test compound with malignant cells that secrete high levels of exosomes. The method further involves identifying test compounds that inhibit exosome production, secretion, and/or activity, from the malignant cells as candidate compounds useful for inhibiting primary tumor growth or preventing the formation and progression of metastatic disease in a subject.

Another aspect of the invention is directed to an in vivo method of identifying candidate compounds useful for inhibiting primary tumor growth or preventing the formation and progression of metastatic disease in a subject. This method involves providing a test compound and providing an animal model with a primary tumor. The method further involves administering to the animal model malignant cell derived exosomes and the test compound, and identifying test compounds which inhibit exosome activity in the animal model as candidate compounds useful for inhibiting primary tumor growth or preventing the formation and progression of metastatic disease in a subject.

Metastasis is considered the deadliest step in cancer, and new and more effective therapeutic approaches are needed. As described herein, applicants have defined tumor exosomes as new agents that influence pre-metastatic niche formation and the progression of metastasis by altering bone marrow-derived cell (BMDC) phenotype via a process called "bone marrow cell education." Tumor-shed exosomes promote a pro-vasculogenic and pro-metastatic phenotype in BM progenitor cells that dramatically influences tumor metastasis. Targeting Ras-related proteins (Rab), particularly Rab27a, a protein involved in exosome production, results in reduced exosome production and failed recruitment of BMDCs, ultimately resulting in near abrogation of metastases. Inhibition of tumor-derived exosomes also reduced primary tumor growth. Applicants have also found that circulating levels of exosomes in plasma and specific proteins in the exosome fraction are diagnostic markers of metastasis in patients.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 1A is a representative electron microscopy image of exosomes derived from the plasma of a melanoma patient. Bar: 100 nm. FIG. 1B is a Kaplan-Meier survival curve showing cumulative probabilities in stage IV patients over 42 months of follow-up according to total protein (μg) in isolated circulating exosomes per milliliter of plasma analyzed (n=15). P values for the total model coefficients were calculated using log-rank test. FIG. 1C is a panel of representative western blot showing the expression of TYRP2, VLA-4, Hsp70, Hsp90 and Hsc70 proteins in circulating exosomes isolated from the plasma of melanoma patients (Stages I, III and IV) and healthy controls. Arrow indicates a specific isoform of Hsp90 found in 70% of melanoma patients. GAPDH was used as a loading control. Statistical analyses of western blot densitometry findings on the expression of signature proteins in circulating exosomes relative to GAPDH is shown in FIG. 1D. Controls (n=9); stage I (n=2); stage III (n=7); stage IV (n=18). FIG. 1E is a statistical analysis of western blot densitometry findings on TYRP2 expression in circulating exosomes relative to GAPDH in a retrospective series of frozen plasma derived from stage III melanoma patients (n=29) who had been followed for 4 years to evaluate disease progression. (NED=no evidence of disease, POD=progression of disease), (n=29).

FIG. 2B are fluorescent photomicrographic images showing the tissue distribution of exosomes (green) after tail vein injection of B16-F10 exosomes in mice. Confocal microscopy of sections from organs harvested 5 minutes (lung, left panel) or 24 hours after injection (lung and BM, right panels). FIG. 2C are fluorescent photomicrographs showing lung endothelial permeability by fluorescently-labeled dextran perfusion (red) 24 hours after tail vein injection of B16-F10 exosomes, conditioned media, or control particles. FIG. 2D shows an analysis of primary tumor growth (left panel) and lung metastasis (right panel) after orthotopic flank injection of B16-F10mCherry tumor cells in WT mice treated with B16-F10 exosomes for 3 weeks. Red arrows below x-axis in left panel indicate days of exosome injections (3 times a week). Synthetic liposomes and PBS were injected as controls for all in vivo exosome treatment experiments. The black arrow denotes the timepoint (Day 19) at which lung micrometastatic lesions were analyzed. n=6 mice per group; error bars represent s.e.m.; *P<0.05 by ANOVA. Representative lung images showing metastasis (mCherry staining, middle panels) after orthotopic flank injection of B16-F10mCherry tumor cells in WT mice treated B16-F10 exosomes or control animals are shown in the middle panel of FIG. 2D. Lung micrometastases were quantified by immunofluorescence counting mCherry-positive micrometastasis (FIG. 2D, right panel). FIG. 2E is a graph showing primary tumor growth after orthotopic flank injection of B16-F10mCherry-Luciferase tumor cells in mice pre-treated with 5 μg of B16-F10 or B16-F1 exosomes via intravenous injection three times a week for 28 days. After BM 'education', one million B16-F10mCherry-luciferase cells were injected into the flank of exosome-treated mice and controls and primary tumor size was measured over the course of 21 days. n=10 mice per group; error bars represent s.e.m. FIG. 2F shows metastatic burden in lungs and bones of mice treated with B16-F10, B16-F1 or control exosomes. Metastatic burden was determined by live luciferase imaging in lungs and bones, which is shown in FIG. 2F, left panel. Quantification of total photon flux in lungs and bones is shown in the graphs of FIG. 2F, n=10 mice per group; error bars represent s.e.m.; *P<0.05 with ANOVA FIG. 3A is a schematic of the experiment performed to analyze the influence of tumor exosomes in BM cell education and metastasis. GFP=green fluorescent protein. FIG. 3B is a graph charting primary tumor growth after orthotopic flank injection of B16-F10mCherry tumor cells in mice transplanted with B16-F10 exosome-educated BM (BM-educated). BM derived from mice treated with control particles (BM-control) and PBS was used in parallel, n=5 mice per group; error bars represent s.e.m.; ***P<0.001 by ANOVA. Confocal microscopy analysis of BMDCs (GFP-green) and vasculature (lectin-red) in primary tumors from BM-educated mice and controls is shown in the fluorescent photomicrographs of FIG. 3C. Quantification of vasculature in BM educated versus relative to BM-control by confocal is shown in the bottom left graph of FIG. 3C. Quantification of total BMDCs per confocal field analyzed is shown in the bottom right graph of FIG. 3C. n=5 mice per group; error bars represent s.e.m. FIG. 3D shows BMDCs (GFP-green) and metastatic B16-F10 cells (mCherry) in lung metastatic lesions at 28 days post-tumor injection (top fluorescent photomicrographs of FIG. 3D). Quantification of metastatic area in BM-educated relative to BM-control is shown in the bottom left graph of FIG. 3D. Quantification of total BMDCs per confocal field analyzed is shown in the bottom right graph of FIG. 3D. n=5 mice per group; error bars represent s.e.m. The bottom right photomicrographic images of FIG. 3D show the macroscopic analysis of lung metasatasis from mice after 35 days. FIG. 3E depicts the flow cytometric analysis of BM progenitor cell populations (c-Kit$^+$Tie2$^+$, CD105$^+$CD29$^+$c-Kit$^+$ and c-Kit$^+$Sca1$^+$) in mice educated with B16-F10 and B16-F1 exosomes for 28 days. BM from mice treated with control particles (control)

and PBS were analyzed in parallel. n=5 mice per group; error bars represent s.e.m.; n.s.=non significant by ANOVA.

Figures 4A, 4B:
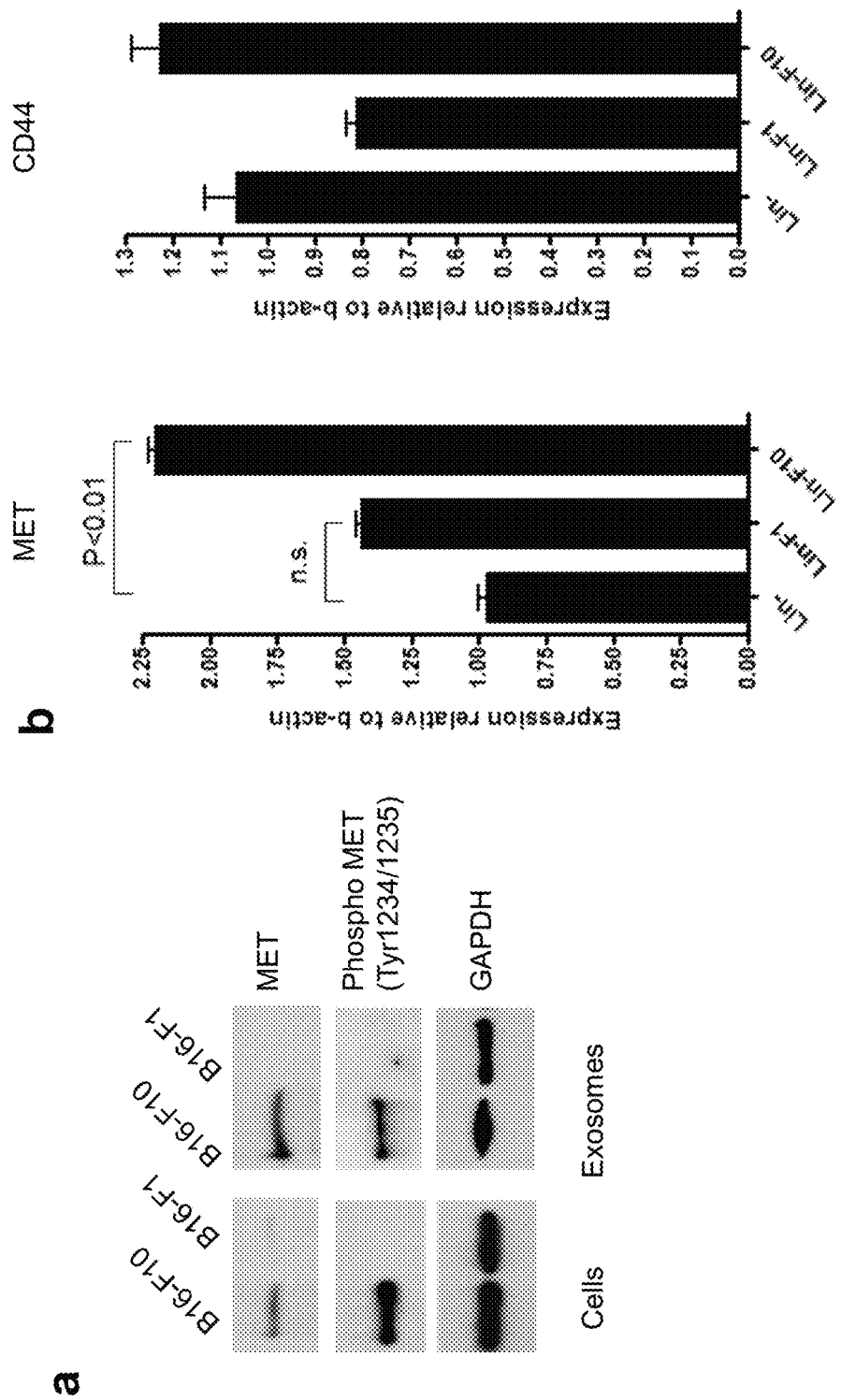
Figure 4C:
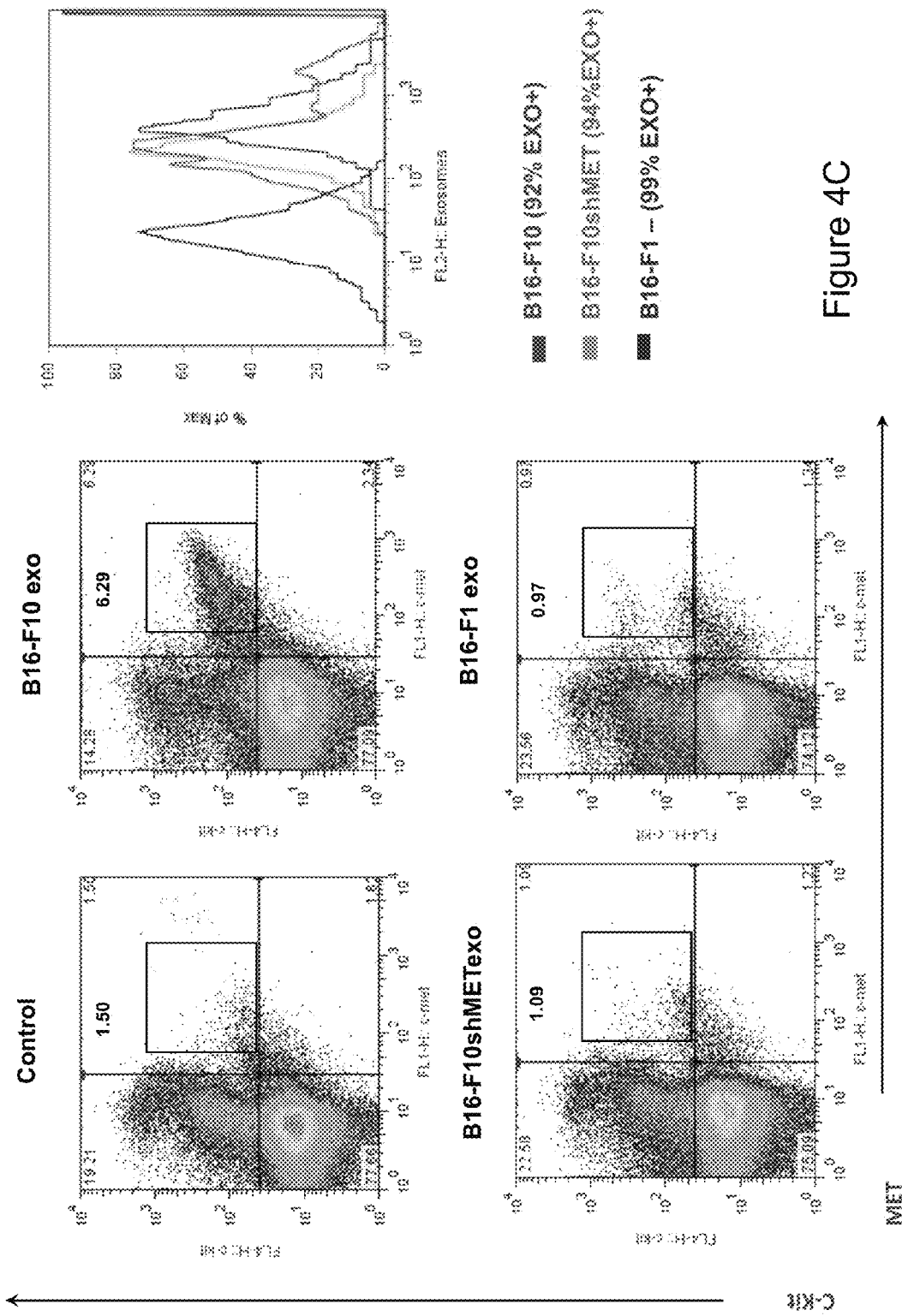
Figure 4D:
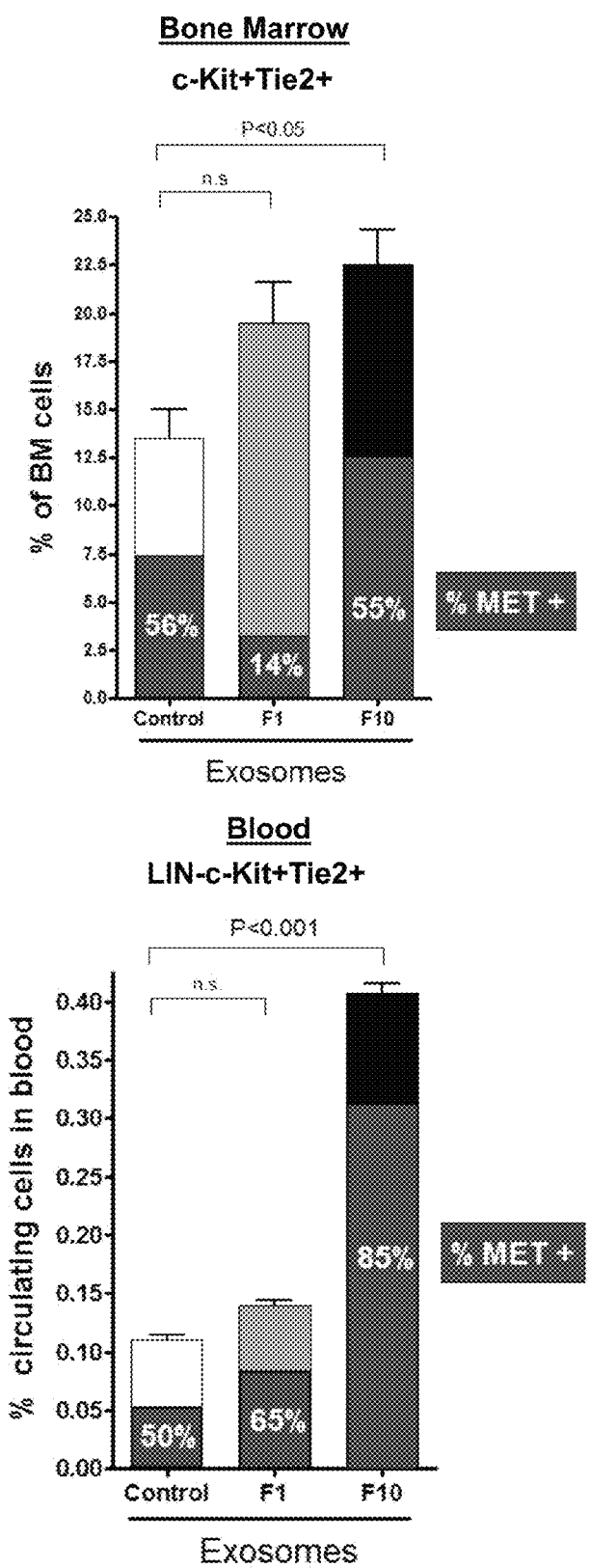
Figure 4E:
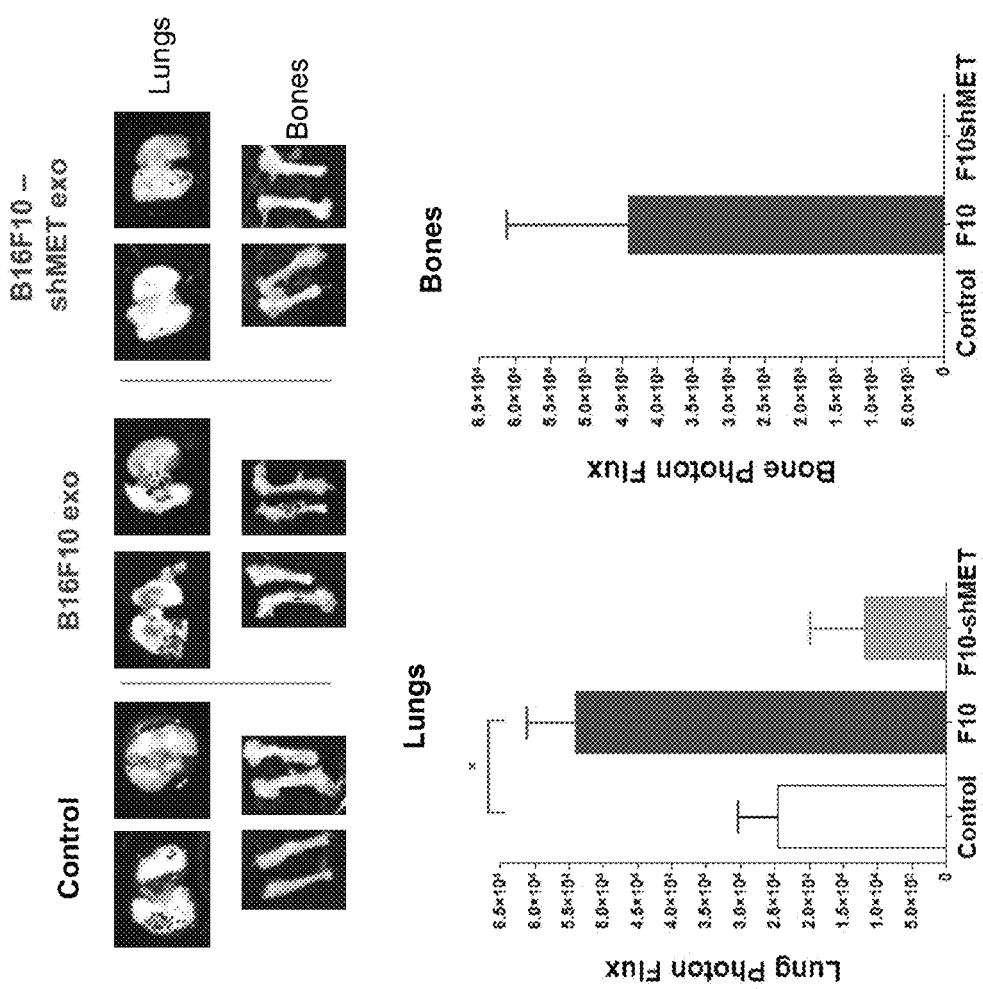
Figure 4F:
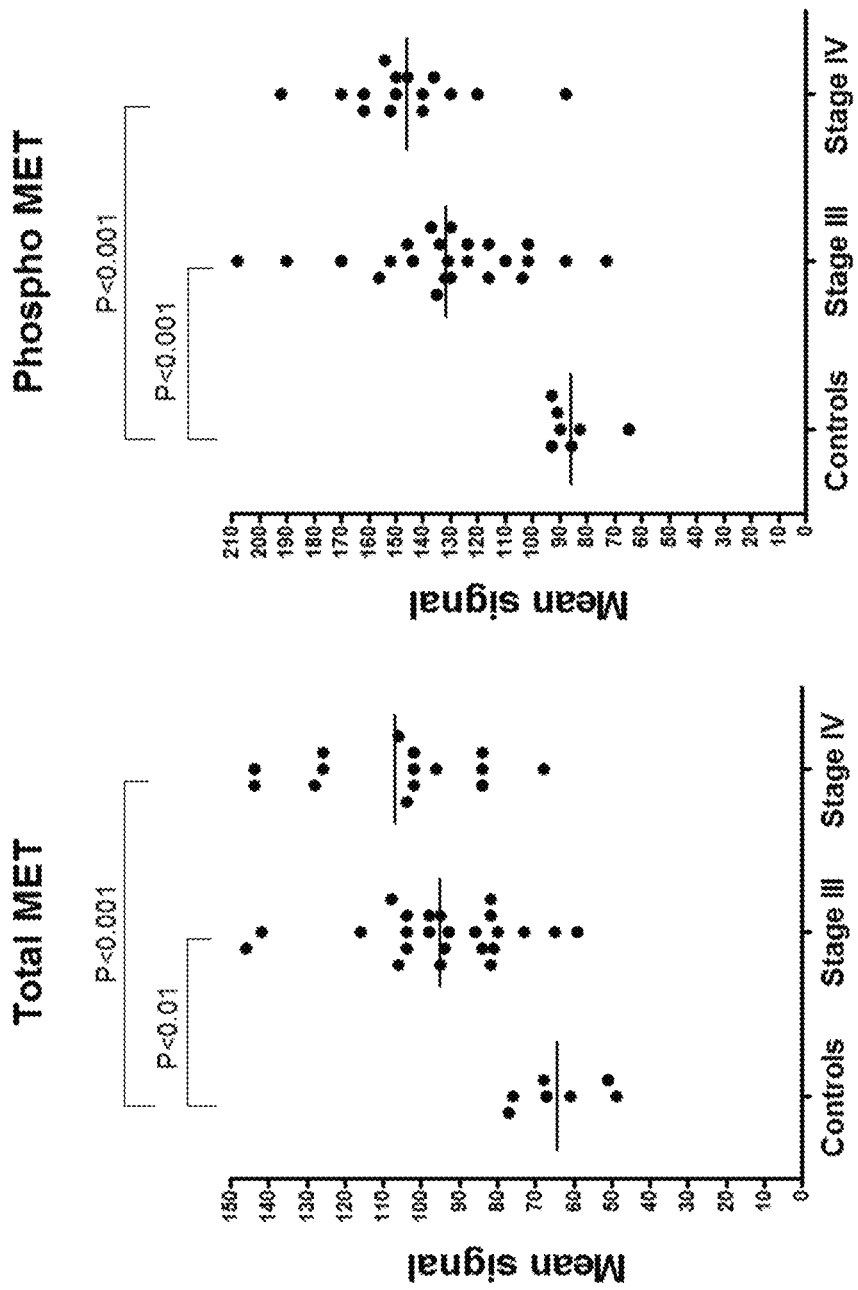
Figure 4G:
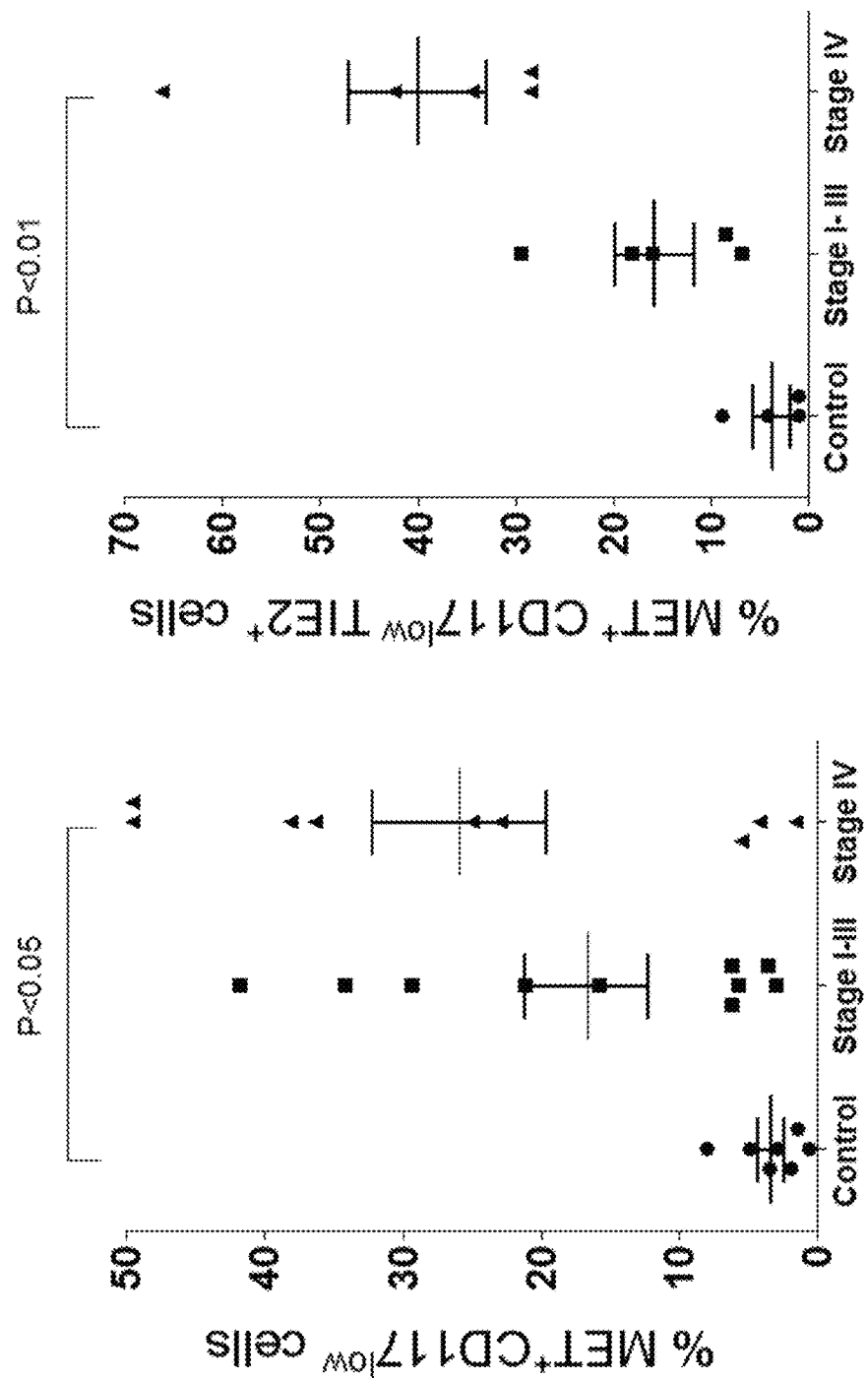

FIGS. 4A-4G demonstrate the horizontal transfer of MET from melanoma exosomes to BM cells. FIG. 4A is a western blot analysis of MET and phospho MET (Tyr 1234/1235) showing protein expression in B16-F1 and B16-F10 exosomes and cells. FIG. 4B are graphs showing the qRT-PCR analysis of MET and CD44 expression in BM progenitor cells (lineage-negative BM fraction) from mice treated with B16-F10 and B16-F1 exosomes 3 times a week for 28 days (educated). Expression is shown relative to β-actin and control. Error bars represent s.e.m.; n.s.=not significant by ANOVA. FIG. 4C shows the flow cytometry analysis for c-Kit and MET expression in BM cells after overnight in vitro treatment with fluorescent labeled exosomes (PKH26$^+$) derived from B16-F10, B16-F10shMET and B16-F1 cells. The four panels show representative BM populations. An analysis of exosome uptake in B16-F10, B16-F1 and B16-F10shMET cells is shown graphically in the right panel of FIG. 4C. 92% of B16-F10 (red line), 94% of B16-F1 (blue line) and 99% of F10-shMET were exosome-positive cells (FL2+). Note that B16F10shMET- and B16-F1-derived exosomes showed no transfer or change in BM MET expression. FIG. 4D (top graph) shows the flow cytometric analysis of MET expression after gating in c-Kit$^+$Tie2$^+$ progenitor cells in BM of mice educated with B16-F10 and B16-F1 exosomes 3 times a week for 28 days (top panel, red area=% of MET$^+$ cells after gating in c-Kit$^+$Tie2$^+$ population). Analysis in the same experiment of MET expression in Lin-c-Kit+Tie2+ circulating BM cells is shown in the bottom graph of FIG. 4D (red area=% of MET$^+$ cells after gating in Lin-c-Kit+Tie2+ population). Mice treated with control particles (control) and PBS were analyzed in parallel. Error bars represent s.e.m.; n.s.=not significant by ANOVA. FIG. 4E depicts metastasis of B16-F10mCherry-Luciferase tumor cells in mice educated with 5 µg of B16-F10 or B16-F10shMET exosomes intravenously injected three times a week for 28 days. After BM 'education', one million B16-F10mCherry-Luciferase cells were subcutaneously implanted in exosome-treated mice and controls, and primary tumor size was measured (n=5 mice per group). Metastatic burden is shown by live luciferase imaging in lungs and bone as shown in the top panel of images in FIG. 4E. Quantification of total photon flux in lungs and bones is shown in the bottom panel of FIG. 4E. Error bars represent s.e.m.; *P<0.05 with ANOVA. FIG. 4F is an analysis by multiplex assay of MET (left graph) and phospho-MET (Tyr1349) (right graph) levels in the circulating exosomes isolated from a retrospective series of frozen plasma derived from Stage III and IV melanoma patients and controls. Controls (n=7); Stage III (n=24); Stage IV (n=15). P<0.01; *P<0.001 by ANOVA. Flow cytometry analysis showing the percentage of MET+ circulating BM progenitor cells (CD45$^-$CD117$^{low/+}$ (FIG. 4G, left graph) and CD45$^-$CD117$^{low/+}$Tie2$^+$ (FIG. 4G, right graph) in the blood of Stages I-III and IV melanoma patients is shown in FIG. 4G. Controls (n=7); stage I-III (n=10); stage IV (n=9). Error bars represent s.e.m; *P<0.05; **P<0.01 by ANOVA.

Figures 5B, 5C:
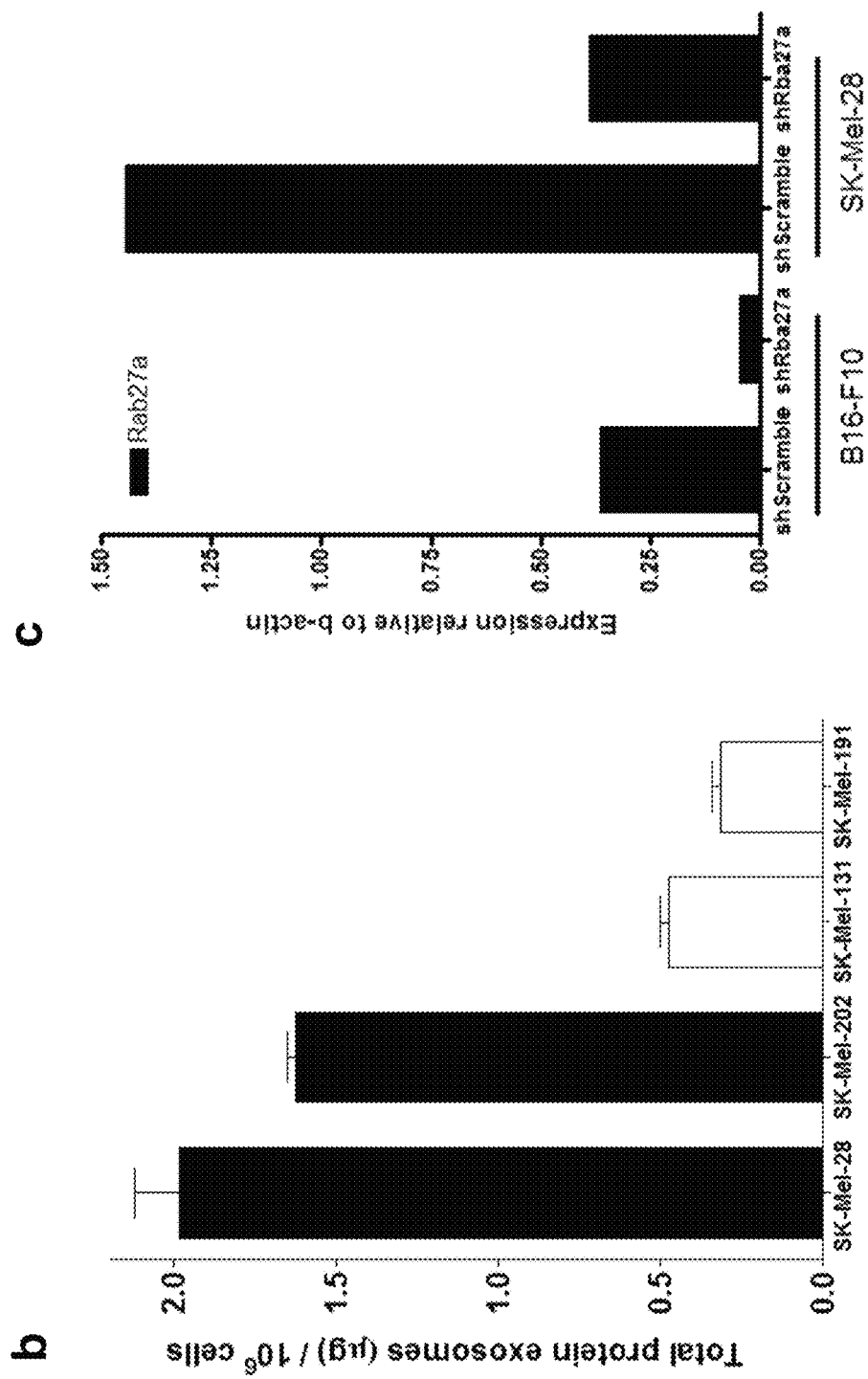
Figure 5D:
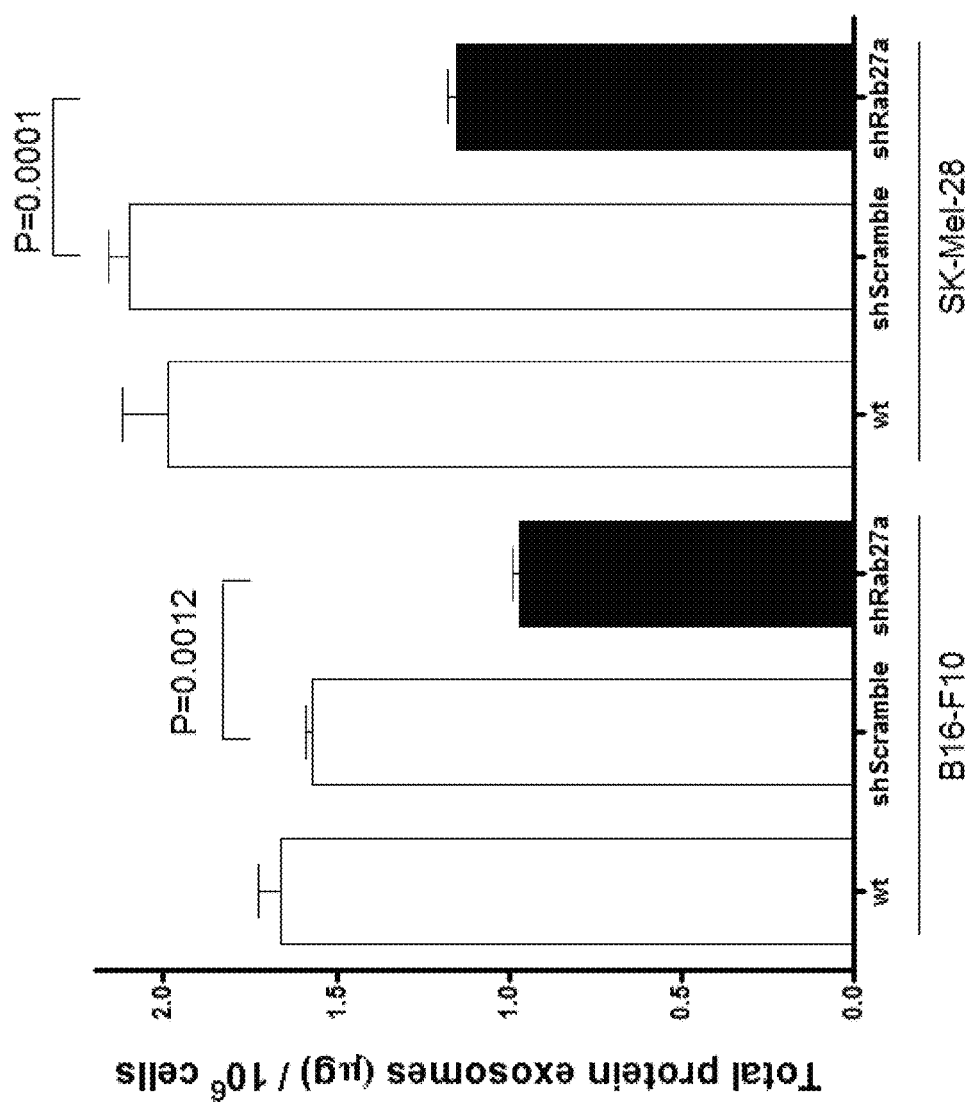
Figure 5E:
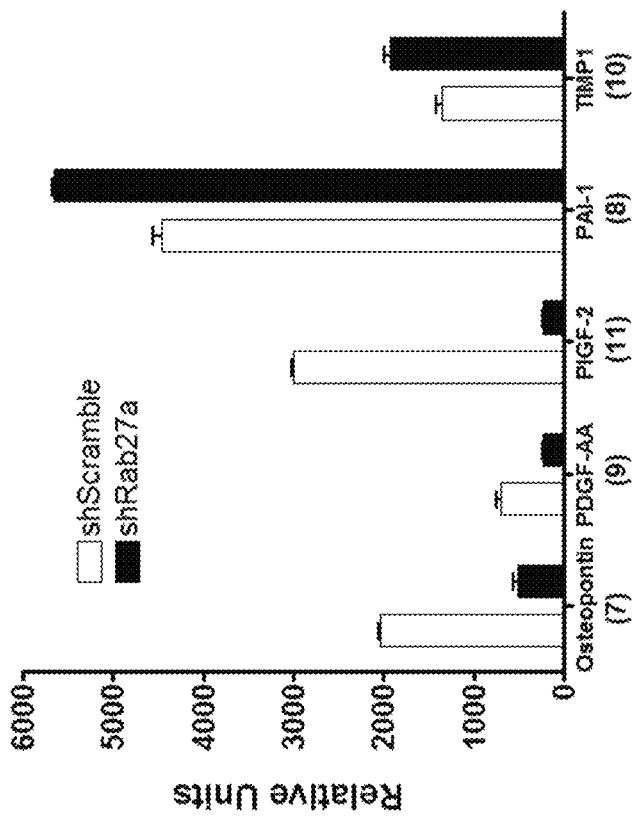
Figure 5E:
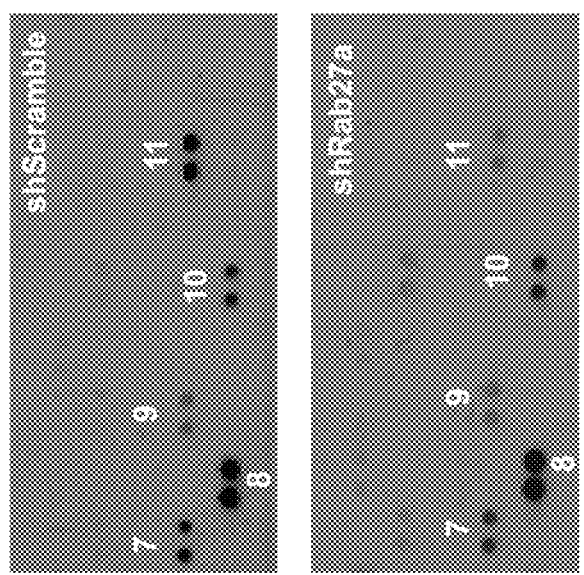
Figure 5F:
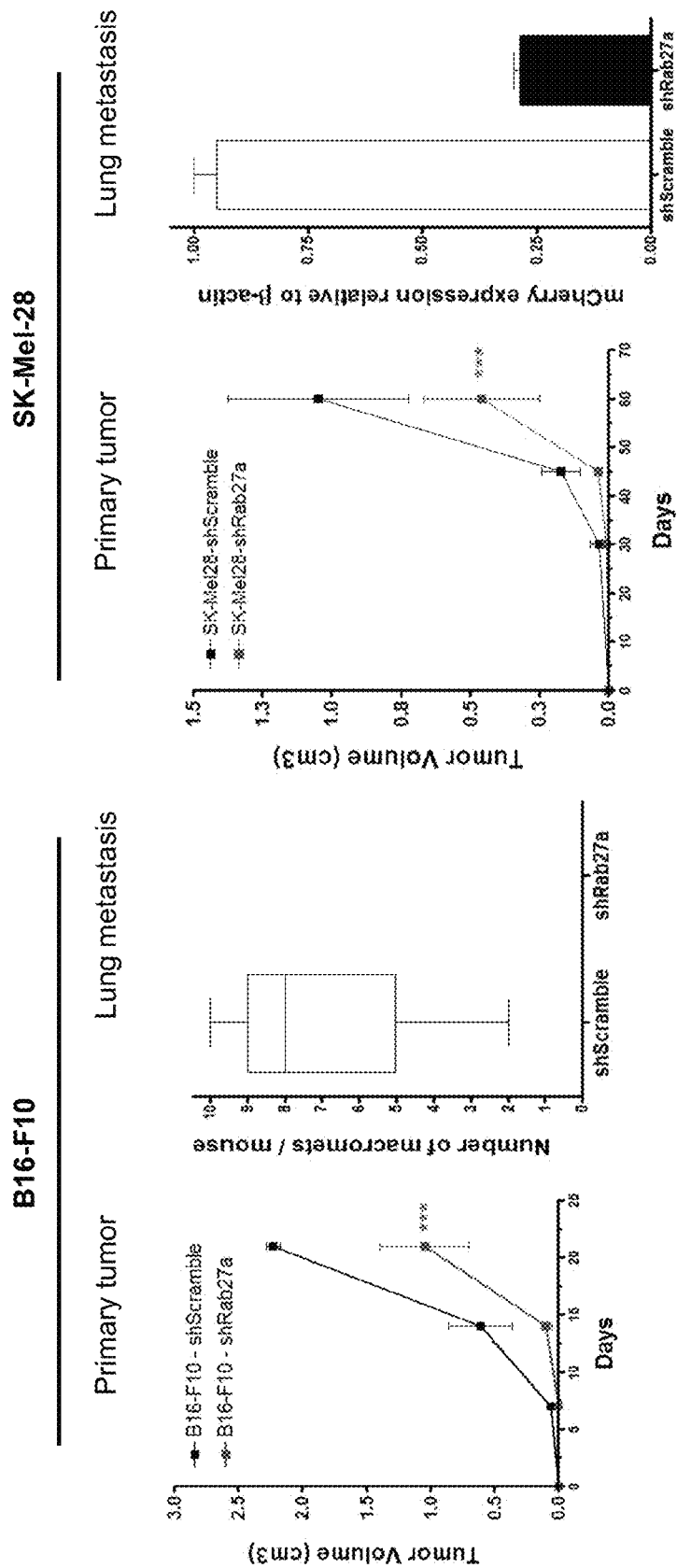
Figure 5G:
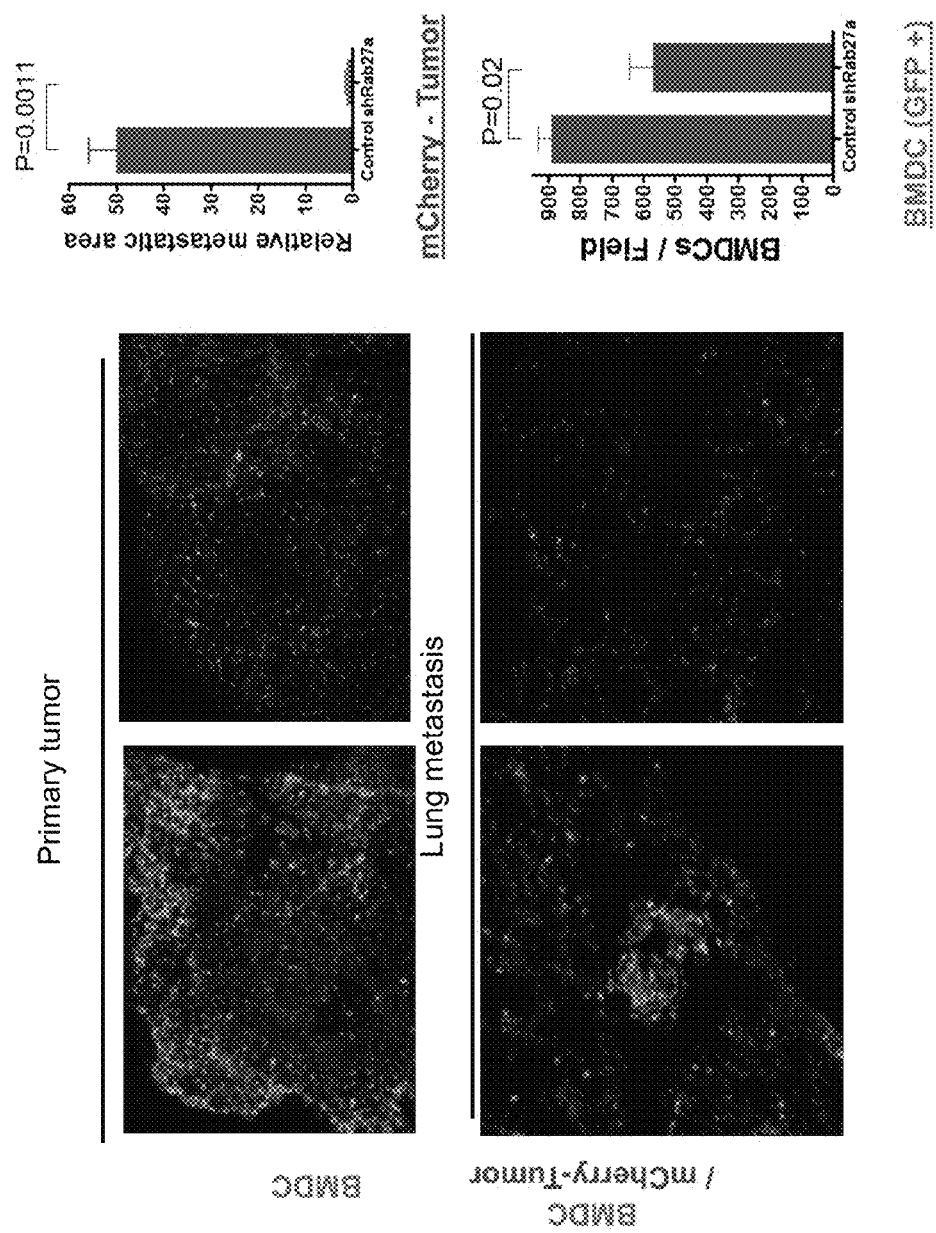

FIGS. 5A-5G show that Rab27a interference reduces exosome release, primary tumor growth, and metastasis. FIG. 5A is a table depicting the results of a QRT-PCR analysis of the indicated Rab genes in 30 melanoma (SK-Mel-#), breast cancer (MCF7, MDA-MB-231, SkBr3) and pancreatic adenocarcinoma (AsPc1) cell lines. Red (+++) denotes high expression (>2-fold relative to expression in breast cancer and pancreatic cell lines), yellow (+) indicates intermediate expression (<2-fold and >1.5-fold), and green (+) indicates low or undetectable expression (<1.5-fold). FIG. 5B is a graph showing the measurement of the total protein in the exosome fraction per million of cells isolated from SK-Mel28, -202, -131, and -191 human melanoma cells in culture. FIG. 5C is a graph showing QRT-PCR analysis of Rab27a expression after shRNA knock-down of Rab27a in B16-F10 and SK-Mel-28 cell lines. FIG. 5D is a graph showing the measurement of total protein in isolated exosomes per million of cells after shRNA knock-down of Rab27a (sh-Rab27a) in B16-F10 and SK-Mel28 cell lines. Control scramble shRNA and WT cells were used as a reference. FIG. 5E shows the characterization and densitometric analysis of conditioned media derived from B16-F10-shScramble and -shRab27a cell lines by mouse angiogenesis array kit. 7=osteopontin, 8=PAI-1, 9=PDGF-AA, 10=TIMP1, 11=P/GF-2. FIG. 5F depicts the analysis of primary tumor growth and metastasis in shScramble, sh-Rab27a-B16-F10 cell lines and shScramble-, sh-Rab27a-SK-Mel-28 cell lines orthotopically injected into the flank of C57BL/6 or NOD-SCID mice, respectively. Metastases were macroscopically counted in lungs of mice injected with B16-F10 cells or quantified by qRT-PCR for mCherry in mice injected with SK-Mel-28 cells. n=5 mice per group; error bars represent s.e.m.; ***P<0.001 by ANOVA. In FIG. 5G, confocal microscopy of BMDCs (GFP=green) and tumor cells (mCherry-tumor=red) in primary tumor (top panel of fluorescent images) and metastatic lesions (bottom panel of fluorescent images) from B16-F10-shScramble (left fluorescent images) and B16-F10-shRab27a (right fluorescent images). Quantification of the metastatic area relative to control (top graph; right panel of FIG. 5G) and quantification of total BMDCs per confocal field analyzed (bottom graph; right panel of FIG. 5G). n=5 mice per group; Error bars represent s.e.m.

Figures 6A, 6B, 6C:
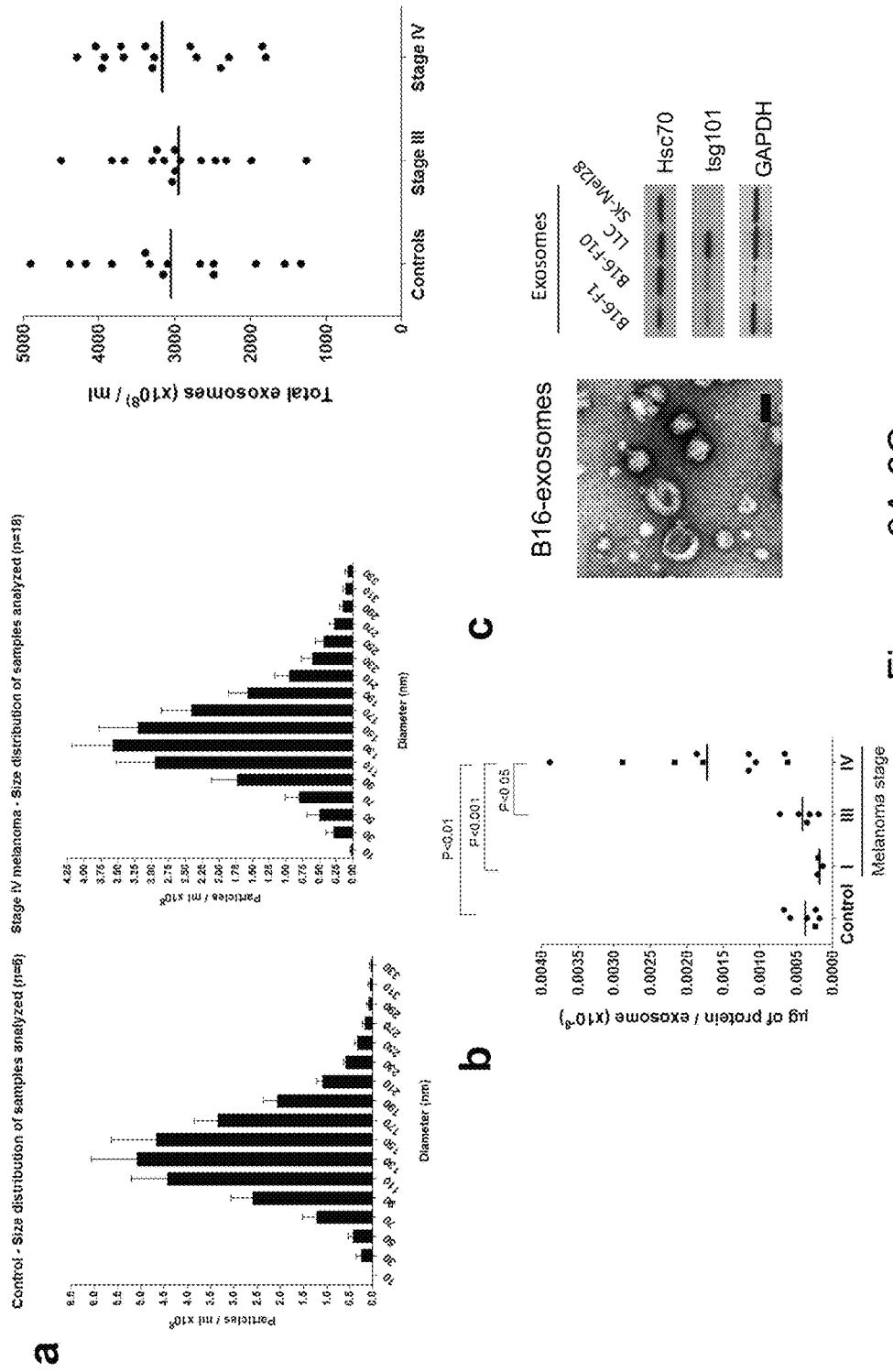

FIGS. 6A-6C depict the characterization of human circulating exosomes. Exosomes isolated from plasma derived from healthy controls and melanoma patients were measured by Nanoparticle Tracking Analysis (NanoSight). FIG. 6A are graphs showing the heterogeneous distribution (left and middle graphs) of number (×10$^8$, y axis) and size (x axis) of the particles found in human fresh plasma of healthy donors (left graph "control"; n=8) and stage IV melanoma patients (right; n=16). Error bars represent ±s.e.m. Analysis of total circulating exosomes in the plasma of healthy donors and melanoma patients (Stage III and IV) is shown in the far right graph of FIG. 6A. The results are presented as the total number of exosomes (×10$^8$) per milliliter of plasma.

FIG. 6B is a graph showing protein content per exosome in circulating exosomes in healthy donors and melanoma patients (Stages I, III, and IV). The results are represented as the total micrograms of protein divided by the total number of exosomes measured (×10$^8$) with Nanoparticle Tracking Analysis (NanoSight). Electron microscopy imaging of exosomes derived from B16-F10 melanoma cells in culture reveals the presence of 30-100 nm particles as shown in FIG. 6C left image panel (Bar=100 nm). Western blot analysis of exosomes isolated from the supernatant fraction of B16-F1, B16-F10, LLC and SK-Mel28 cell lines demonstrates the presence of exosome markers Hsc70 and tsg101, confirming the origin from an exosomal compartment (FIG. 6C, right panel).

Figure 7A:
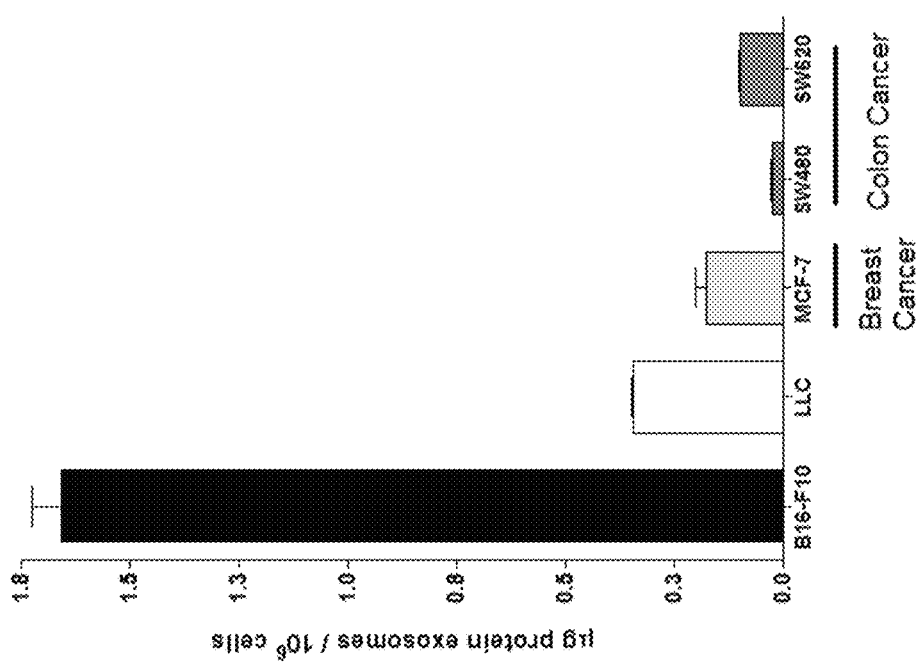
Figure 7B:
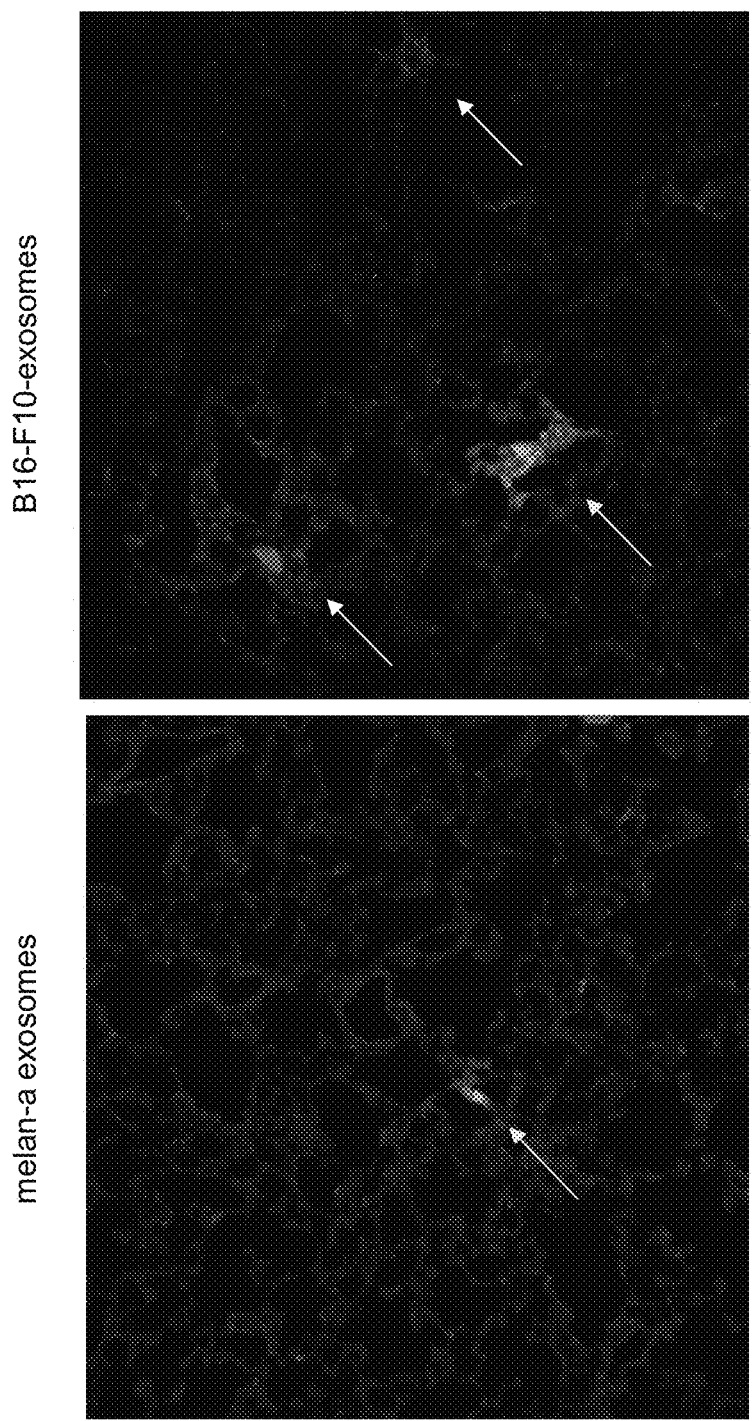
Figure 7C:
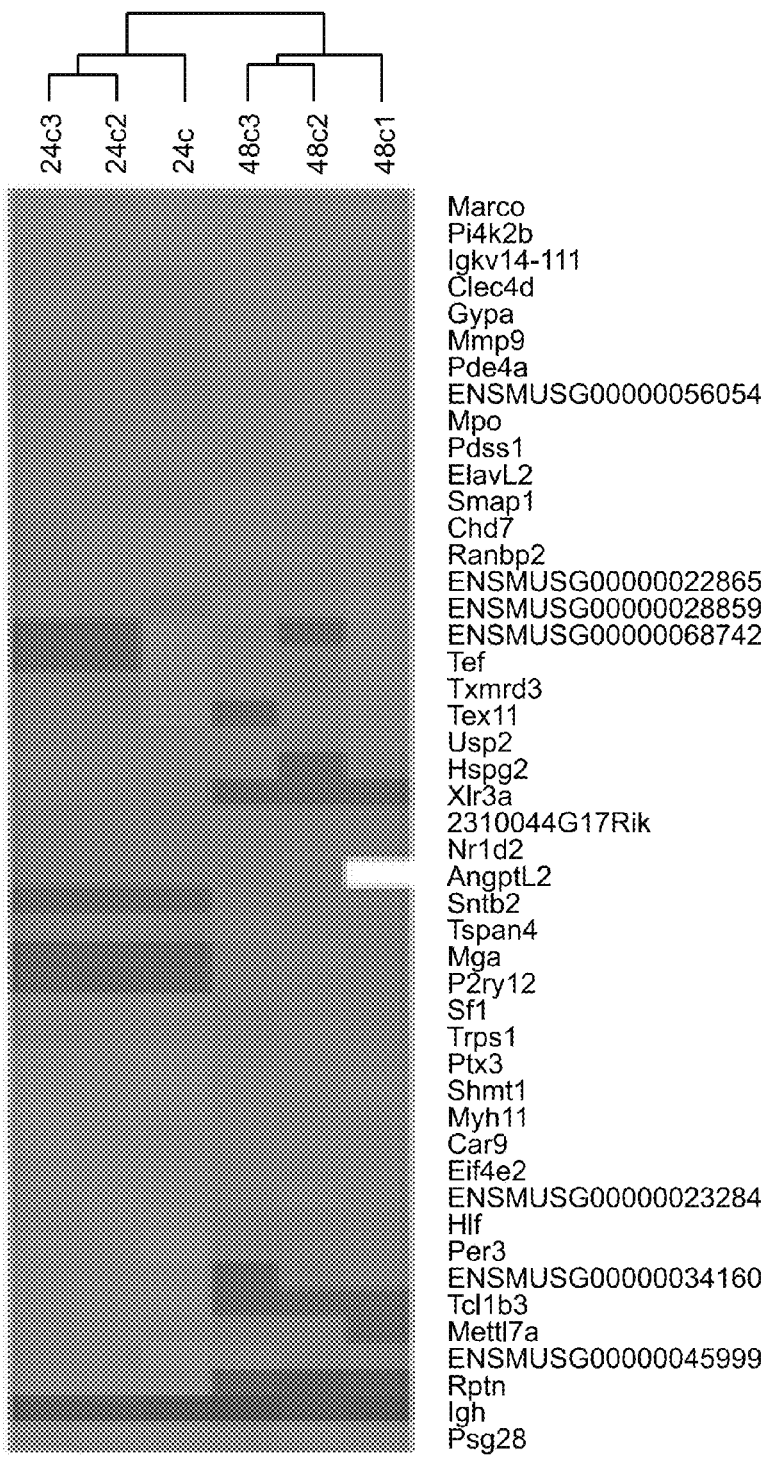
Figure 7C:
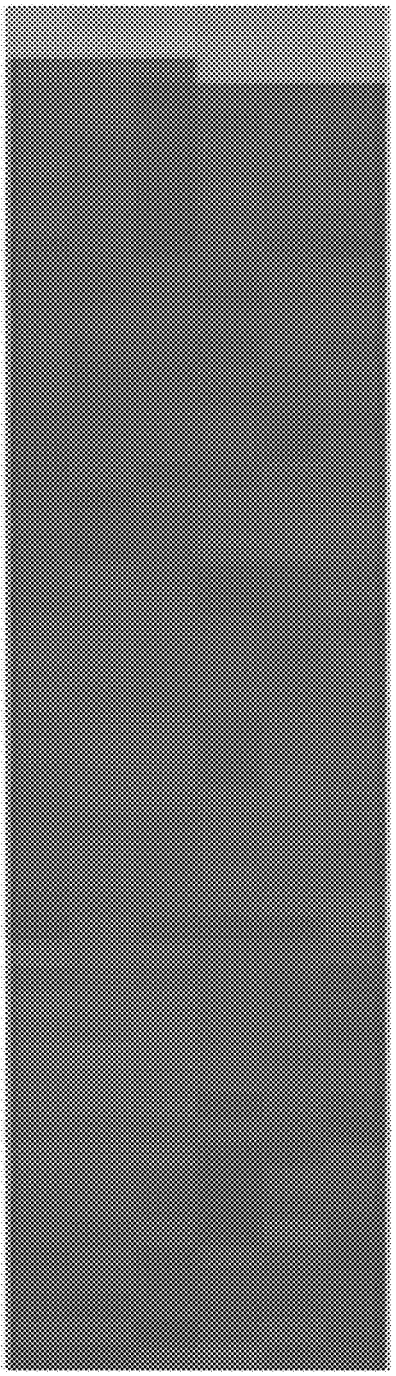
Figure 7C:
Figure 7C:
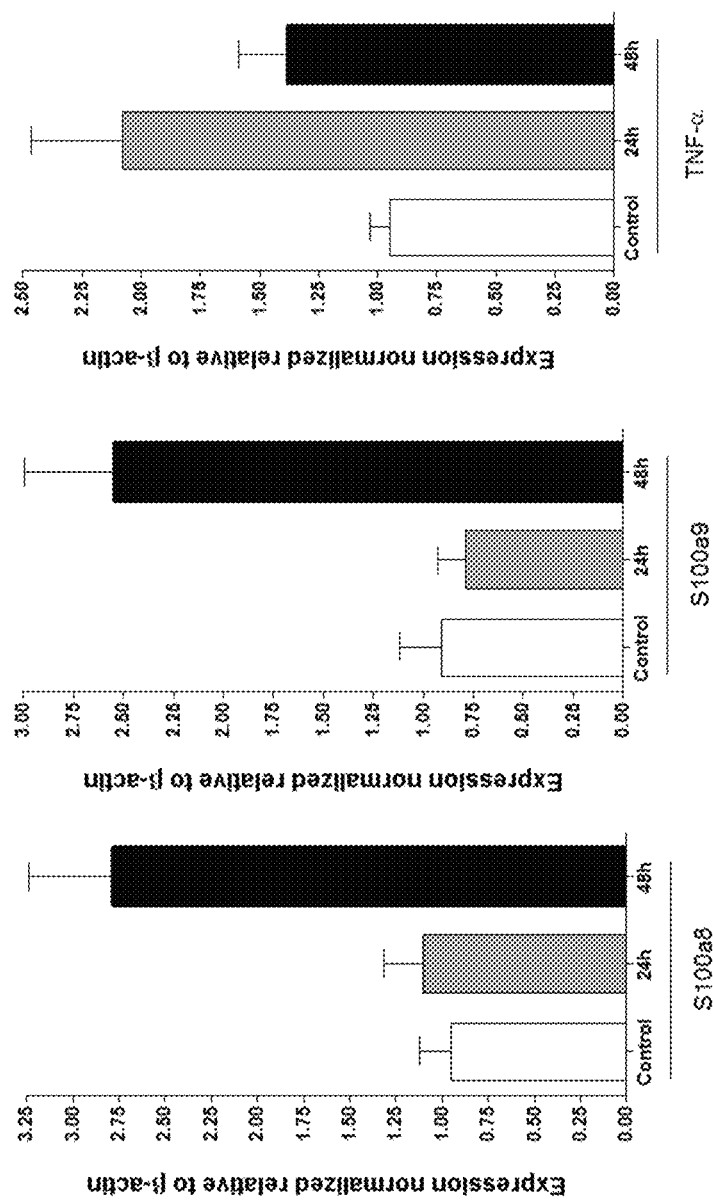

FIGS. 7A-7C demonstrate exosome effects in metastatic organs. FIG. 7A is a graph depicting the measurement of total protein per million cells in the exosomes isolated from low metastatic murine lung cancer cells (LLC), human breast cancer (MCF-7) and human colon cancer cells (SW480 and SW620) compared to highly metastatic B16-

F10 mouse melanoma cells in culture. Error bars represent ±s.e.m. FIG. 7B are fluorescent photomicrographs showing lung vessel leakiness 24 hours after tail vein injection of melan-a and B16-F10 exosomes. Yellow arrow: labeled exosomes. White arrow: endothelial leakiness. FIG. 7C shows the microarray cluster analysis of genes differentially expressed in lungs 24 and 48 hours after B16-F10 exosome tail vein injection compared to control. QRT-PCR analysis of S100a8, S100a9, and TNF-α from RNA isolated from lungs 24 and 48 hours after B16-F10 exosome tail vein injection is shown in the three graphs of FIG. 7C.

Figures 8A, 8B:
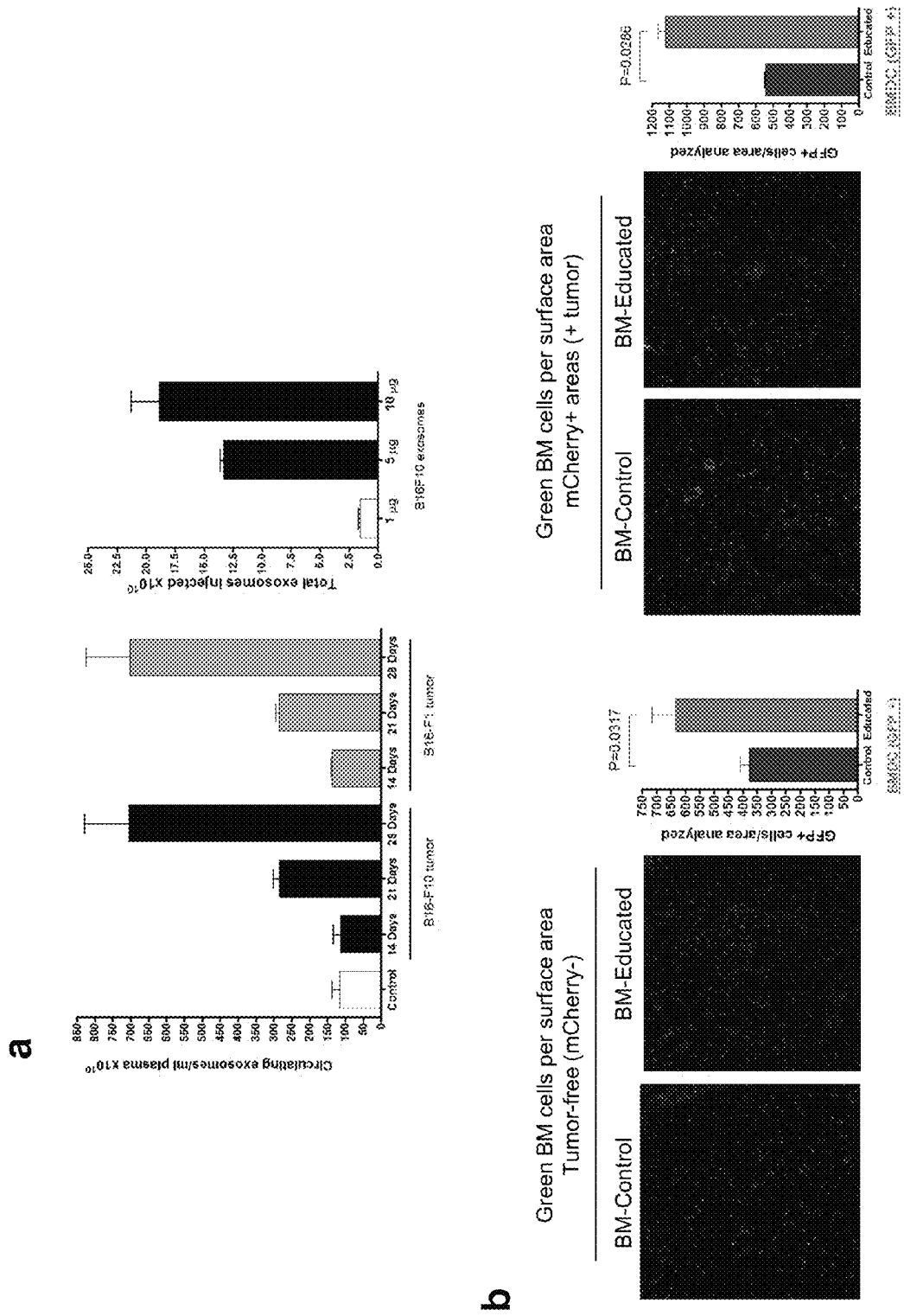

FIGS. 8A-8B show the analysis of mouse exosomes and their effects on primary tumor vasculature and primary tumor BMDC infiltration. Characterization of total circulating exosome levels in the plasma of control mice or mice bearing day 14, 21 and 28 B16-F10 or B16-F1 tumors is shown in FIG. 8A, left graph. The results are presented as the total number of exosomes ($\times 10^{10}$)/ml of plasma. Analysis of total tumor exosome injected in mice for BM education experiments by NanoSight technology (FIG. 8A, right panel). The results are presented as the total number of exosomes ($\times 10^{10}$) per injection of 1, 5 and 10 µg. Error bars represent ±s.e.m. FIG. 8B depicts the analysis of BMDCs (GFP-green) in lungs from BM-educated mice and controls by confocal microscopy. Quantification of total BMDCs per confocal field analyzed in tumor-free areas (left panel) or areas with metastasis (mCherry+, right panel) is shown in the graphs of FIG. 8B. n=5 mice per group; error bars represent s.e.m.

Figures 9A, 9B:
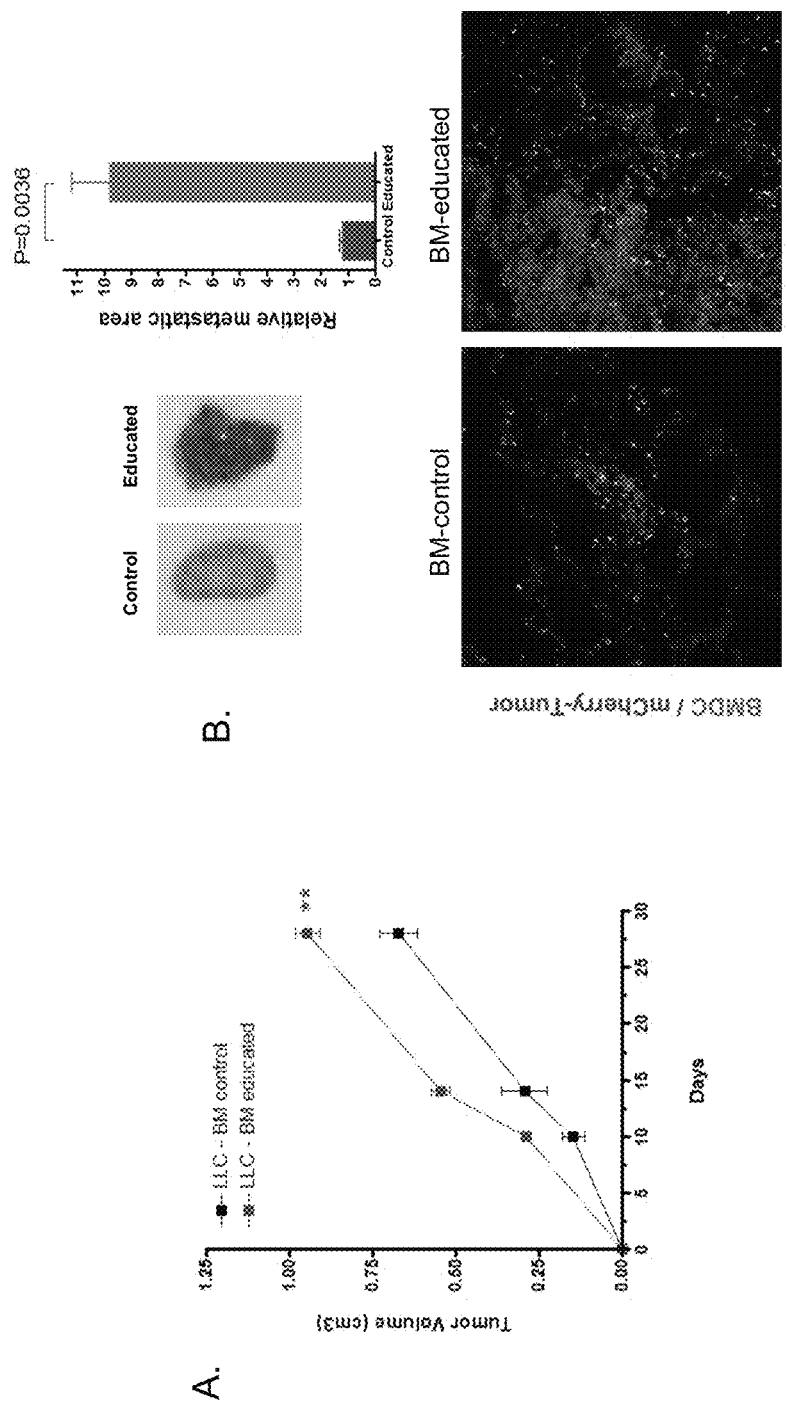

FIGS. 9A-9B show the analysis of primary tumor growth after orthotopic flank injection of LLC cells. FIG. 9A is a graph charting primary tumor growth in mice transplanted with B16-F10 exosome-educated BM or BM derived from mice treated with 100 nm size unilamellar liposomes (BM-control). FIG. 9B shows the analysis of macrometastasis and micrometastasis that was performed by measuring the metastatic area (mCherry staining) in lungs after 28 days in mice transplanted with BM-educated vs. BM control cells. Photomicrographs of whole lung tissue from BM-educated vs. BM-control animals are shown in the top left panels of FIG. 2B. Fluorescent micrographs showing BMDC staining (green) and mCherry staining (red) are shown in bottom panels of FIG. 9B. Quantification of the metastatic area relative to control is shown in the graph of FIG. 9B. n=10 mice per group; error bars represent s.e.m; **P<0.001 by ANOVA.

Figures 10A, 10B, 10C, 10D, 10E:
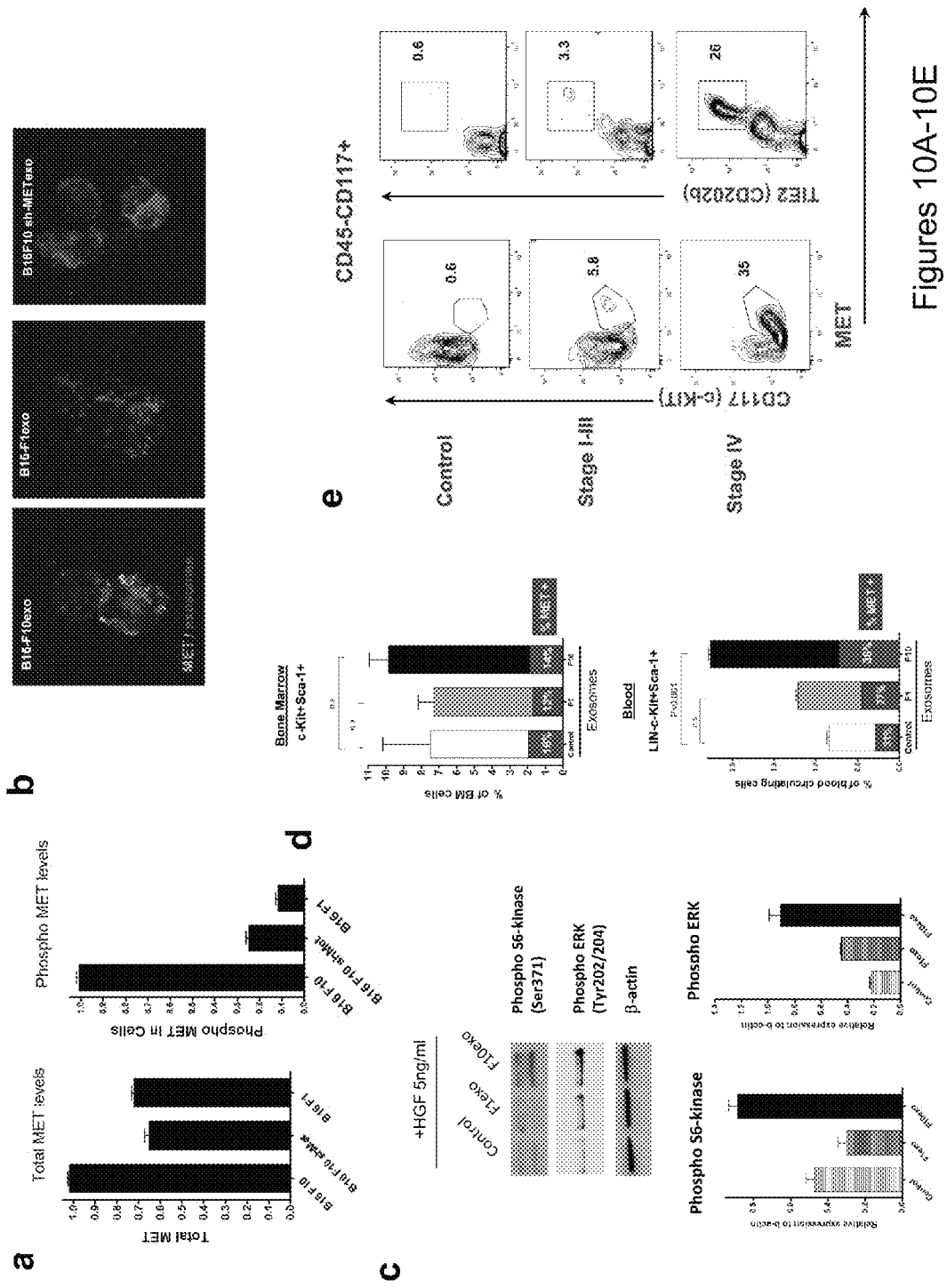

FIGS. 10A-10E show the analysis of MET expression in melanoma and BM cells. FIG. 10A are graphs showing MET and phospho MET expression in B16-F10 cells, B16-F1 cells, and B16-F10 cells containing MET shRNAs (shMET). FIG. 10B is a panel of fluorescent photomicrographs showing the analysis of horizontal transfer of MET receptor to BM cells by immunofluorescence after overnight in vitro treatment with B16-F10 exosomes (left panel; exosomes labeled in red, MET in green). B16-F10shMET-derived exosomes (right panel) and B16-F1-derived exosomes (middle panel) showed no horizontal transfer or change in MET expression (exosomes labeled in red, MET in green). FIG. 10C is a western blot analysis of phospho-S6 kinase (Ser371) and phospho ERK (Tyr202/Tyr204) in BM cells pre-treated with B16-F10 exosomes and B16-F1 exosomes for 16 hours and then stimulated with HGF (5 ng/ml) for 4 hours. β-actin was used as loading control. Quantitation of phosphor S6-kinase and phospho ERK expression is shown in the graphs below the blots. FIG. 10D (top graph) shows MET expression by flow cytometry in c-Kit+Sca1+ progenitor cells in BM of mice educated with B16-F10 and B16-F1 exosomes 3 times a week for 28 days (red area=% of MET$^+$ cells after gating in c-Kit+Sca1+ population). FIG. 10D (bottom graph) show MET expression by flow cytometry in Lin-c-Kit$^+$Sca1$^+$ of circulating blood BM cells (red area=% of MET$^+$ cells after gating in Lin-c-Kit+Sca-1+ population). Mice treated with control particles (control) and PBS were analyzed in parallel. Error bars represent s.e.m.; n.s.=non-significant; P<0.01; *P<0.001 by ANOVA. FIG. 10E shows representative flow cytometric analysis of MET expression in circulating BM progenitor cells (CD45$^-$CD117$^{low/+}$ and CD45$^-$CD117$^{low/+}$TIE2$^+$) from the blood of Stage I-III and IV melanoma patients and control subjects.

Figures 11A, 11B, 11C, 11D:
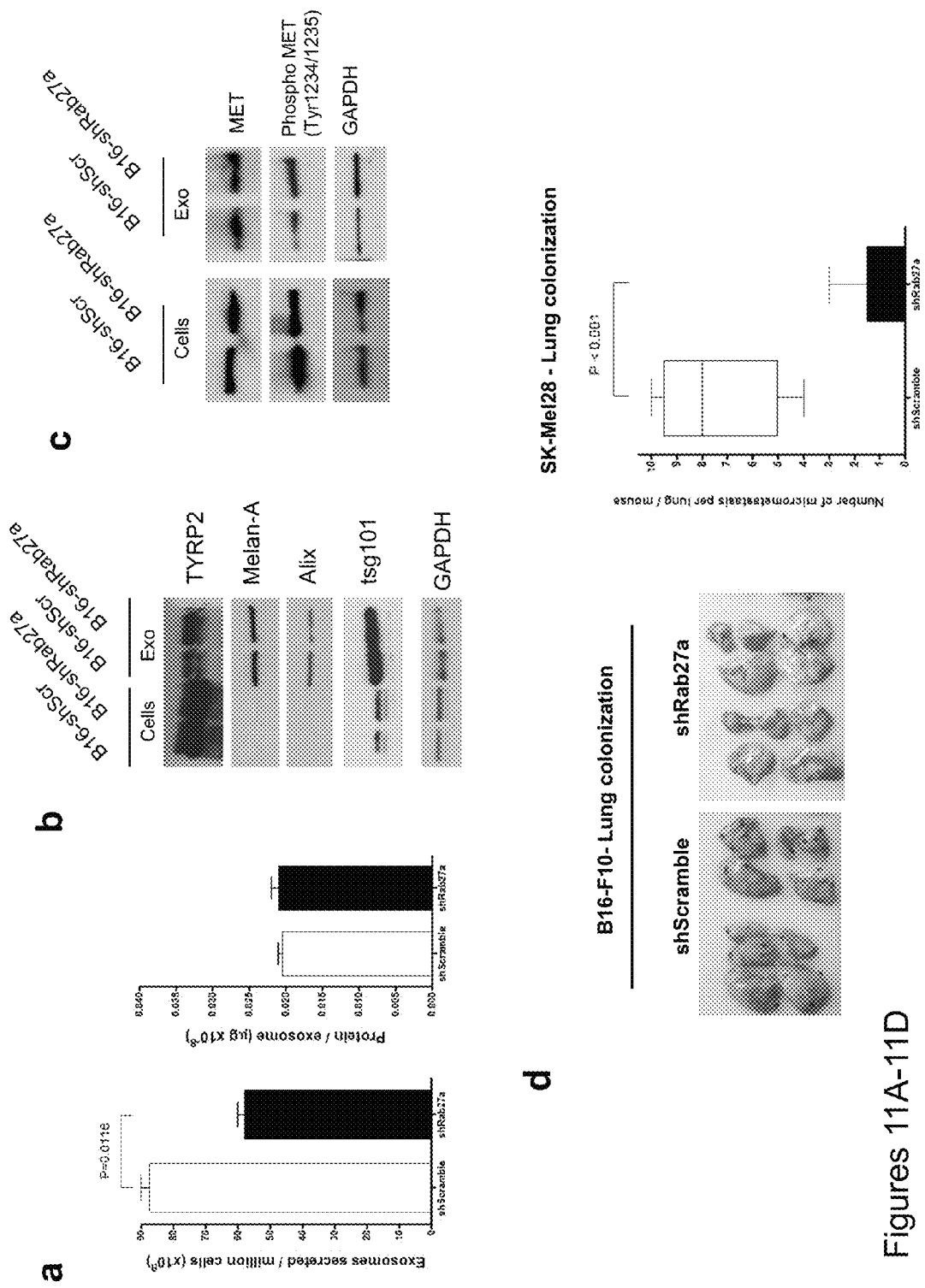

FIGS. 11A-11D shows Rab27a interference reduces exosome release from B16-F10 cells, reducing their lung colonization. The left graph of FIG. 11A shows total exosomes secreted by B16-F10-shScramble and B16-F10-shRab27a cell lines as measured by NanoSight technology. The results are presented as the total number of exosomes ($\times 10^8$) per milliliter. The right graph of FIG. 11A shows total protein per exosome in B16-F10-shScramble and B16-F10-shRab27a cell lines. The results are represented as the total micrograms of protein divided by the total number of exosomes measured ($\times 10^8$) by Nanoparticle Tracking Analysis (NanoSight). Error bars represent s.e.m. FIG. 11B shows representative western blot analysis of melanoma (TYRP2, Melan-A) and exosome markers (Hsc70, tsg101) in B16-F10-shScramble and -shRab27a cell lines (cells) and exosomes (exo). FIG. 11C shows representative western blot analysis of MET and phospho MET (Tyr1234/1235) expression in B16-F10-shScramble and -shRab27a cell lines (cells) and exosomes (Exo). FIG. 11D shows an analysis of lung metastasis following shScramble or shRab27a B16-F10 (left) or SK-Mel-28 (right) cell line tail vein injection. Gross metastases were macroscopically counted in the lungs of mice injected with B16-F10 models (photomicrographs; left panel of FIG. 11D) and micrometastatic foci in the lung were counted by immunofluorescence (mCherry) in mice injected with SK-Mel-28 cell models (graph; right panel of FIG. 11D). n=5 mice per group; error bars represent s.e.m.

Figures 12A, 12B:
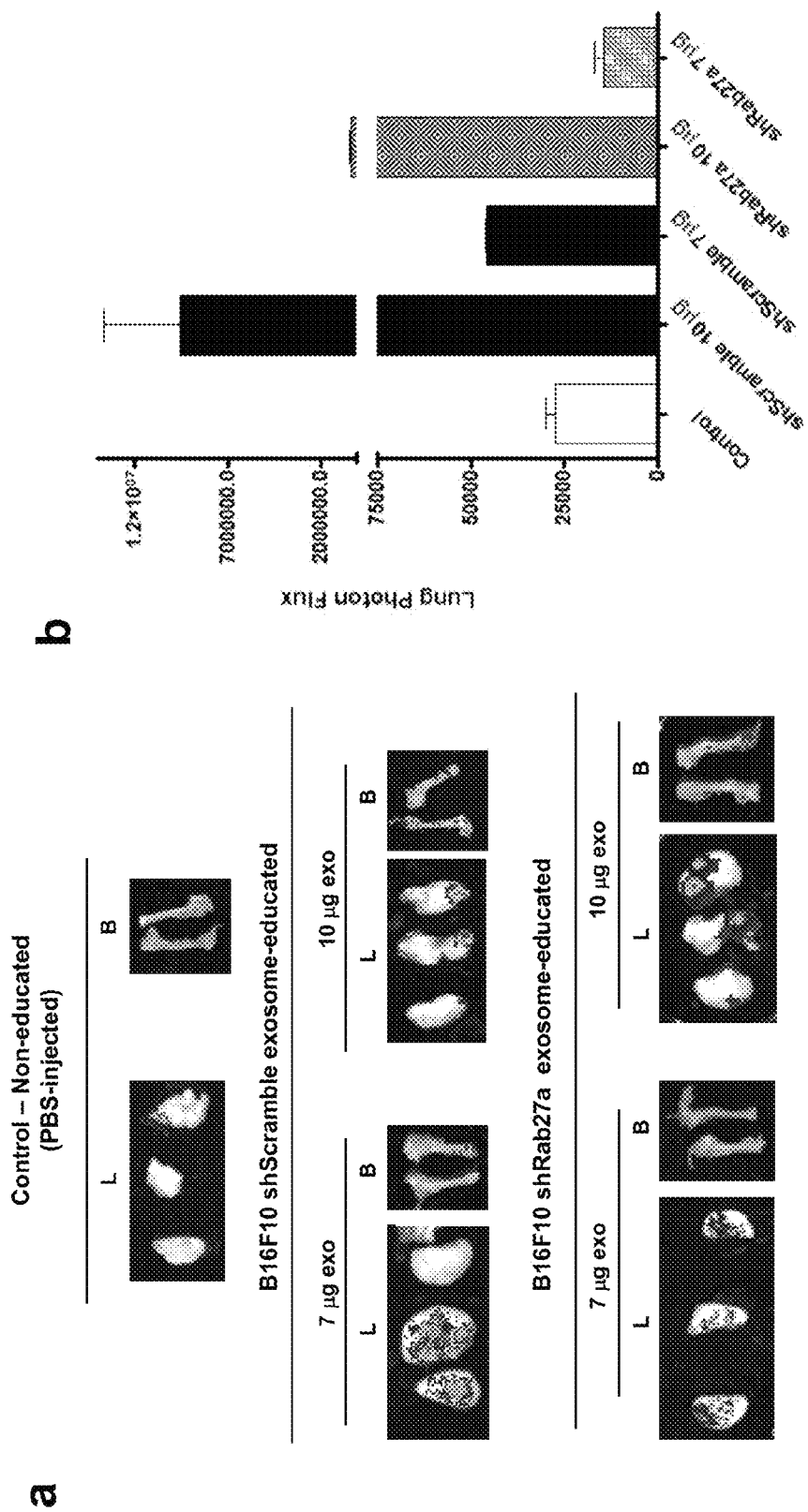

FIGS. 12A-12B show a dose response analysis of B16-F10Rab27a-shRNA exosomes and their influence on metastasis. FIG. 12A shows metastasis in mice treated with different doses of B16-F10 shScramble control exosomes (shScramble 7 and 10 µg) and B16-F10-shRab27a exosomes (7 and 10 µg) for 28 days. Mice were 'exosome-educated' for 28 days by injecting the indicated dose of exosomes 3 times a week. Mice injected with PBS following the same schedule were used as a control. After 28 days of 'exosome education' $1\times10^6$ B16mCherry-Luciferase cells were injected orthotopically in the flank of these mice. Metastasis was quantified at day 21 post tumor injection (n=5 mice per group in duplicate). Metastatic lesions were identified by luciferase expression in metastatic organs (lungs (L) and bones (B)). FIG. 12B shows quantification of total photon flux in lungs. Error bars represent s.e.m.

Figures 13A, 13B:
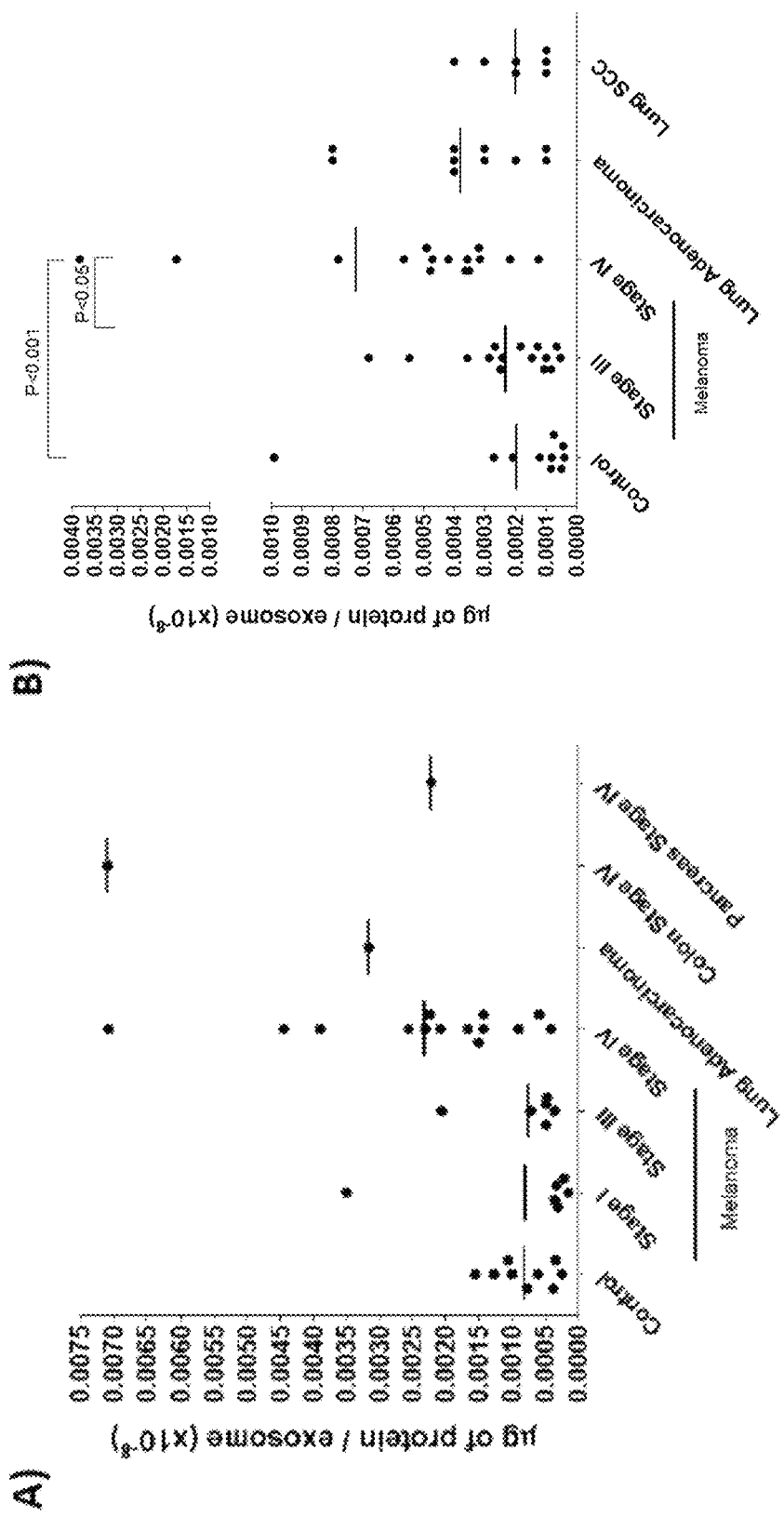

FIGS. 13A-13B are graphs showing protein per exosome in exosomes isolated from plasma of patients having lung adenocarcinoma (FIGS. 13A and 13B), Stage IV colon cancer (FIG. 13A), Stage IV pancreatic cancer (FIG. 13A), and lung squamous cell carcinoma (SCC) (FIG. 13B). The amount of protein per exosome in exosomes isolated from plasma of patients having Stage I, III, and IV melanoma and healthy donors is also shown as a reference.

Figure 14A:
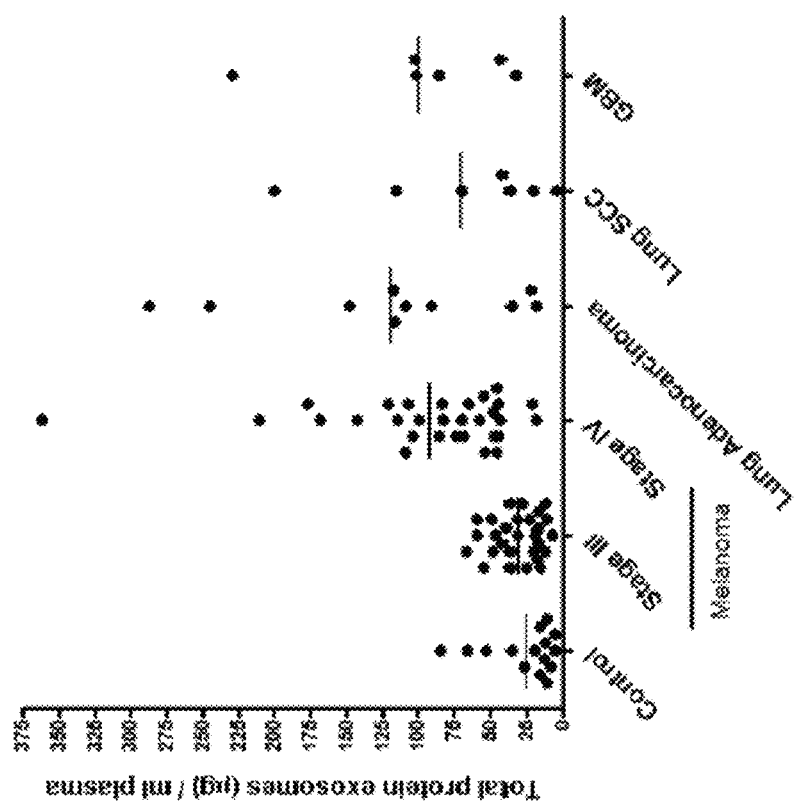
Figure 14B:
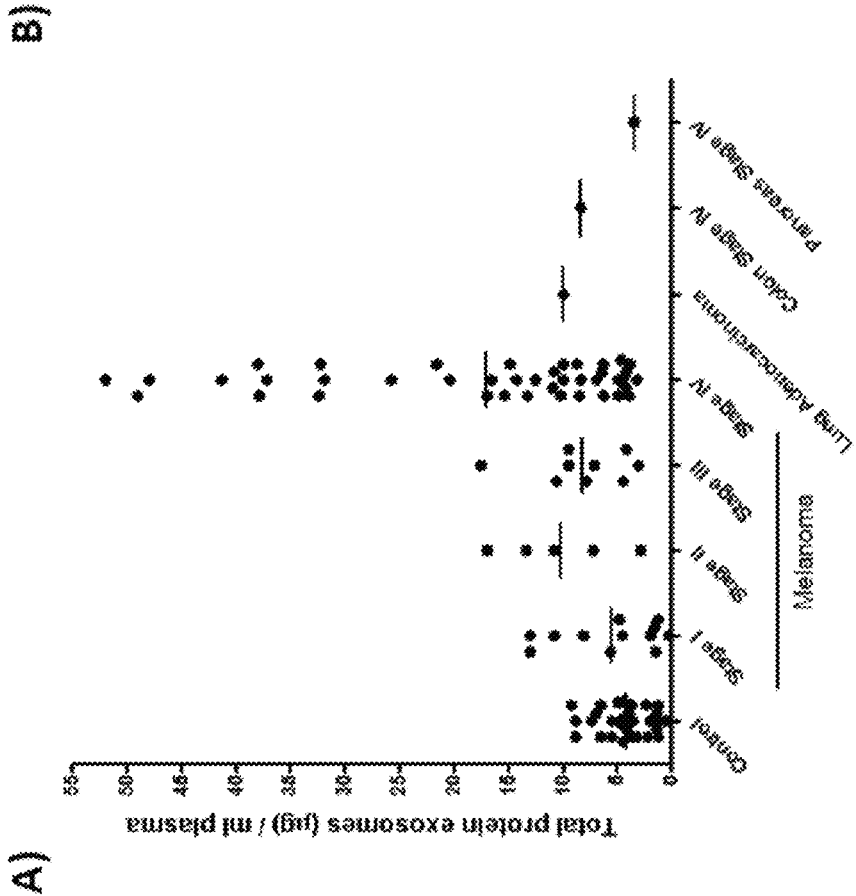

FIGS. 14A-14B are graphs showing protein per milliliter plasma in exosomes isolated from various cancer patients, including patients having lung adenocarcinoma (FIGS. 14A and 14B), Stage IV colon cancer (FIG. 14A), Stage IV pancreatic cancer (FIG. 14A), and lung SCC and glioblastoma multiforme (GBM) (FIG. 14B). The amount of protein per milliliter in exosomes isolated from plasma of patients having Stage I, II, III, and IV melanoma and healthy donors is also shown as a reference.

Figures 15A, 15B:
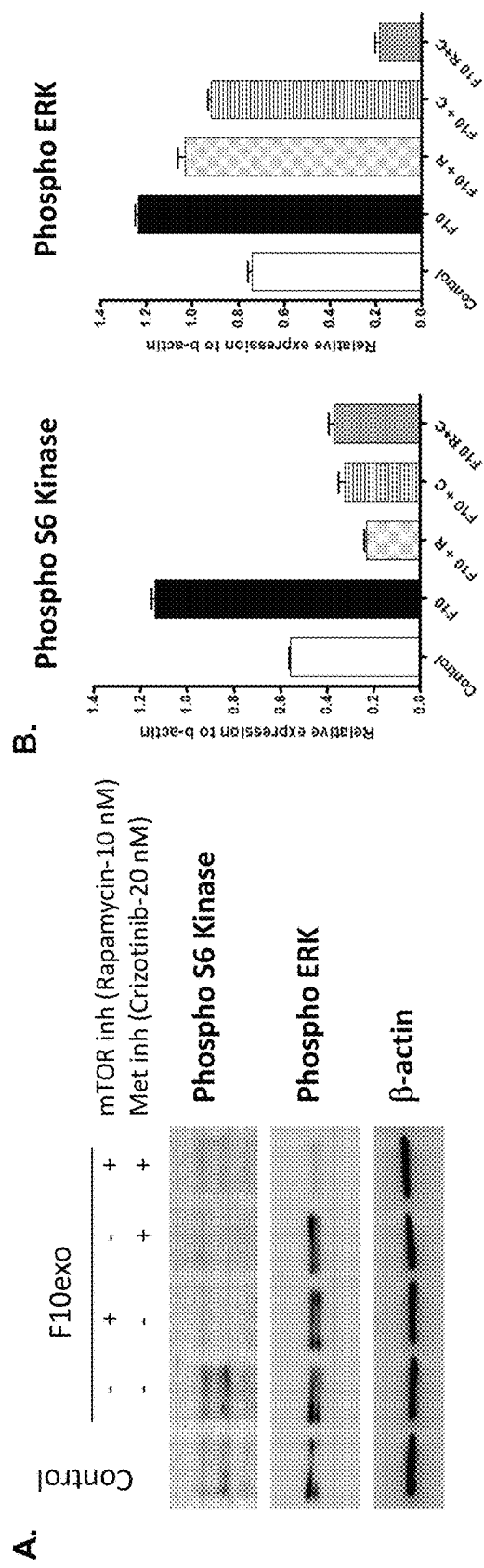

FIGS. 15A-15B show MET inhibition of exosome induced activation of MET signaling. FIG. 15A shows a western blot analysis of phospho-S6 kinase and phospho-ERK in BM cells pre-treated with 20 mg/ml of B16-F10 and B16-F1 exosomes for 16 h, followed by treatment with mTOR (rapamycin) and/or MET inhibitor, Crizotinib, and then stimulated with HGF (5 ng ml-1) for 4 h. β-actin was used as loading control. Quantification of the western blot results are shown in the graphs of FIG. 15B.

FIG. 16 is a table of the differentially expressed genes in mouse lungs after 24 and 48 hours of B16-F10-exosome tail vein injection (red shaded=increased expression (>2 fold), green shaded=decreased expression (>2 fold).

DETAILED DESCRIPTION OF THE INVENTION

A first aspect of the present invention is directed to a method of inhibiting metastatic disease progression in a subject. This method involves selecting a subject having metastatic disease and administering, to the selected subject, an agent that inhibits primary cancer cell exosomes under conditions effective to inhibit metastatic disease progression in the subject.

Another aspect of the present invention is directed to a method of inhibiting pre-metastatic niche formation in a subject. This method involves selecting a subject at risk for metastatic disease and administering to the subject, an agent that inhibits primary cancer cell exosomes under conditions effective to inhibit pre-metastatic niche formation in the subject.

In accordance with these aspects of the invention, metastatic disease encompasses any disease that spreads from one organ or site in the body, i.e., the primary site of disease, to another organ or site in the body. Typically, metastatic disease is one that spreads from a primary organ or site to another, non-adjacent, organ or site in the body. Metastatic disease typically involves, but is not limited to, the spread of malignant tumor or cancer cells from the primary tumor site (i.e., primary cancer cells) to another site in the body. Virtually all cancers have the potential to metastasize. Accordingly, a subject at risk for metastatic disease is any subject having a primary tumor.

The metastases may occur to any site, however some cancers preferentially metastasize to particular organs. For example, lung, breast, head and neck, cervical, and bladder tumors frequently metastasize to particular organs. Specifically, lung cancer metastasizes to brain, bone, liver, adrenal glands, pleura, subcutaneous tissue, kidney, lymph nodes, cerebrospinal fluid, pancreas, and bone marrow. Breast cancer metastasizes to lymph nodes, breast, abdominal viscera, lungs, bones, liver, adrenal glands, brain, meninges, pleura, cerebrospinal fluid. Head and neck cancer metastasizes to lung, esophagus, upper digestive tracts, lymph nodes, oral and nose cavity. Cervical cancer metastasizes to bladder, rectum, pelvic wall, lymph nodes, and paracervical spaces. Bladder cancer metastasizes to the prostate, uterus, vagina, bowel, pelvic wall, lymph nodes, and perivesical fat.

The methods of the present invention are suitable for the treatment of any type of metastatic disease. Metastatic diseases particularly suitable for treatment in accordance with the methods of the present invention include, without limitation, metastatic melanoma, metastatic breast cancer, metastatic brain cancer, metastatic pancreatic cancer, metastatic ovarian cancer, metastatic colorectal cancer, metastatic prostate cancer, metastatic lung cancer, metastatic liver cancer, metastatic renal cancer, and metastatic pediatric cancers (e.g., medulloblastoma).

Another aspect of the present invention is directed to a method of inhibiting primary tumor growth in a subject. This method involves selecting a subject having a primary tumor and administering to the subject, an agent that inhibits primary tumor cell exosomes under conditions effective to inhibit primary tumor growth in the subject As used herein, a "subject" or "patient" encompasses any animal, but preferably a mammal. More preferably, the subject or patient is a human. In all aspects of the invention, a subject or patient is selected for treatment based on their risk of developing metastatic disease, having metastatic disease, or their suitability for responding to an agent that inhibits primary tumor cell exosomes. Accordingly, in one embodiment of the invention selecting a suitable subject involves measuring the exosome level in a sample obtained from the subject (e.g., a blood or plasma sample). As used herein "exosome level" is used generically to encompass a number of different exosome measurements, including, without limitation, the total number of exosomes (e.g., total exosomes per mL plasma), total exosome protein (i.e., total protein per exosome or total exosome protein per mL patient plasma), total exosome DNA or RNA (i.e., total DNA and/or RNA per exosome or total exosome DNA and/or RNA per mL patient plasma), total exosome small RNA, or any combination thereof in a sample. Methods for isolating and purifying exosomes from a blood or plasma sample for measuring the exosome level are described in more detail herein in the Examples. The measured exosome level in the sample is compared to a corresponding reference exosome level, e.g., the average exosome level in one or more samples from healthy, cancer free subjects, or an exosome level measured in a sample from the subject that was obtained at an earlier timepoint. A subject having an elevated exosome level compared to the reference exosome level is a subject at risk of developing metastatic disease, already has metastatic disease, or has a primary tumor and is a suitable candidate for treatment with an agent that inhibits primary tumor cell exosomes.

In another embodiment, selection of a suitable subject for treatment in accordance with the methods of the present invention involves obtaining an exosomal sample from the subject and measuring the exosome expression level of one or more proteins. Methods for isolating and purifying exosomes from a blood or plasma sample for measuring exosome protein expression levels are described in the Examples infra. In one embodiment of the invention, the one or more measured proteins is selected from the group consisting of MET, TYRP2, VLA-4, Hsp-90, Hsp-70, or any combination thereof. Suitable methods for detecting protein expression levels in a sample are known in the art, including, e.g., western blot, immunoprecipitation, enzyme-linked immunosorbent assay (ELISA), radioimmunoassay (RIA), or fluorescent activated cell sorting (FACS). The measured exosomal expression level from the subject's sample is compared to reference exosomal expression levels of the corresponding one or more proteins. A subject having an increase in exosomal expression of any one or more of the measured proteins indicates the subject is at risk for developing metastatic disease, already has metastatic disease, or has a primary tumor and is a suitable candidate for treatment with an agent that inhibits primary tumor cell exosomes. In accordance with this embodiment of the invention, a reference exosomal protein level can be the average exosomal expression level of the one or more proteins in one or more samples obtained from healthy, cancer-free individuals. Alternatively, the reference exosomal protein expression level can be the exosomal protein expression level in a sample from the subject that was obtained at one or more earlier timepoints.

In yet another embodiment, selection of a suitable subject for treatment in accordance with the methods of the present invention involves obtaining a sample from the subject that contains bone marrow derived progenitor cells (BMDCs), e.g., a blood sample, and measuring the MET expression level in the BMDCs of the sample. Exemplary methods of isolating BMDCs from a blood or plasma sample are described in detail infra in the Examples, and methods of measuring MET expression level include any of the suitable methods for measuring protein expression levels disclosed supra. The BMDCs are preferably CD45⁻CD117$^{low/+}$ or CD45⁻CD117$^{low/+}$TIE2⁺ bone marrow progenitor cells. A subject having increased MET expression level in the BMDCs compared to a reference level of MET expression in BMDCs is a subject that is at risk for developing metastatic disease, already has metastatic disease, or has a primary tumor and is a suitable candidate for treatment with an agent that inhibits primary tumor cell exosomes. In accordance with this embodiment of the present invention, a reference MET expression level in BMDCs can be the average MET expression level in BMDCs from one or more samples obtained from healthy, cancer-free individuals. Alternatively, the reference MET expression level can be the MET expression level in BMDCs in a sample from the subject that was obtained at one or more earlier timepoints.

The agent that is administered to the subject in accordance with these aspects of the present invention is an agent that inhibits primary cancer or primary tumor cell exosome production, secretion, and/or activity. As described herein, exosomes are small vesicles (30-100 nm) derived from the luminal membranes of late endosomes/multivesicular bodies (MVB) that are constitutively released via the fusion of MVBs with the cell membrane. Exosomes differ from microvesicles or shedding vesicles, which represent a heterogenous population of extracellular vesicles (<1000 nm) which bud directly from the cell membrane upon activation by different stimuli (Cocucci et al., "Shedding Microvesicles: Artefacts No More," *Trends Cell. Biol.* 19(2):43-51 (2009), which is hereby incorporated by reference in its entirety). As described herein, applicants have found that highly metastatic tumor cells secrete an increased number of exosomes compared to less metastatic cancer cells. These tumor derived exosomes carry tumor proteins, DNA, RNA, and microRNA. In addition, these tumor derived exosomes induce vascular leakiness at pre-metastatic sites and promote bone-marrow derived cell mobilization, enhancing both primary tumor growth and metastasis Inhibition of tumor derived exosomes prevents bone-marrow mobilization and inhibits primary tumor growth and metastasis.

Accordingly, in one embodiment of the present invention, an agent that inhibits primary cancer cell exosome production and/or secretion is administered to a subject at risk of metastatic disease, a subject having a primary tumor, or a subject having metastatic disease. Suitable agents for inhibiting exosome secretion include, without limitation, Ras-related (Rab) protein inhibitors. Rab proteins are members of the Ras superfamily of small GTPases that are involved in regulating membrane trafficking pathways. The 64 known Rab genes are listed in Table 1 below by NCBI Accession number and Reference ID number which are hereby incorporated by reference in their entirety. Like other regulatory GTPases, Rab proteins switch between a GTP-bound conformation and a GDP-bound conformation. In the GTP-bound form, Rab proteins recruit effector proteins and regulate vesicle formation, actin- and tubulin-dependent vesicle movement, and membrane fusion (see Stenmark et al., "The Rab GTPase Family," *Genome Biol.* 2(5):reviews3007.1-3007.7 (2001), which is hereby incorporated by reference in its entirety). As described herein, applicants have discovered Rab protein expression in primary tumor cells induces exosome production and/or secretion. Inhibition of exosome production and/or secretion using one or more Rab inhibitors prevents pre-metastatic niche formation, inhibit metastatic disease progression, and inhibits primary tumor growth.

Suitable Rab inhibitors of the invention may be selective, i.e., targeted inhibition of any one particular Rab protein, or non-selective, i.e., inhibiting one or more Rab proteins in combination. Rab inhibitors of the invention may inhibit any or more of the Rab proteins listed in Table 1. In one embodiment of the invention, the Rab inhibitor is a Rab27a inhibitor, a Rab5b inhibitor, a Rab7 inhibitor, a Rab1a inhibitor, or any combination thereof. Suitable inhibitors of Rab proteins include inhibitory nucleic acid molecules, proteins, peptides, or antibody inhibitors, or small molecule inhibitors.

Inhibitory nucleic acid molecules include, without limitation, antisense molecules, siRNA molecules, shRNA molecules, and microRNA molecules.

siRNA can be used to decrease the cellular or nuclear concentration and activity of the target Rab. siRNAs are double stranded synthetic RNA molecules approximately 20-25 nucleotides in length with short 2-3 nucleotide 3' overhangs on both ends. The double stranded siRNA molecule represents the sense and anti-sense strand of a portion of the target mRNA molecule, in this case a portion of the target Rab nucleotide sequence (e.g., Rab27a). siRNA molecules are typically designed to target a region of the mRNA target approximately 50-100 nucleotides downstream from the start codon. Upon introduction into a cell, the siRNA complex triggers the endogenous RNA interference (RNAi) pathway, resulting in the cleavage and degradation of the target mRNA molecule. Any siRNA molecules known in the art that effectively interfere with Rab expression, particularly Rab27a expression, are suitable for use in the present invention. Since the nucleotide sequences encoding the various Rab proteins are known in the art (see Table 1), suitable siRNA molecules targeting any one of these Rab proteins can be designed using techniques readily known in the art.

TABLE 1

Rab Genes and their Potential Involvement in Cancer

| | Approved Symbol | Potential Cancer Type | Previous Symbols | Aliases | Chromosome | Accession Numbers | RefSeq IDs |
|---|---|---|---|---|---|---|---|
| 1 | RAB1A | tongue cancer, melanoma | RAB1 | YPT1 | 2p14 | M28209 | NM_004161 |
| 2 | RAB1B | | | | 11q13.1 | AJ245875 | NM_030981 |
| 3 | RAB1C | | | | 9p13.1 | | |
| 4 | RAB2A | | RAB2 | | 8q12.1 | | |
| 5 | RAB2B | | | FLJ14824 | 14q11.1 | AK027730 | |

TABLE 1-continued

Rab Genes and their Potential Involvement in Cancer

| | Approved Symbol | Potential Cancer Type | Previous Symbols | Aliases | Chromosome | Accession Numbers | RefSeq IDs |
|---|---|---|---|---|---|---|---|
| 6 | RAB3A | | | | 19p13.2 | | NM_002866 |
| 7 | RAB3B | | | | 1p32-p31 | BC005035 | NM_002867 |
| 8 | RAB3C | | | | 5q13 | AY026936 | NM_138453 |
| 9 | RAB3D | | GOV | RAB16, D2-2, RAD3D | 19p13.2 | AF081353 | NM_004283 |
| 10 | RAB4A | | RAB4 | HRES-1/RAB4 | 1q42-q43 | BC004309 | NM_004578 |
| 11 | RAB4B | | | FLJ78649, MGC52123 | 19q13.2 | AF165522 | NM_016154 |
| 12 | RAB5A | Lung cancer, thyroid | RAB5 | | 3p24-p22 | | NM_004162 |
| 13 | RAB5B | Melanoma | | | 12q13 | | |
| 14 | RAB5C | | RABL | RAB5CL | 17q21.2 | U18420 | NM_004583 |
| 15 | RAB6A | Breast Cancer | RAB6 | | 11q13.3 | AF130986 | |
| 16 | RAB6B | | | | 3q22.1 | AF166492 | |
| 17 | RAB6C | Breast Cancer | | WTH3 | 2q21.1 | AF124200 | NM_032144 |
| 18 | RAB7A | Thyroid, melanoma | RAB7 | | 3q21 | X93499 | |
| 19 | RAB7B | | | MGC9726, MGC16212 | 1q32 | AY094596 | NM_177403 |
| 20 | RAB8A | Melanoma | MEL | RAB8 | 19p13.2-p13.1 | | NM_005370 |
| 21 | RAB8B | | | | 15q22 | AL833365 | NM_016530 |
| 22 | RAB9A | | RAB9 | | Xp22.2 | U44103 | NM_004251 |
| 23 | RAB9B | | | RAB9L | Xq22.1-q22.3 | AB036693 | |
| 24 | RAB9BP1 | | RAB9P1 | | 5q21.2 | U44105 | |
| 25 | RAB10 | | | | 2p23.3 | AF106681 | NM_016131 |
| 26 | RAB11A | esophageal adenocarcinoma | | YL8 | 15q22.31 | X56740 | |
| 27 | RAB11B | | | H-YPT3 | 19p13.2 | X79780 | |
| 28 | RAB12 | | | | 18p11.22 | | XM_113967 |
| 29 | RAB13 | | | | 1q21.2 | X75593 | NM_002870 |
| 30 | RAB14 | | | FBP, RAB-14 | 9q32-q34.11 | AF152463 | NM_016322 |
| 31 | RAB15 | | | | 14q23.2 | BC014511 | NM_198686 |
| 32 | RAB17 | | | | 2q37.3 | AK022600 | |
| 33 | RAB18 | | | | 10p12 | AJ277145 | NM_021252 |
| 34 | RAB20 | | | FLJ20429 | 13q34 | AK000436 | NM_017817 |
| 35 | RAB21 | | | KIAA0118 | 12q15 | AF091035 | |
| 36 | RAB22A | | | | 20q13 | AF091034 | |
| 37 | RAB23 | Hepatocellular carcinoma | | | 6p12.1 | AB034244 | |
| 38 | RAB24 | | | | 5q35.3 | AF087904 | NM_130781 |
| 39 | RAB25 | Ovarian and Breast | | CATX-8 | 1q22 | AF083124 | |
| 40 | RAB26 | Pancreas | | | 16p13.3 | AB027137 | |
| 41 | RAB27A | Melanoma | | RAB27, RAM, GS2, HsT18676 | 15q15-q21.1 | U38654 | NM_004580, NM_183236 |
| 42 | RAB27B | Pancreas | | | 18q21.2 | U57093 | NM_004163 |
| 43 | RAB28 | | | | 4p16.1 | X94703 | |
| 44 | RAB30 | | | | 11q12-q14 | U57092 | NM_014488 |
| 45 | RAB31 | erithroleukemia | | Rab22B | 18p11.3 | U59877 | |
| 46 | RAB32 | colon cancer, gastric cancer | | | 6q24.2 | U71127 | NM_006834 |
| 47 | RAB33A | | | RabS10 | Xq26 | D14889 | NM_004794 |
| 48 | RAB33B | | | DKFZP434G099 | 4q28 | AF350420 | NM_031296 |
| 49 | RAB34 | | | RAB39, RAH | 17q11.2 | AF322067 | NM_031934 |
| 50 | RAB35 | | | H-ray | 12q24 | X79781 | |
| 51 | RAB36 | Rhabdoid tumors | | | 22q11.22 | AB023061 | NM_004914 |
| 52 | RAB37 | | | | 17q25.2 | BC040547 | NM_175738 |
| 53 | RAB38 | | | NY-MEL-1 | 11q14 | AF235022 | |
| 54 | RAB39 | | | | 11q22-q23 | X99962 | NM_017516 |
| 55 | RAB39B | | | | Xq28 | AY052478 | NM_171998 |
| 56 | RAB40A | | | RAR2A, Rar-2 | Xq22.1 | AF132748 | |
| 57 | RAB40B | | | SEC4L, RAR | 17q25.3 | U05227 | |
| 58 | RAB40C | | RASL8C | RARL | 16p13.3 | Z84779 | NM_021168 |
| 59 | RAB41 | | | | Xq13.1 | | XM_293398 |
| 60 | RAB42 | | | MGC45806 | 1p35.3 | BC033175 | NM_152304 |
| 61 | RAB42P1 | | RAB42, RAB42P | | 14q32.11 | | NG_009574 |
| 62 | RAB43 | | | RAB41, RAB11B, ISY1 | 3q21.3 | AY166852 | XM_290714 |
| 63 | RAB43P1 | | RAB43P | RAB41P | 16q11.2 | | NG_005358 |
| 64 | RAB44 | | RASD3, RASL13 | dJ431A14.3 | 6p21.31-p21.2 | | |

Various improvements of siRNA compositions, such as the incorporation of modified nucleosides or motifs into one or both strands of the siRNA molecule to enhance stability, specificity, and efficacy, have been described and are suitable for use in accordance with this aspect of the invention (see e.g., WO2004/015107 to Giese et al.; WO2003/070918 to McSwiggen et al.; WO1998/39352 to Imanishi et al.; U.S. Patent Application Publication No. 2002/0068708 to Jesper et al.; U.S. Patent Application Publication No. 2002/0147332 to Kaneko et al; U.S. Patent Application Publication No. 2008/0119427 to Bhat et al., which are hereby incorporated by reference in their entirety).

Suitable delivery vehicles (e.g., nanoparticles, liposomes, etc.) for the delivery of siRNA and other nucleic acid Rab inhibitors of the invention are described infra.

Short or small hairpin RNA molecules are similar to siRNA molecules in function, but comprise longer RNA sequences that make a tight hairpin turn. shRNA is cleaved by cellular machinery into siRNA and gene expression is silenced via the cellular RNA interference pathway. As demonstrated infra in the Examples, Rab27a shRNA is an effective means for inhibiting Rab27a activity and subsequently inhibiting primary tumor cell exosome secretion. shRNA molecules that effectively interfere with human Rab expression have been developed and are available commercially (e.g., ThermoFischer, human shRNA clones ID-Cat#VGH5523-101066326, ID-Cat#VGH5523-101066811, which are hereby incorporated by reference in their entirety). These shRNA molecules are suitable for use in the methods of the present invention (see also Ostrowski et al., "Rab27a and Rab27b Control Different Steps of the Exosome Secretion Pathway," *Nat. Cell Biol.* 12:19-30 (2009), which is hereby incorporated by reference in its entirety).

As an alternative to siRNA or shRNA, antisense nucleic acid molecules capable of hybridizing with an RNA transcript coding for a target Rab protein are suitable for use in the methods of the present invention. Antisense nucleic acid molecules are expressed from a transgene which is prepared by ligation of a DNA molecule, coding for the target Rab protein, or a fragment or variant thereof, into an expression vector in reverse orientation with respect to its promoter and 3' regulatory sequences. Upon transcription of the DNA molecule, the resulting RNA molecule will be complementary to the mRNA transcript coding for the actual protein or polypeptide product. Ligation of DNA molecules in reverse orientation can be performed according to known techniques which are standard in the art. As discussed infra, recombinant molecules including an antisense sequence or oligonucleotide fragment thereof, may be directly introduced into cells of tissues in vivo using delivery vehicles such as retroviral vectors, adenoviral vectors and DNA virus vectors. They may also be introduced into cells in vivo using physical techniques such as microinjection and electroporation or chemical methods such as coprecipitation and incorporation of DNA into liposomes.

Other agents suitable for use in the methods of the present invention to reduce exosome release include inhibitors of microtubules movements (e.g., taxol), inhibitors of ceramide synthesis (e.g., neutral sphingomyelinase inhibitors such as GW 4869), golgi-ER transport inhibitors (e.g., brefeldin), mTORinhibitors, and Hsp90/Hsp70 inhibitors.

In another embodiment of the present invention, the agent inhibits primary cancer cell exosome activity. As described herein, applicants have found that primary tumor cell exosomes in circulation communicate with bone-marrow derived cells (BMDC) via the MET receptor to promote a pre-metastatic niche formation. Specifically, tumor derived exosomes promote a pro-vasculogenic phenotype in bone marrow-derived cells, increasing their mobilization and recruitment to tumor and metastatic disease sites. Inhibition of this activity prevents pre-metastatic niche formation and inhibits the progression of metastatic disease. In accordance with this aspect of the invention, suitable agents for inhibiting primary cancer cell exosome activity include agents that reduce, block, inhibit or prevent exosome cross-talk with BMDCs. Preferably, the agent neutralizes the primary tumor cell exosomes by aggregating these vesicles and affecting their clearance. Suitable agents for blocking exosome interaction with BMDC are MET inhibitors including, for example, Met biologic inhibitors. A number of MET biologic inhibitors suitable for use in the methods of the present invention are known in the art, including, for example, the U1 ribozyme (see Abounader et al., "Reversion of Human Glioblastoma Malignancy by U1 Small Nuclear RNA/Ribozyme Targeting of Scatter Factor/Hepatocyte Growth Factor and c-Met Expression," *J. Natl. Cancer Inst.* 91:1548-56 (1999) and Herynk et al., "Down-Regulation of c-Met Inhibits Growth in the Liver of Human Colorectal Carcinoma Cells," *Cancer Res.* 63:2990-96 (2003), which are hereby incorporated by reference in their entirety); a dominant-negative Met receptor (see Kaplan et al., "HGF/SF Activates Glycolysis and Oxidative Phosphorylation in DA3 Murine Mammary Cancer Cells," *Neoplasia* 2:365-77 (2000) and Webb et al., "Evidence for a Role of Met-HGF/SF During Ras-Mediated Tumorigenesis/Metastasis," *Oncogene* 17:2019-25 (1998), which are hereby incorporated by reference in their entirety), membrane permeable inhibitory MET peptides (see Bardelli et al., "Uncoupling Signal Transducers from Oncogenic MET Mutants Abrogates Cell Transformation and Inhibits Invasive Growth," *Proc. Natl. Acad. Sci. USA* 95:14379-83 (1998) and Atabey et al., "Potent Blockade of Hepatocyte Growth Factor-Stimulated Cell Motility, Matrix Invasion and Branching Morphogenesis by Antagonists of Grb2 Src Homology 2 Domain Interactions," *J. Biol. Chem.* 276: 14308-14314 (2001), which are hereby incorporated by reference in their entirety). Other suitable MET inhibitors include Met antagonist antibodies (Zheng et al., "A Chimeric Fab Antibody Serves as an Antagonist to the HGF/SF Receptor c-Met," *Proc. Am. Assoc. Cancer Res.* 43:5717 (2003); Morton et al., "In vitro and In vivo Activity of Fully Human Monoclonal Antibody Antagonists to c-Met Protein Tyrosine Kinase," *Proc. Am. Assoc. Cancer Res.* 43:5604 (2003); and Schwall et al., "Inhibition of cMet Activation by a One-Armed Antibody," *Proc. Am. Assoc. Cancer Res.* 44:1424 (2004), which are hereby incorporated by reference in their entirety), and selective small molecule inhibitors of c-Met, such as ATP-competitive c-Met inhibitors defined by an indolin-2-one core structure, e.g., PHA665752, SU11274, SU11271, SU11606, and Kirin (see Christensen et al., "A Selective Small Molecule Inhibitor of c-Met Kinase Inhibits c-Met-Dependent Phenotypes In Vitro and Exhibits Cytoreductive Antitumor Activity In Vivo," *Cancer Res.* 63:7345-55 (2003); Wang et al., "Potent and Selective Inhibitors of the Met [Hepatocyte Growth Factor/Scatter Factor (HGF/SF) Receptor] Tyrosine Kinase Block HGF/SF-Induced Tumor Cell Growth and Invasion," *Mol. Cancer Ther.* 2:1085-1092 (2003); and WO2003000660 to Yasunari et al., which are hereby incorporated by reference in their entirety. Another small molecule MET inhibitor suitable for use in the present invention is Xalkori® (Crizotinib).

Other suitable agents for blocking exosome activity include exosome specific antibodies or binding fragments thereof. These antibodies may exist in a variety of forms including, for example, polyclonal antibodies, monoclonal antibodies, antibody fragments (e.g., Fv, Fab and F(ab)$_2$), as well as single chain antibodies (scFv), chimeric antibodies and humanized antibodies. Methods of making exosome specific antibodies are disclosed in U.S. Patent Publication No. 2009/0148460 to Delcayre et al., which is hereby incorporated by reference in its entirety.

In accordance with the methods of the present invention, administering an agent to a subject to inhibit primary tumor or primary cancer cell exosomes can be done concurrently with other therapeutic approaches, i.e., the agent is administered as part of a combination therapy. Accordingly, in one embodiment of the invention, the agent is administered in combination with one or more additional inhibitors of metastatic disease progression, such as, a chemotherapeutic, radiation (e.g., external beam radiation therapy or brachytherapy), anti-angiogenic therapeutic, a premetastatic niche formation inhibitor, a stromal inhibitor, a bone-marrow derived cell inhibitor, a myeloid derived suppressor cell inhibitor, and extracellular matrix protein inhibitors.

Suitable chemotherapeutic agents for combination therapies include, without limitation, alkylating agents (e.g., chlorambucil, cyclophophamide, CCNU, melphalan, procarbazine, thiotepa, BCNU, and busulfan), antimetabolites (e.g., methotraxate, 6-mercaptopurine, and 5-fluorouracil), anthracyclines (e.g., daunorubicin, doxorubicin, idarubicin, epirubicin, and mitoxantrone), antitumor antibiotics (e.g., bleomycin, monoclonal antibodies (e.g., Alemtuzumab, Bevacizumab, Cetuximab, Gemtuzumab, Ibritumomab, Panitumumab, Rituximab, Tositumomab, and Trastuxmab), platiniums (e.g., cisplatin and oxaliplatin) or plant alkaloids (e.g., topoisomerase inhibitors, vinca alkaloids, taxanes, and epipodophyllotoxins).

Anti-angiogenic or anti-vasculogenic therapeutics suitable for use in combination with an exosome inhibitor of the invention include, without limitation a vascular endothelial growth factor (VEGF) inhibitor, basic fibroblast growth factor (bFGF) inhibitor, vascular endothelial growth factor receptor (VEGFR) antagonist, platelet-derived growth factor receptor (PDGFR) antagonist, fibroblast growth factor receptor (FGFR) antagonist, Angiopoietin receptor (Tie-2) antagonist, epidermal growth factor receptor (EGFR, ErbB) antagonist, or any combination thereof. A number of suitable small molecule angiogenic inhibitors are known in the art and are under clinical development (see e.g., Wu et al., "Anti-Angiogenic Therapeutic Drugs for the Treatment of Human Cancer," *J Cancer Molecules* 4(2):37-45 (2008) and Bissell et al., "Why Don't We Get More Cancer? A Proposed Role of the Microenvironment in Restraining Cancer Progression," *Nat. Med.* 17(3):320-329 (2011), which are hereby incorporated by reference in their entirety). These angiogenic inhibitors include, without limitation, Endostatin (an endothelial cell proliferation and angiogenesis inhibitors), Gefitinib (an ErbB inhibitor), Lapatinib (a dual ErbB1/ErbB2 inhibitor), Erlotinib (HER1/EGFR inhibitor), Canertinib (a pan-ErbB inhibitor), Vatalanib (VEGF receptor inhibitor), Imatinib (multi-targeted inhibitor of Bcr-Abl, c-kit, and PDGF-R inhibitor), Sunitinib (multi-targeted inhibitor of VEGFR, PDGFR, Kit, Flt3, Tet and CSF1R), Sorafenib (multi-targeted inhibit of VEGFR and PDGFR), Pazopanib (a multi-targeted inhibitor of VEGFR-1, VEGFR-2, VEGFR-3, PDGF-α, PDGFR-β, and c-kit). Alternatively, the anti-vasculogenic therapeutic is a monoclonal antibody. Suitable antibody therapeutics include, without limitation, Bevacizumab (VEGF antibody), IMC-1C11 (VEGFR-2 antibody), mF4-31C1 (VEGFR-3 antibody), and Vitaxin (integrin $α_vβ_3$ antibody).

Suitable stromal inhibitors for use in the present invention are known in the art (see Bissell et al., "Why Don't We Get More Cancer? A Proposed Role of the Microenvironment in Restraining Cancer Progression," *Nat. Med.* 17(3):320-329 (2011), which is hereby incorporated by reference in its entirety) and include, without limitation, MK-2461 (a small molecule inhibit of c-MET kinase), Anastrazole (an aromatase inhibitor), AMD070 (a CXCR4 inhibitor), IPI-926 (a hedgehog pathway inhibitor), AVE1642 (a humanized monoclonal antibody targeting insulin-like growth factor-1 receptor), BGJ398 (a small molecule inhibitor of fibroblast growth factor receptors), Celecoxib (a COX-2 inhibitor), MK0822 (a cathepsin K inhibitor), Bortezomib (a 26S proteasome complex inhibitor), Zoledronate (a small-molecule pyrophosphate analog that inhibits the differentiation of myeloid cells and affects tumor-associated macrophages), Denosumab (a human monoclonal antibody the binds RANKL), and PG545, a heparan sulfate mimetic that inhibits heparanase activity.

Suitable premetastatic niche formation inhibitors includes, without limitation, bone-marrow derived cell inhibitors (e.g., VEGFR1 inhibitor or CD11b inhibitor), S100a8 inhibitor, S100a9 inhibitors, Lysyl oxidase inhibitor, matrix metalloproteinase-9 and -2 inhibitors (e.g., Incyclinide, PCK3145).

Suitable extracellular matrix protein inhibitors include, without limitation, DX2400, an MMP-14 inhibitor; PEGPH20, a covalently modified form of hyaluronidase which catalyzes the degradation of the extracellular matrix component hyalurona.

Other agents suitable for use in a combination therapy comprising the exosome inhibitors of the present invention are disclosed in Bissell et al., "Why Don't We Get More Cancer? A Proposed Role of the Microenvironment in Restraining Cancer Progression," *Nat. Med.* 17(3):320-329 (2011), which is hereby incorporated by reference in its entirety.

In an alternative embodiment of the invention, the agent is administered as a part of an adjuvant therapy regime. In particular, this involves chemotherapy, hormone therapy, radiation therapy, immunotherapy, or a targeted therapy together with an agent that inhibits primary cell exosomes prior to and/or after surgery. In addition, the present invention may be used to treat patients after primary surgery who may not otherwise receive treatment, i.e. those patients with primary complete resection without evidence of residual or distant disease in order to prevent pre-metastatic niche formation and, therefore, metastatic spread.

Pharmaceutical compositions containing exosome inhibitors suitable for use in the methods of the present invention can include a pharmaceutically acceptable carrier as described infra, one or more active agents, and a suitable delivery vehicle. Suitable delivery vehicles include, but are not limited to viruses, bacteria, biodegradable microspheres, microparticles, nanoparticles, liposomes, collagen minipellets, and cochleates.

In one embodiment of the present invention, the pharmaceutical composition or formulation containing an inhibitory nucleic acid molecule (e.g., siRNA molecule) is encapsulated in a lipid formulation to form a nucleic acid-lipid particle as described in Semple et al., "Rational Design of Cationic Lipids for siRNA Delivery," *Nature Biotech.* 28:172-176 (2010) and International Patent Application Publication Nos. WO2011/034798 to Bumcrot et al., WO2009/111658 to Bumcrot et al., and WO2010/105209 to Bumcrot et al., which are hereby incorporated by reference in their entirety.

In another embodiment of the present invention, the delivery vehicle is a nanoparticle. A variety of nanoparticle delivery vehicles are known in the art and are suitable for delivery of an exosome inhibitor of the invention (see e.g., van Vlerken et al., "Multi-functional Polymeric Nanoparticles for Tumour-Targeted Drug Delivery," *Expert Opin. Drug Deliv.* 3(2):205-216 (2006), which is hereby incorporated by reference in its entirety). Suitable nanoparticles include, without limitation, poly(beta-amino esters) (Sawicki et al., "Nanoparticle Delivery of Suicide DNA for Epithelial Ovarian Cancer Cell Therapy," *Adv. Exp. Med. Biol.* 622:209-219 (2008), which is hereby incorporated by reference in its entirety), polyethylenimine-alt-poly(ethylene glycol) copolymers (Park et al., "Degradable Polyethylenimine-alt-Poly(ethylene glycol) Copolymers As Novel Gene Carriers," *J. Control Release* 105(3):367-80 (2005) and Park et al., "Intratumoral Administration of Anti-KITENIN shRNA-Loaded PEI-alt-PEG Nanoparticles Suppressed Colon Carcinoma Established Subcutaneously in Mice," *J Nanosci. Nanotechnology* 10(5):3280-3 (2010), which are hereby incorporated by reference in their entirety), and liposome-entrapped siRNA nanoparticles (Kenny et al., "Novel Multifunctional Nanoparticle Mediates siRNA Tumor Delivery, Visualization and Therapeutic Tumor Reduction In Vivo," *J. Control Release* 149(2): 111-116 (2011), which is hereby incorporated by reference in its entirety). Other nanoparticle delivery vehicles suitable for use in the present invention include microcapsule nanotube devices disclosed in U.S. Patent Publication No. 2010/0215724 to Prakash et al., which is hereby incorporated by reference in its entirety.

In another embodiment of the present invention, the pharmaceutical composition is contained in a liposome delivery vehicle. The term "liposome" means a vesicle composed of amphiphilic lipids arranged in a spherical bilayer or bilayers. Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

Several advantages of liposomes include: their biocompatibility and biodegradability, incorporation of a wide range of water and lipid soluble drugs; and they afford protection to encapsulated drugs from metabolism and degradation. Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Methods for preparing liposomes for use in the present invention include those disclosed in Bangham et al., "Diffusion of Univalent Ions Across the Lamellae of Swollen Phospholipids," *J. Mol. Biol.* 13:238-52 (1965); U.S. Pat. No. 5,653,996 to Hsu; U.S. Pat. No. 5,643,599 to Lee et al.; U.S. Pat. No. 5,885,613 to Holland et al.; U.S. Pat. No. 5,631,237 to Dzau & Kaneda; and U.S. Pat. No. 5,059,421 to Loughrey et al., which are hereby incorporated by reference in their entirety.

A liposome which containing an exosome inhibitor can be contacted with the target primary cancer cells under conditions effective for delivery of the inhibitory agent into the cancer cell. For administration to a primary tumor site, the liposomal vesicles need not be targeted to the cancer cells per se. However, when it is desirable to inhibit exosome activity, the liposome is designed to target exosomes in circulation (e.g., using an exosome specific antibody).

The liposome and nanoparticle delivery systems can be made to accumulate at a target organ, tissue, or cell via active targeting (e.g., by incorporating an antibody or other ligand on the surface of the delivery vehicle). For example, when the target cell is a cancer cell as in the present invention, delivery vehicle may be conjugated to an anti-C3B(I) antibody as disclosed by U.S. Pat. No. 6,572,856 to Taylor et al., which is hereby incorporated by reference in its entirety. Alternatively, the delivery vehicle may be conjugated to an alphafeto protein receptor as disclosed by U.S. Pat. No. 6,514,685 to Moro, or to a monoclonal GAH antibody as disclosed by U.S. Pat. No. 5,837,845 to Hosokawa, which are hereby incorporated by reference in their entirety.

In another embodiment of the present invention, the delivery vehicle is a viral vector. Viral vectors are particularly suitable for the delivery of inhibitory nucleic acid molecules, such as siRNA or shRNA molecules, but can also be used to deliver nucleic acid molecules encoding an anti-exosome antibody. Suitable gene therapy vectors include, without limitation, adenoviral vectors, adeno-associated viral vectors, retroviral vectors, lentiviral vectors, and herpes viral vectors.

Adenoviral viral vector delivery vehicles can be readily prepared and utilized as described in Berkner, "Development of Adenovirus Vectors for the Expression of Heterologous Genes," *Biotechniques* 6:616-627 (1988) and Rosenfeld et al., "Adenovirus-Mediated Transfer of a Recombinant Alpha 1-Antitrypsin Gene to the Lung Epithelium In Vivo," *Science* 252:431-434 (1991), WO 93/07283 to Curiel et al., WO 93/06223 to Perricaudet et al., and WO 93/07282 to Curiel et al., which are hereby incorporated by reference in their entirety. Adeno-associated viral delivery vehicles can be constructed and used to deliver an inhibitory nucleic acid molecule of the present invention to cells as described in Shi et al., "Therapeutic Expression of an Anti-Death Receptor-5 Single-Chain Fixed Variable Region Prevents Tumor Growth in Mice," *Cancer Res.* 66:11946-53 (2006); Fukuchi et al., "Anti-Aβ Single-Chain Antibody Delivery via Adeno-Associated Virus for Treatment of Alzheimer's Disease," *Neurobiol. Dis.* 23:502-511 (2006); Chatterjee et al., "Dual-Target Inhibition of HIV-1 In Vitro by Means of an Adeno-Associated Virus Antisense Vector," *Science* 258:1485-1488 (1992); Ponnazhagan et al., "Suppression of Human Alpha-Globin Gene Expression Mediated by the Recombinant Adeno-Associated Virus 2-Based Antisense Vectors," *J. Exp. Med.* 179:733-738 (1994); and Zhou et al., "Adeno-associated Virus 2-Mediated Transduction and Erythroid Cell-Specific Expression of a Human Beta-Globin Gene," *Gene Ther.* 3:223-229 (1996), which are hereby incorporated by reference in their entirety. In vivo use of these vehicles is described in Flotte et al., "Stable in Vivo Expression of the Cystic Fibrosis Transmembrane Conductance Regulator With an Adeno-Associated Virus Vector," *Proc. Nat'l. Acad. Sci.* 90:10613-10617 (1993) and Kaplitt et al., "Long-Term Gene Expression and Phenotypic Correction Using Adeno-Associated Virus Vectors in the Mammalian Brain," *Nature Genet.* 8:148-153 (1994), which are hereby incorporated by reference in their entirety. Additional types of adenovirus vectors are described in U.S. Pat. No. 6,057,155 to Wickham et al.; U.S. Pat. No. 6,033,908 to Bout et al.; U.S. Pat. No. 6,001,557 to Wilson et al.; U.S. Pat. No. 5,994,132 to Chamberlain et al.; U.S. Pat. No. 5,981,225 to Kochanek et al.; U.S. Pat. No. 5,885,808 to Spooner et al.; and U.S. Pat. No. 5,871,727 to Curiel, which are hereby incorporated by reference in their entirety.

Retroviral vectors which have been modified to form infective transformation systems can also be used to deliver a nucleic acid molecule to a target cell. One such type of retroviral vector is disclosed in U.S. Pat. No. 5,849,586 to Kriegler et al., which is hereby incorporated by reference. Other nucleic acid delivery vehicles suitable for use in the present invention include those disclosed in U.S. Patent Publication No. 20070219118 to Lu et al., which is hereby incorporated by reference in its entirety.

Regardless of the type of infective transformation system employed, it should be targeted for delivery of the nucleic acid to the desired cell type. For example, for delivery into a cluster of cells (e.g., cancer cells) a high titer of the infective transformation system can be injected directly within the site of those cells so as to enhance the likelihood of cell infection. The infected cells will then express the inhibitory nucleic acid molecule targeting the inhibition of Rab expression. The expression system can further contain a promoter to control or regulate the strength and specificity of expression of the nucleic acid molecule in the target tissue or cell.

To target delivery of an inhibitory Rab nucleic acid molecule to cancer cells, a cancer cell-specific targeting approach is desirable. Suitable cancer cell-specific targeting approaches include the lentivirus-mediated Tet-On inducible system under the control of the matrix metalloproteinase-2 promoter as described by Seo et al., "Induction of Cancer Cell-Specific Death via MMP2 Promoter-Dependent Bax Expression," *BMB Reports* 42(4):217-222 (2009), which is hereby incorporated by reference in it entirety. Also suitable for targeting cancer-specific cells is the dual promoter system described by Fukazawa et al., "Development of a Cancer-Targeted Tissue-Specific Promoter System," *Can. Res.* 64:363-369 (2004), which is hereby incorporated by reference in its entirety, that combines the human telomerase reverse transcriptase promoter (hTERT) and a tissue specific promoter (e.g., prostate-specific antigen (PSA) or promoter for directing prostate cancer cell specific expression or the PRL-3 protein tyrosine phosphatase promoter for colon cancer cell specific expression) to target expression to cancer cells. Other cancer cell-specific targeting approaches utilizing the hTERT tumor-specific promoter are also suitable for use in the present invention (see, e.g., Fang et al., "Development of Chimeric Gene Regulators for Cancer-Specific Gene Therapy with Both Transcriptional and Translational Targeting," *Mol. Biotechnol.* 45:71-81 (2010), Gu et al., "Tumor-Specific Transgene Expression from the Human Telomerase Reverse Transcriptase Promoter Enables Targeting of the Therapeutic Effects of the Bax Gene to Cancers," *Can. Res.* 60:5359-64 (2000), and Gu et al., "A Novel Single Tetracycline-Regulative Adenoviral Vector for Tumor-Specific Bax Gene Expression and Cell Killing In Vitro and In Vivo," *Oncogene* 21:4757-62 (2002), which are hereby incorporated by reference in their entirety).

In practicing the methods of the present invention, the administering step is carried out to achieve inhibition of pre-metastatic niche formation, metastatic disease progression, or primary tumor growth. Such administration can be carried out systemically or via direct or local administration to the tumor site. By way of example, suitable modes of systemic administration include, without limitation orally, topically, transdermally, parenterally, intradermally, intramuscularly, intraperitoneally, intravenously, subcutaneously, or by intranasal instillation, by intracavitary or intravesical instillation, intraocularly, intraarterialy, intralesionally, or by application to mucous membranes. Suitable modes of local administration include, without limitation, catheterization, implantation, direct injection, dermal/transdermal application, or portal vein administration to relevant tissues, or by any other local administration technique, method or procedure generally known in the art. The mode of affecting delivery of agent will vary depending on the type of therapeutic agent (e.g., an antibody or an inhibitory nucleic acid molecule) and the disease to be treated.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

When the exosome inhibitors of the present invention are administered parenterally, solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

Pharmaceutical formulations suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt Effective doses of the compositions of the present invention, for the treatment of a primary tumor or metastatic disease vary depending upon many different factors, including type and stage of cancer, means of administration, target site, physiological state of the patient, other medications or therapies administered, and physical state of the patient relative to other medical complications. Treatment dosages need to be titrated to optimize safety and efficacy.

Another aspect of the present invention is directed to methods of determining the prognosis of a subject having cancer. Prognosis generally refers to a determination of the likely outcome of an illness, in this case cancer. In accordance with this aspect of the invention, prognosis refers to a determination of the metastatic status or metastatic potential of a primary cancer or primary tumor. An unfavorable prognosis predicts the development of metastatic disease, whereas a favorable prognosis indicates metastatic disease is not likely to develop.

In one embodiment of this aspect of the invention, a subject's prognosis is determined by measuring the exosome level in a sample (e.g., a blood or plasma samples) from the subject and comparing the measured exosome level from the sample to a reference exosome level as described supra. As used herein "exosome level" is used generically to encompass a number of different exosome measurements, including, without limitation, the total number of exosomes (e.g. total exosomes per mL plasma), total exosome protein (i.e., total protein per exosome or total exosome protein per mL patient plasma), total exosome DNA or RNA (i.e., total DNA and/or RNA per exosome or total exosome DNA and/or RNA per mL patient plasma), total exosome small RNA, or any combination thereof in a sample. Methods for isolating and purifying exosomes from a blood or plasma sample for measuring the exosome level are described in more detail herein in the Examples. A subject having an increased exosome level compared to the reference exosome level has an unfavorable prognosis, for example, a prognosis of metastatic disease. In a preferred embodiment of the invention, the exosome level is monitored over time in a subject having a primary tumor to monitor primary tumor growth and/or for early detection of pre-metastatic niche formation and/or metastatic disease.

In another embodiment of this aspect of the invention, the subject's prognosis is determined by measuring exosomal expression level of one or more proteins and comparing the measured expression level to reference exosomal expression levels of the one or more proteins as described supra. In one embodiment, the exosomal expression level of MET, TYRP2, VLA-4, Hsp-90, Hsp-70, or any combination there of is measured. An increase in the exosomal expression level of any one or more of these proteins compared to the reference exosomal expression level is indicative of an unfavorable prognosis for the subject.

In another embodiment of this aspect of the invention, the subject's prognosis is determined by measuring the MET expression level in BMDCs from the subject and comparing the measured MET expression level in the sample to a reference MET expression level as described supra. In accordance with this aspect of the invention, the BMDCs are in circulation, and the sample obtained from the subject for prognosis purposes is a peripheral blood samples. As described supra, the BMDCs cells are preferably $CD45^-CD117^{low/+}$ or $CD45^-CD117^{low/+}TIE2^+$ bone marrow progenitor cells. An increase in the MET expression level in BMDCs in the sample from the subject compared to a reference MET expression level indicates an unfavorable prognosis for the subject.

In accordance with this aspect of the invention, an unfavorable prognosis of a subject is a prognosis of metastatic disease or disease progression. Accordingly, regardless of the method employed to determine the subject's prognosis, if an unfavorable prognosis is determined, then the subject's course of treatment is modified to address the prognosis. In a preferred embodiment, the subject's prognosis is determined at an early stage and treatment is modified to prevent the development of metastatic disease or inhibit its progression using the methods and pharmaceutical agents of the invention that inhibit primary tumor exosome activity as described supra. When a favorable prognosis is found (i.e., because the subject does not have an elevated exosome level, elevated exosomal protein expression levels, or elevated MET expression levels) then the course of treatment for the subject does not need to be modified.

Another aspect of the present invention is directed to a method of diagnosing metastatic disease type in a subject. This method involves obtaining an exosomal sample from the subject and detecting one or more biomarkers of metastatic disease type in the sample. The method further involves identifying the metastatic disease type in the subject based on said detecting and administering a therapeutic agent to the subject that is suitable for treating the identified metastatic disease type.

As described herein applicants have discovered that exosomes derived from cancer patients have unique molecular signatures based on the origin of the primary tumor that can be used to diagnose the metastatic disease type. This unique molecular signature is based on exosome protein, DNA, RNA, and/or microRNA content. This method of diagnosing metastatic disease is suitable for diagnosing any metastatic disease type as described supra, including, without limitation, metastatic melanoma, metastatic breast cancer, metastatic brain cancer, metastatic pancreatic cancer, metastatic ovarian cancer, metastatic colorectal cancer, metastatic prostate cancer, metastatic lung cancer, metastatic liver cancer, metastatic renal cancer, and metastatic pediatric cancers.

In one embodiment of this aspect of the present invention, the one or more biomarkers of metastatic disease type are protein biomarkers. In accordance with this embodiment of the invention, the detecting involves measuring the expression level of one or more protein biomarkers of metastatic disease in an exosomal sample from the subject. In accordance with this aspect and other aspects of the invention relating to exosome or BMDCs protein expression levels, suitable methods for measuring protein expression levels in these samples include those commonly used in the art. These methods generally involve contacting the sample with one or more detectable reagents that is suitable for measuring protein expression, e.g., a labeled antibody or a primary antibody used in conjunction with a secondary antibody, and measuring protein expression level based on the level of detectable reagent in the sample after normalizing to total protein in the sample. Suitable methods for detecting protein expression level in an exosome or BMDC sample that are commonly employed in the art include, for example and without limitation, western blot, immunoprecipitation, enzyme-linked immunosorbent assay (ELISA), radioimmunoassay (RIA), or fluorescent activated cell sorting (FACS). The measured protein expression level in the sample is compared to the protein expression level measured in a reference exosomal sample and the type of metastatic disease is identified based on this comparison.

As described herein, exosomes derived from a primary tumor express a unique protein signature that can be used to diagnose or identify the metastatic disease. For example, a diagnosis of metastatic melanoma can be made by assaying the expression level of one or more protein biomarkers selected from the group consisting of MET, TYRP2, VLA-4, Hsp70, and truncated Hsp90. An increase in the expression level of one or more of these proteins in an exosomal fraction of a sample from a subject compared to a reference exosomal expression level of these proteins (i.e., average exosome expression level of proteins from a healthy subject) indicates the subject has metastatic melanoma.

Another aspect of the present invention is directed to identifying the origin of the metastatic disease. This method involves obtaining a metastatic sample from the subject and measuring the expression of one or more ras-related (Rab) proteins in the sample. The measured expression levels of the one or more Rab proteins is compared to the expression levels of the Rab proteins in a reference sample and the origin of the metastatic disease is determined based on this comparison. In one embodiment of the invention, the expression level of one or more Rab proteins selected from the group consisting of Rab27a, Rab5b, Rab7, and Rab1 is measured. An increase in the expression of one or more of these proteins in the sample from the subject compared to the reference sample indicates the metastatic disease originated from melanoma. In accordance with this aspect of the invention, a reference sample is a corresponding non-metastatic tissue derived from the subject being tested or a corresponding tissue sample from a healthy subject, i.e., a subject that does not have cancer.

Another aspect of the invention is directed to a method of monitoring metastatic disease treatment in a subject. This method involves obtaining first and second samples, at different points in time, from the subject being treated for a metastatic disease and measuring the exosome level and/or the exosomal expression levels of one or more protein biomarkers of metastatic disease in each sample. This method further involves comparing the exosome level and/or the exosomal expression levels of the one or more protein biomarkers of metastatic disease in the first sample to corresponding levels in the second sample, and determining whether the subject is responding to the metastatic disease treatment based on this comparison.

In one embodiment of this aspect of the present invention, the first sample is obtained before treatment and the second sample is obtained after treatment. Alternatively, however, both samples can be obtained after one or more treatments; the second sample obtained at some point in time later than the first sample. The treatment being monitored can be any treatment suitable for treating metastatic disease, including, without limitation, chemotherapy, radiation, anti-angiogenic therapy, premetastatic niche formation inhibitor therapy, stromal inhibitor therapy and extracellular matrix protein inhibitor therapy.

A decrease in the exosome level in the second sample compared to the first sample indicates the subject is responding favorably to the metastatic disease treatment. Likewise, an increase or no change in the exosome level in the second sample compared to the first sample indicates the subject is not responding favorably to the metastatic disease treatment. The subject's treatment type and/or dosage is modified to better suit the individual's treatment needs.

Another aspect of the present invention is directed to an in vitro method of identifying candidate compounds useful for inhibiting primary tumor growth or preventing the formation and progression of metastatic disease in a subject. This method involves providing a test compound and contacting the test compound with malignant cells that secrete high levels of exosomes. The method further involves identifying test compounds that inhibit exosome production, secretion, and/or activity, from the malignant cells as candidate compounds useful for inhibiting primary tumor growth or preventing the formation and progression of metastatic disease in a subject.

As described in the Examples infra, the method of identifying candidate compounds for inhibiting tumor growth and preventing the formation and progression of metastatic disease can be performed in vitro. Suitable malignant cells for use in the method include, without limitation, B16-F10 cells, SK-Mel28 cells, and SK-Mel202 cells. In an alternative embodiment of the invention, the method can be carried out in vivo. In accordance with this embodiment, the candidate compound is administered to an animal having a primary tumor. Prior to and following administration of the test compound, samples from the animal (e.g., blood sample) are analyzed for a change in exosome production, secretion, and/or activity. These endpoints can be analyzed in a number of ways, e.g., measuring total exosome secretion, rate of secretion, total exosome protein, RNA, DNA content, and/or effects on BMDC. For example, in the case of melanoma, following administration of a candidate compound, the levels of MET, TYRP2, VLA-4, Hsp70, and Hsp90 expression in an exosomal fraction of a sample obtained from the animal can be assayed. A decrease in the levels of expression of these proteins would indicate a decrease in the malignant exosomes in the sample, thereby identifying a compound suitable for inhibiting tumor growth and preventing the formation and progression of metastatic disease. Alternatively, other endpoints, such as BMDC mobilization and recruitment to a site of metastasis can also be examined as surrogate markers of a compound's effectiveness to inhibit exosome secretion and/or activity.

Another aspect of the invention is directed to an in vivo method of identifying candidate compounds useful for inhibiting primary tumor growth or preventing the formation and progression of metastatic disease in a subject. This method involves providing a test compound and providing an animal model comprising a primary tumor. The method further involves administering to the animal model malignant cell derived exosomes and the test compound, and identifying test compounds which inhibit exosome activity in the animal model as candidate compounds useful for inhibiting primary tumor growth or preventing the formation and progression of metastatic disease in a subject. In accordance with this aspect of the invention, inhibition of exosome activity can be assessed by an analysis of bone-marrow derived cell recruitment to a site of metastasis as described in the Examples herein.

EXAMPLES

The following examples are provided to illustrate embodiments of the present invention but they are by no means intended to limit its scope.

Materials and Methods for Examples 1-6

Exosome Purification and Tracking Analysis.

Cells were cultured in media supplemented with 10% exosome-depleted fetal bovine serum (FBS, Hyclone). FBS was depleted of bovine exosomes by ultracentrifugation at 100,000 g for 70 minutes. Supernatant (SN) fractions collected from 48-72 h cell cultures were pelleted by centrifugation at 500×g for 10 minutes. The supernatant was centrifuged at 20,000×g for 20 minutes. Exosomes were then harvested by spinning at 100,000×g for 70 min. The exosome pellet was resuspended in 20 ml of 1×PBS and collected by ultracentrifugation at 100,000×g for 70 min (Sorvall Surespin 630 rotor). Circulating exosomes from mouse and human plasma were isolated as above with an additional filtration through 1.2 μm nylon filters (GE) before the last step of ultracentrifugation. For centrifugation onto sucrose cushions, the samples were diluted 1/10 in PBS after centrifugation at 20,000×g and then collected by ultracentrifugation (100,000×g for 70 min) on a 40% sucrose cushion. The floating exosome fraction was collected again by ultracentrifugation as above, and the final pellet was resuspended in 100 μl of PBS. For studies with frozen plasma retrospective series 2 ml of cell-free plasma were centrifuged at 500×g for 10 minutes, then supernatant was centrifuged at 20,000×g for 20 minutes. Exosomes were then harvested by spinning at 100,000×g for 70 min. The exosome pellet was resuspended in 2 ml of 1×PBS and collected by ultracentrifugation again at 100,000×g for 70 min (Sorvall S100AT5 rotor). The LM10 nanoparticle characterization system (NanoSight) equipped with a blue laser (405 nm) was used for real-time characterization of the vesicles. The result is presented as the average ±s.e.m.

Electron Microscopy.

Exosomes purified as described above were fixed in 2% w/v paraformaldehyde (PFA) in 200 mM phosphate buffer (pH 7.4). Fixed exosomes were dropped onto a formvar-carbon-coated grid and left to dry at room temperature for 20 min. After washing in 1×PBS, the exosomes were fixed in 1% glutaraldehyde for 5 min, washed again in water, and stained with saturated aqueous uranyl oxalate for 5 min. Samples were then embedded in 0.4% wt/vol uranyl acetate, 1.8% wt/vol methylcellulose and incubated on ice for 10 min. The excess liquid was removed. The grid was dried at room temperature for 10 min and viewed at 20,000× and 50,000× using an electron microscope (model 910; Carl Zeiss, Inc.). Images were recorded on film and subsequently scanned into TIFF format. Images were not subjected to any post-acquisition processing.

Cell Lines and Cell Culture.

B16-F10, B16-F1, LLC, MCF-7, As-Pc1, and MDA-MB-231 cells were cultured in DMEM. SkBr3, SW480, SW620 and human melanoma cells (SK-Mel-#) were cultured in RPMI supplemented with penicillin (100 U/ml) and streptomycin (100 μg/ml) and 10% or 7.5% exosome-depleted (FBS), respectively. Cells were obtained from the ATCC, human melanoma cell lines are obtained from MSKCC and the melan-a cell line was kindly provided by Dr. Dorothy C Bennett, (St. George's University of London) and was grown in RPMI, supplemented with 10% FBS and 200 nM TPA.

Human Studies.

Human peripheral blood samples were obtained from stage I, III or stage IV melanoma patients with histologically-confirmed melanoma and seen at MSKCC. For retrospective plasma studies of circulating exosomes frozen plasma derived from stage III, stage IV and controls was analyzed. Stage III patients were followed up in a range from 1 to 4 years. Stage IV patients were followed up over 42 months. All patients provided informed consent for blood donation on an MSKCC IRB-approved protocol.

Exosome Labeling and Treatment.

5 to 10 μg of total exosome protein were injected by tail vein injection or retro-orbitaly in a total volume of 100-200 μl of PBS. An equal amount of 100 nm synthetic unilamellar liposomes (Encapsula nanoscience) and PBS was used as a control. For exosome-tracking experiments, purified exosomes were fluorescently labeled using PKH67 membrane dye (Sigma) following the commercial protocol. Labeled exosomes were washed in 20 ml of 1×PBS, and collected by centrifugation as above. The final exosome pellet was resuspended in 100-200 μl of PBS. No dye contamination in PKH67-labeled exosomes preparations was verified by ultracentrifugation on 40% sucrose cushions as describe above.

Lung Leakiness Experiments.

Ten micrograms of total exosome protein was injected via tail vein. Conditioned media (CM) was prepared by filtering SN fractions of cultured B16 cells through a 0.22-μm filter. One hundred microliters CM was injected via tail vein injection. For exosome control groups, mice were injected with PBS or synthetic 100 μm unilamellar liposomes size in parallel (Encapsula nanoscience). Twenty hours after exosome treatment, mice were injected with 2 mg of Texas Red®-lysine fixable dextran 70,000 MW (Invitrogen) via retro-orbital injection. One hour after dextran injection, mice were sacrificed and perfused with PBS. Lungs were dissected and fixed in a mix of 2% PFA and 20% sucrose overnight, then embedded in Tissue-tek O.C.T. embedding compound (Electron Microscopy Sciences) and frozen in a dry ice bath.

In vivo Studies, Bone Marrow Cell Education, Transplantation, Tumor Induction, and Metastasis Assays.

For analysis of exosome influence in B16-F10 tumor metastasis, wild type C57Bl/6 mice were injected in the flank with $1\times10^6$ B16-F10mCherry. Seven days after, 10 μg of B16-F10 exosomes were injected during three weeks three times a week, metastasis was evaluated by mCherry expression at days 19 and 28. For analysis of exosome influence in metastatic behavior in BM cells, wild type C57Bl/6 mice were injected three times a week with the indicated dose of exosomes during 28 days. After exosome education, mice were then injected subcutaneously in the flank with $1\times10^6$ B16-F10mCherry luciferase. Controls included PBS and synthetic unilamellar liposome (100 μm) (Encapsula nanoscience) injection. Live animal fluorescence optical imaging was performed using IVIS Spectrum system (Caliper, Xenogen). The tumor bearing mice were anesthetized (isoflurane/02) and a solution of D-luciferin (50 mg/Kg in PBS in a total volume of 100 μl) was administered. Five minutes later mice were euthanized and organs were analyzed for luciferase expression. Data were quantified with the Living Imaging software 4.2. To track exosome-educated BM, eGFP-transgenic (C57Bl/6-TgN(ActbEGFP) 1Osb/J (Jackson Laboratory)) were injected three times a week with 5 or 10 μg of B16-F10 exosomes during 28 days for BM education. BM cells were then harvested by flushing femurs and tibias of eGFP donor animals. WT C57Bl/6 mice were then lethally irradiated (950 rads) and transplanted with 5×10⁶ eGFP total BM cells (isolated from eGFP-transgenic mice injected with B16 exosomes) via retro-orbital injection. After BM reconstitution (4 weeks) mice were injected subcutaneously in the flank with 1×10⁶ B16-F10mCherry or LLC-mCherry. SK-Mel28mCherry cells 2×10⁶ cells were injected in the flank in a mix of 1:1 serum-free RPMI:grow factor reduced Matrigel. For lung colonization experiments, 1×10⁵ B16-F10 cells or 5×10⁵ SK-Mel-28 cells were injected via tail vein in 100 µA of PBS. Tissues were dissected and fixed in 4% PFA or in a mix of 2% PFA and 20% sucrose overnight, then embedded in Tissue-tek O.C.T. (Electron Microscopy Sciences) and the blocks frozen in a dry ice/ethanol bath. Additionally, tissues were snap-frozen in liquid nitrogen for RNA/protein extraction. Tissues used to evaluate metastasis in BM-educated mice and controls (Table 5) were paraffin embedded stained with hematoxilin/eosin, metastases were evaluated by microscopy. All mouse work was performed in accordance with institutional, IACCUC and AAALAS guidelines. All animals were monitored for abnormal tissue growth or ill effects according to AAALAS guidelines and sacrificed if excessive deterioration of animal health was observed.

Immunofluorescence Microscopy.

For immunohistochemistry, tissues were fixed in a mix of 2% PFA and 20% sucrose overnight and cryoembedded in Tissue-tek O.C.T. embedding compound (Electron Microscopy Sciences). Sections (12 µm) were stained with the primary antibodies against CD31, VCAM-1 (BD). For analysis of the vasculature, animals were injected with Alexa Fluor 555 conjugated Isolectin GS-IB4 (50 m for 10 min, Molecular Probes) before sacrifice. GFP and mCherry-positive cells were detected by their intrinsic signal. Fluorescent images were obtained using a computerized Nikon Confocal microscope, and analyzed by using Nikon software. To determine the vessel density in metastatic lesions, digital images of mCherry/GFP stained sections were analyzed with ImageJ Software (NIH).

Flow Cytometry and Antibodies.

Murine lung and tissues were prepared for flow cytometry by mincing followed by digestion at 37° C. for 45-60 min with an enzyme cocktail (Collagenase A and DNase I, Roche). Single cell suspensions were filtered through a 70-µm strainer. Murine peripheral blood was obtained by retro-orbital bleeding directly into anti-coagulant tubes (EDTA). Cell suspensions were blocked with Fc-block (CD16/CD32, BD) and then incubated with the following primary antibodies: anti-CD11b-FITC (clone M1/70), -VEGFR2-PE (clone Avas12α1), -pan CD45, B220, CD3, TER19 (Lineage negative cell detection kit), c-Kit-APC (clone 2B8), -Sca-1-PE(clone D7), Gr1-PE (clone (RB6-8C5), -F4/80-APC (clone BM8) (BD), -Tie2-PE (clone TEK4) -CD29APC (clone HMb1), -CD105-PE (clone MJ7/18) -MET-FITC (ebioclone4) (BD or eBioscience). Cellular fluorescence was measured using a FACSCalibur cytometer with CellQuest software (BD). FACS data were analyzed with FlowJo software (TreeStar).

Flow Cytometry for Human Samples.

Peripheral blood obtained from melanoma patients and healthy controls was spun at 500×g for 10 min at 4° C. to separate the plasma from the circulating cells. Plasma was then used for exosome isolation and analysis. Peripheral blood cells were isolated using Ficoll-Paque gradient (GE Healthcare), according to the manufacturer's protocol. The buffy coat was separated and cells were washed in 1×PBS/1% BSA and collected by centrifugation at 400×g for 5 minutes at 4° C. Residual red blood cells were lysed for 4 minutes at 4° C. using ACK lysis buffer (Gibco). Live cells were counted using Trypan blue exclusion and 1×10⁶ live cells were used for each stain. Cells were incubated with fluorochrome-conjugated antibodies diluted in 1×PBS/1% BSA for 30 minutes at 4° C. Cells were then washed in 1×PBS, 1% BSA, collected by centrifugation and fixed by resuspension in 1% paraformaldehyde (diluted in 1×PBS). Flow cytometric analysis of thymocytes and BM cells using antibodies specific for markers of interest was performed as previously described (Tan et al, "Requirement for Notch1 Signals at Sequential Early Stages of Intrathymic T Cell Development," Nat. Immunol. 6(7): 671-79 (2005), which is hereby incorporated by reference in its entirety). Antibodies (clones) used in this study were: anti-CD45 (2D1), anti-CD117 (104D2), anti-CD34 (581), anti-TIE2 (CD202B) (33.1), anti-MET (eBioclone 97), anti-CD105 (43A3) and anti-CD29 (TS2/16). Antibody-fluorochrome conjugates were purchased from BD Biosciences, eBioscience or Biolegend and used at predetermined saturating concentrations. Data acquired on a BD FACS Canto™ was imported into FlowJo™ (Tree Star) software for analysis. Red blood cells and cell debris were excluded from analysis based on low forward scatter.

BM Progenitor Cell Enrichment, In Vitro Treatment of BM Cells, and BM Response to HGF.

Mice were sacrificed and BM was isolated by flushing the femur and tibia with staining media (1% BSA in PBS) using a 25G½" needle (BD) and further disrupting it by pipeting. Cell suspensions were filtered through 70 µm cell strainers (BD) prior to centrifugation. Red blood cells (RBC) from BM suspensions were lysed using ACK Lysis Buffer (Invitrogen). To enrich for progenitors, lineage positive (Lin⁺, i.e., CD5, CD45R, CD19, CD11b, Ly6G/C, 7-4, TER119 positive) BM cells were immunomagnetically depleted using the EasySep® Mouse Hematopoietic Progenitor Cell Enrichment Kit (Stem Cell Technologies) as per manufacturer's instructions. For in vitro BM treatment with exosomes, BM cells were flushed as above and cultured in Stem Span (Stem Cell Technologies) for 16 hours in the presence or absence of 20 µg/ml indicated exosomes. For HGF analysis BM cells were then stimulated with 5 ng/ml HGF (Peprotech) for 4 hours and collected for Western blot analysis in RIPA buffer as indicated below by adding phosphatase inhibitors (1 mM Sodium orthovanadate and 5 mM β-Glycerol phosphate). For MET signaling inhibition, cells were incubated with 20 nM Crizotinib (Selleck Bio) 1 hour before HGF stimulation.

Quantitative Real-Time PCR and Short-Hairpin RNA Interference Studies.

Frozen tissues or cell lines were analyzed for specific gene expression using pre-designed TaqMan® assays (specific assays numbers: MET mouse Mm01156972_m1, CD44 mouse Mm01277163, Rab267a human-Hs00608302_m1, Rab27a mouse-Mm00469997_m1, s100a8-Mm00496696_g1, s100a9-Mm00656925_m1) or GFP or mCherry-specific primers (Kaplan et al., "VEGFR1-Positive Haematopoietic Bone Marrow Progenitors Initiate the Pre-Metastatic Niche," *Nature* 438:820-827 (2005), which is hereby incorporated by reference in its entirety) using SybrGreen PCR reagents (Applied Biosystems). Briefly, total RNA was extracted from tissues or cells using the RNeasy kit (Qiagen), and reverse-transcribed using Superscript III reverse transcriptase (Invitrogen). Quantitative real-time PCR (qRT-PCR) was performed on a 7500 Fast Real Time PCR System (Applied Biosystems), using TaqMan Universal PCR Master Mix (Applied Biosystems). Relative expression was normalized to β-actin levels. For shRNA interference of Rab family members, lentiviral vectors encoding shRNAs specific for various members of the Rab family and as well as GFP reporter and puromycin resistance gene cassettes were purchased from Thermo Fisher. Human Rab27a shRNA sense sequences were: V3LHS_300918: CCCAGTGTACTTTACCAATATA (SEQ ID NO: 1), V3LHS_300917: CAGGGAAGACCAGTGTACTTTA (SEQ ID NO: 2), results human shRNA were similar for both shRNAs but only 300918 is shown in figures. Sense sequence for mouse Rab27a shRNA was V3LHS_300916: ACAGGAGAGGTTTCGTAGCTTA (SEQ ID NO: 3), scramble sense sequence used was: ATCTCGCTTGGGC-GAGAGTAAG (SEQ ID NO: 4). Mouse MET shRNA sense sequences were: V3LMM_456078-CCAGACTTTTCATA-CAAGAATA (SEQ ID NO: 5), V2LMM_30812: CCCTAT-GTAGA-TCCTGTAATAA (SEQ ID NO: 6) results were similar for both shRNAs. Mouse Met shRNA sense sequences were: V3LMM_456078: 5'-CCA-GACTTTTCATACAAGAATA-3' (SEQ ID NO: 5), V2LMM_30812: 5'-CCCTATGTAGA-TCCTGTAATAA-3' (SEQ ID NO: 6). Met knockdown efficiency was similar for both shRNAs (routinely exceeding 90% as determined by GFP expression).

Proteomic Analysis.

Identification of exosomal proteins was performed using reversed phase high pressure liquid chromatography-mass spectrometry (HPLC-MS). Samples were denatured at 90° C., reduced with 10 mM DTT at 51° C. for 1 h and alkylated with 50 mM iodoacetamide at 25° C. for 45 min. Proteins were digested with trypsin (Promega, Madison, Wis.) overnight at 25° C. Tryptic peptides were concentrated by vacuum centrifugation and desalted using in-house made C18STAGE Tips prior to mass spectrometric analysis. Samples were loaded by an Eksigent AS2 autosampler onto a 75 µm fused silica capillary column packed with 11 cm of C18 reverse phase resin (5 µm particles, 200 Å pore size; Magic C18; Michrom BioResources Inc., Auburn, Calif., USA). Peptides were resolved on a 180 minute 1-100% buffer B gradient (buffer A=0.1 mol/l acetic acid, Buffer B=70% acetonitrile in 0.1 mol/l acetic acid) at a flow rate of 200 nl/min (1200 series; Agilent, Santa Rosa, Calif., USA). The HPLC was coupled to a mass spectrometer (LTQ-Orbitrap; ThermoFisher Scientific, Carlsbad, Calif., USA) with a resolution of 30,000 for full MS followed by seven data-dependent MS/MS analyses. Collision-induced dissociation (CID) was used for peptide fragmentation. Each sample was analyzed at least two times.

All MS data were analyzed with Proteome Discoverer software (version 1.2; Thermo Fisher Scientific, San Jose, Calif.) using the SEQUEST algorithm to search against human and mouse UniProt databases. The peptides were constrained to be tryptic and up to 2 missed cleavages were allowed. Carbamidomethylation of cysteine was specified as a fixed feature and oxidation of methionine as a variable modification. The precursor ion tolerance was set to 25 ppm, and fragment ion mass tolerance to 0.8 Da. Search results were analyzed individually and data for replicates were combined and evaluated. For validation of proteomic analysis western blot analysis was performed for selected proteins (i.e., MET, CD44, Annexin A2, Annexin A6—see FIG. 4A) using equal amounts of exosomes derived from B16-F1 and B6-F10 cells.

Microarray Preparation and Analysis.

For analyzing the genes modified in lungs by B16-exosomes, a total of 10 µg of exosome protein was injected by tail vein. Twenty-four and forty-eight hours later, mice were sacrificed, and lungs were kept in RNA-later solution (Ambion) until RNA extraction. A total of 3 mice were used per time point and the experiment was performed in triplicate. Total RNA from cells was isolated using RNeasy mini kit (Qiagen) and the Affymetrix a one-round in vitro transcription (IVT) RNA Amplification Kit was used to amplify 1.5 mg amounts of total RNA. The cDNA was synthesized with a primer containing oligo (dT) and T7 RNA polymerase promoter sequences. Double-stranded cDNA was then purified and used as a template to generate biotinylated cRNA. The quantity and quality of the amplified cRNA was assessed using NanoDrop ND-1000 Spectrophotometer (Thermo Scientific, Wilmington, Del.) and Agilent Bioanalyzer (Santa Clara Calif.). The biotin labeled cRNA was fragmented and hybridized to the Affymetrix Mouse Genome 430 Plus 2.0 GeneChip arrays (Santa Clara, Calif.) for analysis of over 39,000 transcripts on a single array. After hybridization, GeneChip arrays were washed, stained, and scanned using a GeneChip Scanner 3000 7G according to the Affymetrix Expression Analysis technical Manual. Affymetrix GeneChip Operating Software was used for image acquisition. The target signal intensity from each chip was scaled to 500. Triplicate samples from each exosome-treated and control lung samples were analyzed to identify differentially expressed genes. In case of BM-educated progenitor cells, the experiment was performed in duplicate. For statistical analysis, genes whose expression differed between groups by a factor of at least two were selected. A hierarchical clustering method was applied to group the genes and samples on the basis of the similarities in gene expression, and the unsupervised analyses were visualized using the SOTA and TreeView software assuming euclidean distances between genes. The null hypothesis of equal means between the two groups was tested using t-test, computing p-values using a permutation test. Fold expression was calculated from the expression ratio in the exosome-treated conditions with respect to control samples. Microarray raw data tables have been deposited in the Gene Expression Omnibus.

Western Blot, Antibodies and Multiplex Analysis.

Exosomes or cells were lysed with RIPA buffer containing a complete protease inhibitor tablet (Roche). Lysates were cleared by centrifugation at 14,000×g for 20 min. Supernatant fractions were used for Western blot. Protein extracts were resolved by SDS-PAGE and probed with the indicated antibodies. The following antibodies were used for Western Blot or immunofluorescence analysis: anti-Hsp90, anti-Hsp70, anti-Hsc70 (Stressgen), Rab-family sampler kit (Rab4, 5, 7, 9, 11, Cell Signaling), anti-Rab27a (Sigma/Abnova), anti-TYRP-2 (PEP-8h) (kindly provided by Dr. Hearing, (NIH/NCI), anti-VLA4 (Chemicon clone/PS2), anti-MelanA (Santa Cruz), anti-Alix (Cell Signaling), anti-tsg101 (GeneTex), anti-MET/Phospho MET (Tyr1234/1235), anti-phospho-S6 kinase (Ser371), anti-phospho ERK (Tyr202/Tyr204) (Cell signaling). Anti-GAPDH or -β-actin antibodies (Santa Cruz) were used as a loading control. The intensities of the immunoreactive bands were quantified by densitometry using Image J software. For analysis of protein expression profiles in conditioned media of cells, the mouse angiogenesis antibody array (R&D) was employed using 200 µg of cell extracts or 450 µl of 24 hour conditioned media. MET/PhosphoMET analysis kit was purchased from MesoScale Discovery. All reagents were provided with the MSD kit and the protocol was performed following commercial protocol with 10 µg of protein extract. MSD plates were measured on the MSD Sector Imager 2400 plate reader. The raw data was measured as electrochemiluminescence signal (light) detected by photodetectors and analyzed using the Discovery Workbench 3.0 software (MSD). Mean intensity is shown in the graphs.

Flow Cytometric Analysis of Exosomes.

For exosome flow analysis, 50 to 100 μg of isolated exosomes were coupled to 4 μm aldehyde/sulphate latex beads (Invitrogen) by co-incubating them for 60 minutes at room temperature, followed by the addition of BSA to a final concentration of 5%. Beads were then incubated for an additional 5 minutes at room temperature, then washed twice with 1×PBS. To block unspecific interactions during flow, beads were incubated with 0.1M glycine overnight, followed by two 1×PBS washes. Bead-coupled exosomes were then incubated with anti-CD9-FITC (Abcam), or anti-CD63-FITC (BD) and Anti HLA-A B C PE (BD) antibodies using a standard flow cytometry protocol.

Statistical Analysis.

Error bars in graphical data represent means±s.e.m. Mouse experiments were performed in duplicate, using at least 5 mice per treatment group. All the in vitro experiments were performed at least in duplicate. Statistical significance was determined using a two-tailed Student's t test, and P<0.05 were considered statistically significant by ANOVA. For tumor growth we performed two-way ANOVA statistical analysis using Graph Pad Prism software.

Figures 1A, 1B:
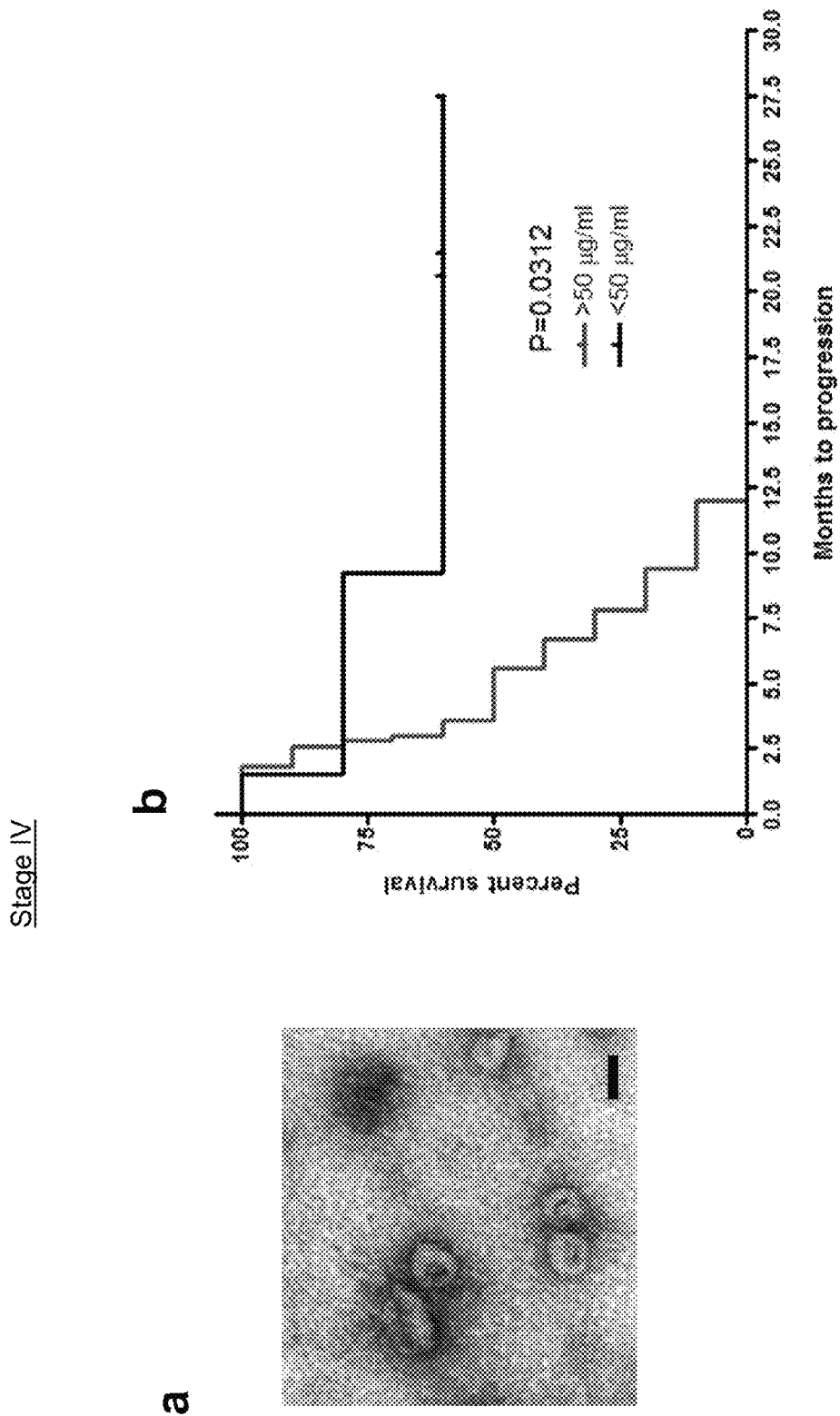
FIGS. 1A-1E shows the analysis of protein expression in circulating exosomes from melanoma patients.

Example 1—Circulating Exosome-Derived Proteins are Diagnostic Markers in Melanoma Patients To determine the significance of circulating exosome levels in metastatic disease, melanoma, a highly metastatic form of cancer was investigated (Braeuer et al., "Transcriptional Control of Melanoma Metastasis: The Importance of the Tumor Microenvironment," Semin. Cancer Biol. 21:83-88 (2011); Fidler, I. J., "Critical Determinants of Melanoma Metastasis," J. Investig. Dermatol. Symp. Proc. 1:203-208 (1996), which are hereby incorporated by reference in their entirety). In a prospective blinded study, exosomes from the plasma of melanoma patients with increasing clinical stage was isolated and characterized. Standard exosome isolation methods, including ultracentrifugation and flotation on a sucrose cushion led to the isolation of ~100 nm particles (exosomes), as demonstrated by electron microscopy (FIG. 1A). Known exosome markers, including CD63, CD9 and MHC-I were detected in the exosomes of patients by flow cytometry. Exosome size distribution and number were quantified using a nanoparticle tracking system (NanoSight) and did not differ based on clinical stage (FIG. 6A). In contrast, the levels of exosome proteins were higher in patients with Stage IV disease compared to normal controls as well as patients with less advanced disease (FIG. 6B). Furthermore, stage IV patients with protein-poor exosomes (<50 μg/ml) had a survival advantage compared to those with protein-rich exosomes (>50 μg/ml) (FIG. 1B). These data suggest that there is a qualitative difference in protein content in exosomes from patients with metastatic disease which may be an indicator of survival.

Figure 1C:
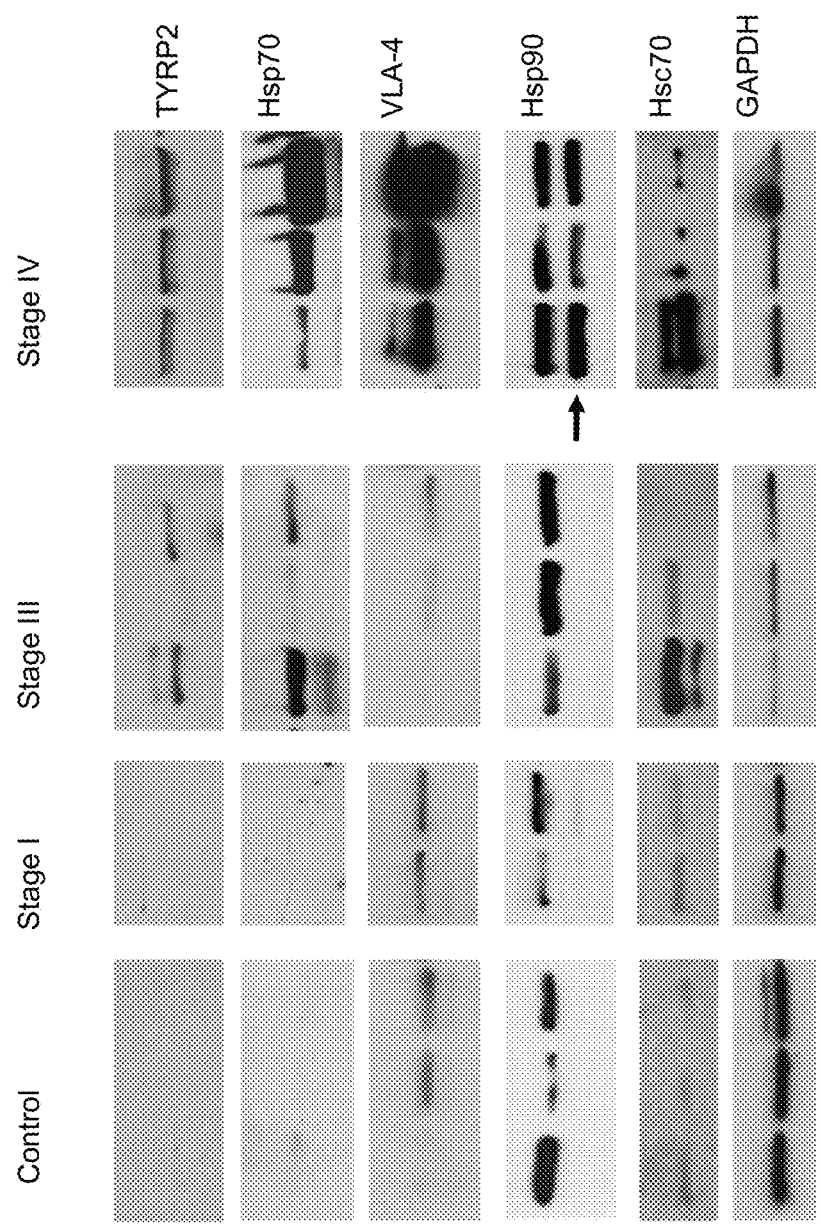
Figure 1D:
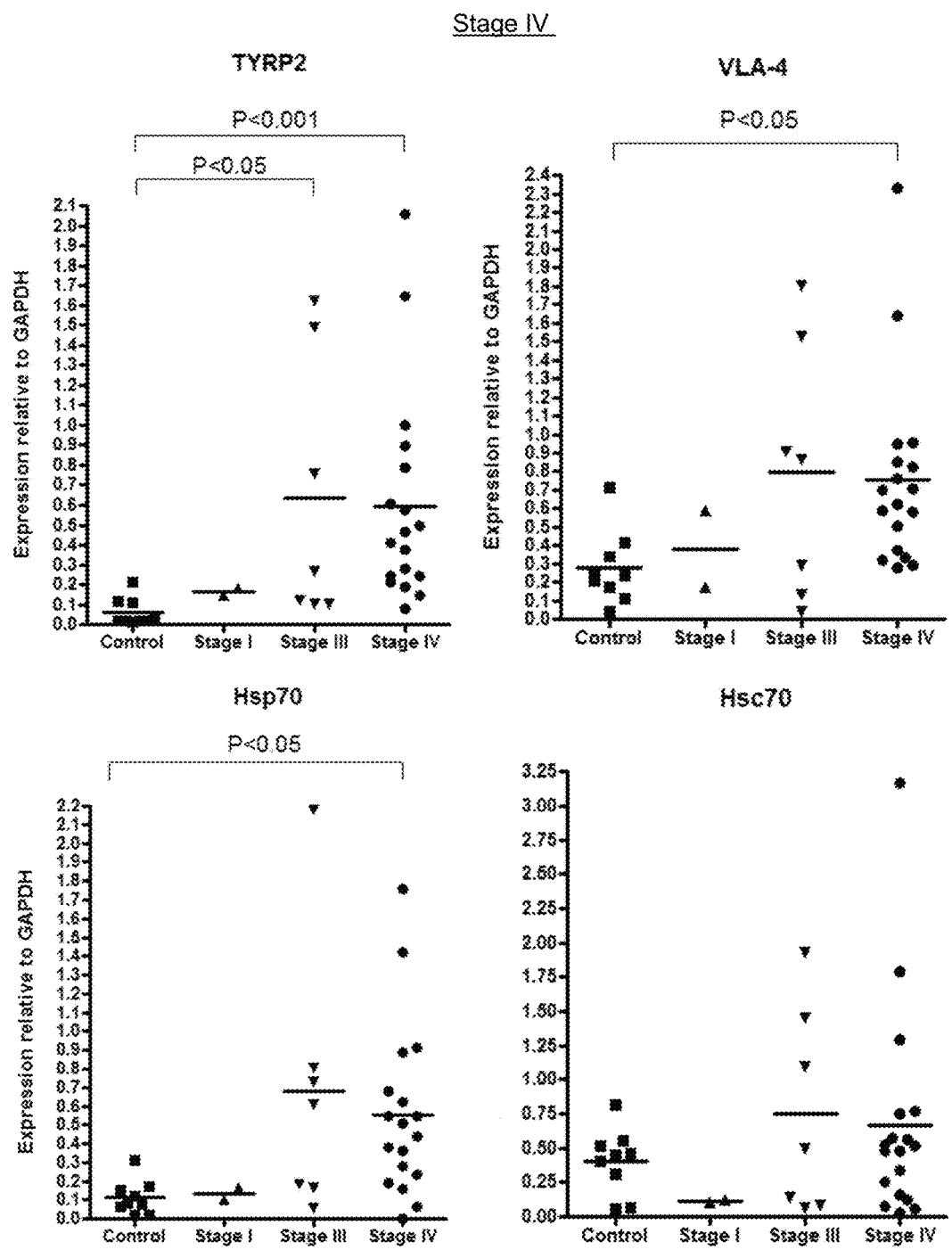
Figure 1E:
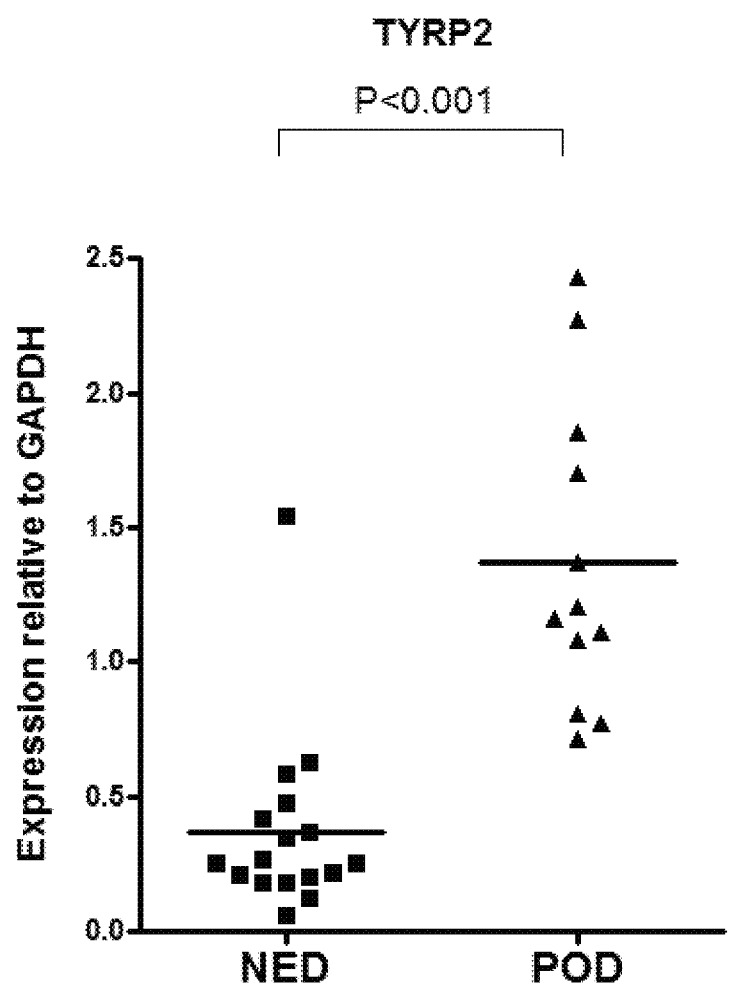

To characterize the exosome proteins found in melanoma, exosomes from the highly metastatic B16-F10 murine melanoma and four human melanoma cell lines (SK-Mel28/-202/-265/-35) were examined (Table 2 below). They were heterogeneous in shape, had an average size of ~100 nm and expressed typical exosome markers including Hsc70 and tsg101 (FIG. 6C). Mass spectrometry led to the identification of exosomal proteins from both murine and human sources (Table 2). A subset of these proteins was analyzed in circulating exosomes isolated from melanoma patients to determine their potential as a new diagnostic 'signature' in the clinical setting. Using Western blot analysis, TYRP2 (a melanoma specific protein), VLA-4, and Hsp70 levels were significantly increased in the exosomes of patients with stage IV disease versus those of normal controls (FIG. 1C, 1D). Furthermore, stage III patients had increased levels of exosome-derived TYRP2 compared to control subjects (FIG. 1C, 1D). In contrast, Hsc70 levels were not significantly elevated in patient-derived exosomes regardless of their clinical stage (FIG. 1C, 1D). Interestingly, an Hsp90 isoform was found in exosomes isolated from 70% of stage IV melanoma patients (FIG. 1C, black arrow) that has previously been reported to be important in neoplastic transformation (Grammatikakis et al., "The Role of Hsp90N, a New Member of the Hsp90 Family, in Signal Transduction and Neoplastic Transformation," J. Biol. Chem. 277:8312-8320 (2002), which is hereby incorporated by reference in its entirety). The prognostic value of these markers in exosomes isolated from frozen plasma in a retrospective cohort of patients with stage III melanoma was also analyzed (FIG. 1E). TYRP2 levels were elevated in the exosomes of those Stage III patients who eventually developed metastatic disease as compared to those who remained disease-free (NED=non-evidence of disease, FIG. 1E). Analysis of VLA-4 and Hsp70 demonstrated a trend (although not statistically significant) indicating that the usefulness of these proteins in Stage III melanoma prognosis requires further investigation. These data support the use of a simple blood test to predict stage III prognosis and stage IV outcome by analyzing circulating exosomes.

TABLE 2

Melanoma Exosome Signature. List of main proteins found in exosomes derived from 5 melanoma cell lines (B16-F10, SK-MEL-28, SK-MEL-202, SK-MEL-35 and SK-MEL-265) by mass-spectrometry.

| Symbol | Protein name | Function |
| --- | --- | --- |
| DCT | Dopachrome tautomerase (tyrosine-related protein 2) | Melanoma-related |
| LDHA | Lactate dehydrogenase A | Melanoma-related |
| MCAM | Melanoma cell adhesion molecule | Melanoma-related |
| TYRP1 | Tyrosinase-related protein 1 | Melanoma-related |
| YWHAG | Tyr 3-monooxygenase/trp 5-monooxygenase activation protein, γ | Melanoma-related |
| YWHAZ | Tyr 3-monooxygenase/trp 5-monooxygenase activation protein, ζ | Melanoma-related |
| ITGAV | Integrin, alpha V (vitronectin receptor) | Membrane protein |
| ITGB1 | Integrin, beta 1 (fibronectin receptor) | Membrane protein |
| GPNMB | Glycoprotein (transmembrane) nmb | Membrane protein |
| TFRC | Transferrin receptor (p90, CD71) | Membrane protein |
| ANXA1 | Annexin A1 | Membrane protein |
| ANXA11 | Annexin A11 | Membrane protein |
| ANXA2 | Annexin A2 | Membrane protein |
| ANXA5 | Annexin A5 | Membrane protein |

TABLE 2-continued

Melanoma Exosome Signature. List of main proteins found in exosomes derived from 5 melanoma cell lines (B16-F10, SK-MEL-28, SK-MEL-202, SK-MEL-35 and SK-MEL-265) by mass-spectrometry.

| Symbol | Protein name | Function |
|---|---|---|
| ANXA6 | Annexin A6 | Membrane protein |
| ENG | Endoglin | Membrane protein |
| CD44 | CD44 | Membrane protein |
| HSPA1A | Heat shock 70 kDa protein 1A; heat shock 70 kDa protein 1B | Heat shock protein |
| HSPA1L | Heat shock 70 kDa protein 1-like | Heat shock protein |
| HSPA4 | Heat shock 70 kDa protein 4 | Heat shock protein |
| HSPA8 | Heat shock 70 kDa protein 8 | Heat shock protein |
| HSP90AA1 | Heat shock protein 90 kDa alpha (cytosolic), class A member 2 | Heat shock protein |
| HSP90AB1 | Heat shock protein 90 kDa alpha (cytosolic), class B member 1 | Heat shock protein |
| HSPA5 | Heat shock 70 kDa protein 5 (glucose-regulated protein, 78 kDa) | Heat shock protein |
| BSG | Basigin | Cell motility/ECM |
| CDC42 | Cell division cycle 42 | Cell motility/ECM |
| CFL1 | Cofilin 1 (non-muscle) | Cell motility/ECM |
| ERBB2IP | Erbb2 interacting protein | Cell motility/ECM |
| FLNA | Filamin A, alpha | Cell motility/ECM |
| KRT1 | Keratin 1 | Cell motility/ECM |
| KRT10 | Keratin 10 | Cell motility/ECM |
| MSN | Moesin | Cell motility/ECM |
| MYO1C | Myosin IC | Cell motility/ECM |
| MYH9 | Myosin, heavy chain 9, non-muscle | Cell motility/ECM |
| NCSTN | Nicastrin | Cell motility/ECM |
| SERPINE2 | Serpin peptidase inhibitor, clade E (PAI-1) | Cell motility/ECM |
| SDCBP | Syndecan binding protein (syntenin) | Cell motility/ECM |
| ACTB | Actin, beta | Cytoskeleton |
| ACTN4 | Actinin, alpha 4 | Cytoskeleton |
| TUBA1C | Tubulin, alpha 1c | Cytoskeleton |
| AP1B1 | Adaptor-related protein complex 1, beta 1 subunit | Endocytic pathways |
| CLTC | Clathrin, heavy chain (Hc) | Endocytic pathways |
| EHD1 | EH-domain containing 1 | Endocytic pathways |
| EHD4 | EH-domain containing 4 | Endocytic pathways |
| VAT1 | Vesicle amine transport protein 1 | Endocytic pathways |
| RAB7A | RAB7A, member RAS oncogene family | Endocytic pathways |
| RAP1A | RAP1A, member of RAS oncogene family | Endocytic pathways |
| IGSF8 | Immunoglobulin superfamily, member 8 | Immunoglobulin |
| JAK1 | Janus kinase 1 | Kinase |
| ALDOA | Aldolase A, fructose-bisphosphate | Metabolism |
| ENO1 | Enolase 1, (alpha) | Metabolism |
| FASN | Fatty acid synthase | Metabolism |
| GARS | Glycyl-tRNA synthetase | Metabolism |
| MDH2 | Malate dehydrogenase 2, NAD (mitochondrial) | Metabolism |
| PGD | Phosphogluconate dehydrogenase | Metabolism |
| PHGDH | Phosphoglycerate dehydrogenase | Metabolism |
| PGK1 | Phosphoglycerate kinase 1 | Metabolism |
| PGAM1 | Phosphoglycerate mutase 1 (brain) | Metabolism |
| PKM2 | similar to Pyruvate kinase, isozymes M1/M2 | Metabolism |
| TPI1 | TPI1 pseudogene; triosephosphate isomerase 1 | Metabolism |
| TAX1BP1 | Tax1 (human T-cell leukemia virus type I) binding protein 1 | Miscellaneous |
| AARS | Alanyl-tRNA synthetase | Miscellaneous |
| ACLY | ATP citrate lyase | Miscellaneous |
| ATP6V1B2 | ATPase, H+ transporting, lysosomal 56/58 kDa, V1 subunit B2 | Miscellaneous |
| ATP1A1 | ATPase, Na+/K+ transporting, alpha 1 polypeptide | Miscellaneous |
| BACE2 | Beta-site APP-cleaving enzyme 2 | Miscellaneous |
| CAP1 | CAP, adenylate cyclase-associated protein 1 (yeast) | Miscellaneous |
| CAND1 | Cullin-associated and neddylation-dissociated 1 | Miscellaneous |
| CCT2 | Chaperonin containing TCP1, subunit 2 (beta) | Miscellaneous |
| CCT5 | Chaperonin containing TCP1, subunit 5 (epsilon) | Miscellaneous |
| CCT7 | Chaperonin containing TCP1, subunit 7 (eta) | Miscellaneous |
| CCT8 | Similar to chaperonin containing TCP1, | Miscellaneous |
| DNAJA1 | DnaJ (Hsp40) homolog, subfamily A, member 1 | Miscellaneous |
| EEF1A1 | Eukaryotic translation elongation factor 1 alpha-like 7 | Miscellaneous |
| EEF1G | Eukaryotic translation elongation factor 1 gamma | Miscellaneous |
| EEF2 | Eukaryotic translation elongation factor 2 | Miscellaneous |
| GNAS | GNAS complex locus | Miscellaneous |
| HIST1H2AH | Histone cluster 1, H2ag; | Miscellaneous |
| KPNB1 | Karyopherin (importin) beta 1 | Miscellaneous |
| MVP | Major vault protein | Miscellaneous |
| MFGE8 | Milk fat globule-EGF factor 8 protein | Miscellaneous |
| NAP1L1 | Nucleosome assembly protein 1-like 1 | Miscellaneous |
| OLA1 | Obg-like ATPase 1 | Miscellaneous |
| PCBP2 | Poly(rC) binding protein 2 | Miscellaneous |
| PDCD6IP | Programmed cell death 6 interacting protein | Miscellaneous |
| RPL18 | Ribosomal protein L18 | Miscellaneous |
| RPSA | Ribosomal protein SA pseudogene 9; | Miscellaneous |
| SQSTM1 | Sequestosome 1 | Miscellaneous |

TABLE 2-continued

Melanoma Exosome Signature. List of main proteins found in exosomes
derived from 5 melanoma cell lines (B16-F10, SK-MEL-28, SK-MEL-202,
SK-MEL-35 and SK-MEL-265) by mass-spectrometry.

| Symbol | Protein name | Function |
| --- | --- | --- |
| EIF4A1 | Similar to eukaryotic translation initiation factor 4A; | Miscellaneous |
| SLC1A5 | Solute carrier family 1 (neutral amino acid transporter), member 5 | Miscellaneous |
| SLC2A1 | Solute carrier family 2 (facilitated glucose transporter), member 1 | Miscellaneous |
| SLC3A2 | Solute carrier family 3, member 2 | Miscellaneous |
| UBC | Ubiquitin C | Miscellaneous |
| UBA1 | Ubiquitin-like modifier activating enzyme 1 | Miscellaneous |
| VCP | Valosin-containing protein | Miscellaneous |
| ALB | Albumin | Secreted molecules |
| APOE | Apolipoprotein E | Secreted molecules |
| C3 | Similar to Complement C3 precursor; | Secreted molecules |
| F5 | Coagulation factor V | Secreted molecules |

Figure 2A:
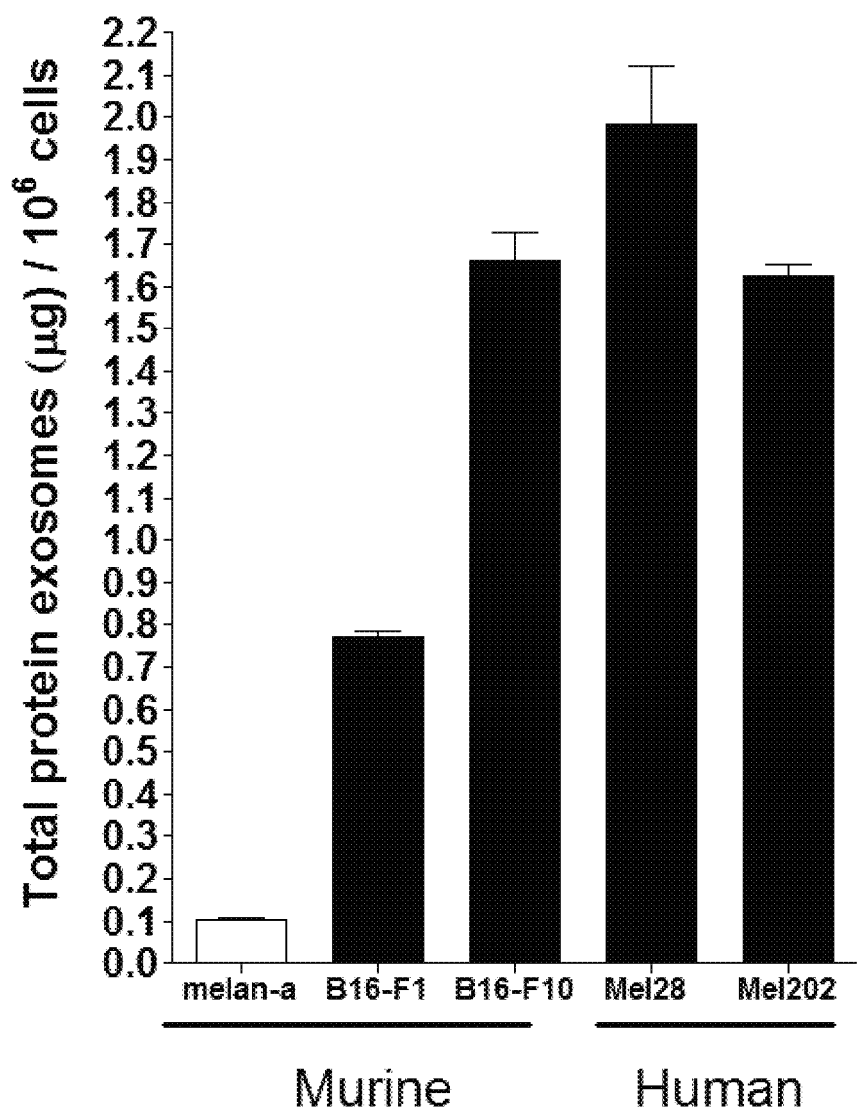
FIGS. 2A-2F depict the role of tumor-derived exosomes in metastasis. Measurement of the total protein per million cells in exosomes isolated from human Mel28 and Mel202 cells and mouse melan-a, B16-F1, and B16-F10 melanoma cells in culture is shown in the graph of FIG. 2A. Error bars represent s.e.m.
Figures 2B, 2C:
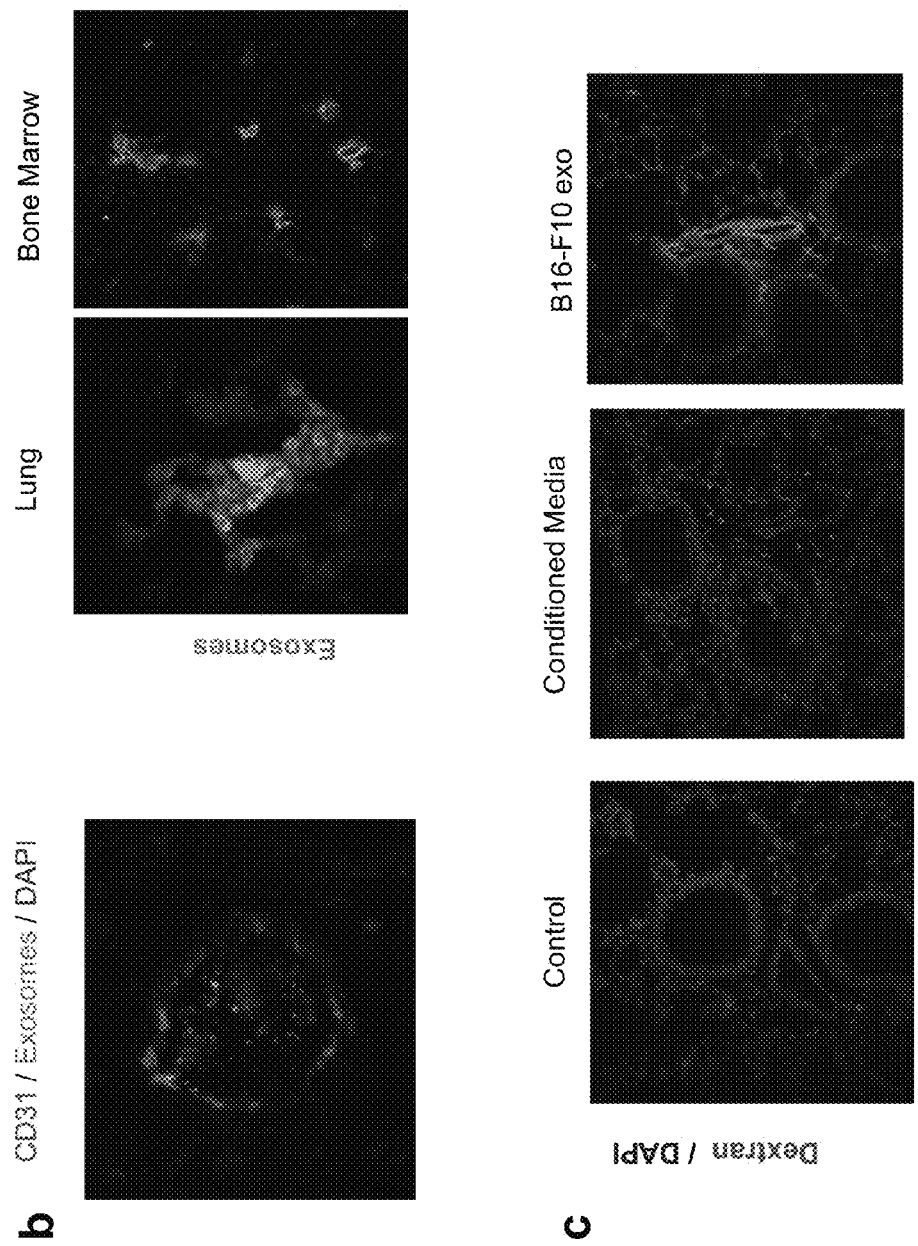

Example 2—Tumor-Released Exosomes Reach Metastatic Organs and Alter Metastatic Potential Analysis of the protein content in exosomes from cultured cell lines demonstrated that highly malignant melanoma cell lines derived from mice (B16-F10) and human (SK-Mel28, SK-Mel202) express higher amounts (from 2-fold to 15-20-fold) of protein than poorly metastatic (B16-F1) (Fidler & Nicolson, "Organ Selectivity for Implantation Survival and Growth of B16 Melanoma Variant Tumor Lines," *J. Nat'l Cancer Inst.* 57:1199-1202 (1976), which is hereby incorporated by reference in its entirety) and non-tumorigenic and non-metastatic cell lines (melan-a) (FIG. 2A). It was confirmed that other less metastatic tumor cell types, such as lung, breast and colon cancer cells, secrete lower levels of exosomes than B16-F10 cells (FIG. 7A). To analyze the tissue distribution/pattern of exosomes, B16-F10 exosomes were injected intravenously via tail vein in naïve mice. B16-F10 exosomes circulated systemically through blood vessels and within minutes of injection could be detected in target organs, such as the lungs and BM (FIG. 2B). The arrival of tumor-derived exosomes in the lungs was confirmed using fluorescently-labeled exosomes and staining for CD31 in lungs isolated from mice sacrificed five minutes after injection (FIG. 2B, left panel). After 24 hours, B16-F10 exosomes were found in the interstitium of the lung and in the BM (FIG. 2b, right panels), as well as the liver and spleen but not in the circulation (Table 3). Thus, exosomes are rapidly cleared from the circulation and fused with cells in distant organs that are common sites of metastases in melanoma. Moreover, it was confirmed that exosomes isolated after sucrose cushion purification showed an equivalent uptake and distribution, while exosome-labeling dye alone did not stain these organs.

TABLE 3

Tissue distribution of tail vein-injected B16-
F10-labelled exosomes in different organs after 24 or 48
hours analyzed by confocal microscopy.

| Tissue | 24 h | 48 h |
| --- | --- | --- |
| Lung | +++ | ++ |
| Bone Marrow | ++ | + |
| Spleen | + | − |
| Liver | + | − |
| Brain | − | − |
| Oviducts | − | − |

Vascular leakiness in the lungs is one of the main factors involved in pre-metastatic niche formation and metastasis (Huang et al., "Pulmonary Vascular Destabilization in the Premetastatic Phase Facilitates Lung Metastasis," *Cancer Res.* 69:7529-7537 (2009), which is hereby incorporated by reference in its entirety). To analyze the influence of tumor exosomes on vascular leakiness, B16-F10 exosomes were injected followed by perfusion at 24 hours with fluorescently-labeled dextran (MW=70 kDa). B16-F10 exosomes enhanced lung endothelial permeability after 24 hours, as judged by the presence of labeled dextran throughout the lung interstitium, when compared to conditioned media, control particles (FIG. 2C) and exosomes from non-metastatic cell lines (FIG. 7B).

To investigate the molecular pathways affected by exosome delivery in the lungs, gene expression profiling of lung tissue was performed 24 and 48 hours after B16-F10 exosome tail vein injection (FIG. 7C). A total of 130 genes were differentially expressed. Analysis of these genes demonstrated the upregulation of transcripts related to extracellular matrix remodeling and tissue inflammation, such as the family of heat-shock proteins and S100a9 (FIG. 16), indicating enhanced expression of previously described effectors of the pre-metastatic niche (Hiratsuka et al., "The S100A8-Serum Amyloid A3-TLR4 Paracrine Cascade Establishes a Pre-Metastatic Phase," *Nat. Cell Biol.* 10:1349-1355 (2008), which is hereby incorporated by reference in its entirety). QRT-PCR was employed to confirm that both S100a8 and S100a9 were upregulated in the lungs after exosome injection (FIG. 7C). Upregulation of TNF-α expression was more transient, as it was present only at 24 hours post injection, but not at 48 hours (FIG. 7C), suggesting that TNF-α could be involved in the observed increase in vascular permeability (Lucas et al., "Regulators of Endothelial and Epithelial Barrier Integrity and Function in Acute Lung Injury," *Biochem. Pharmacol.* 77:1763-1772 (2009), which is hereby incorporated by reference in its entirety).

Figure 2D:
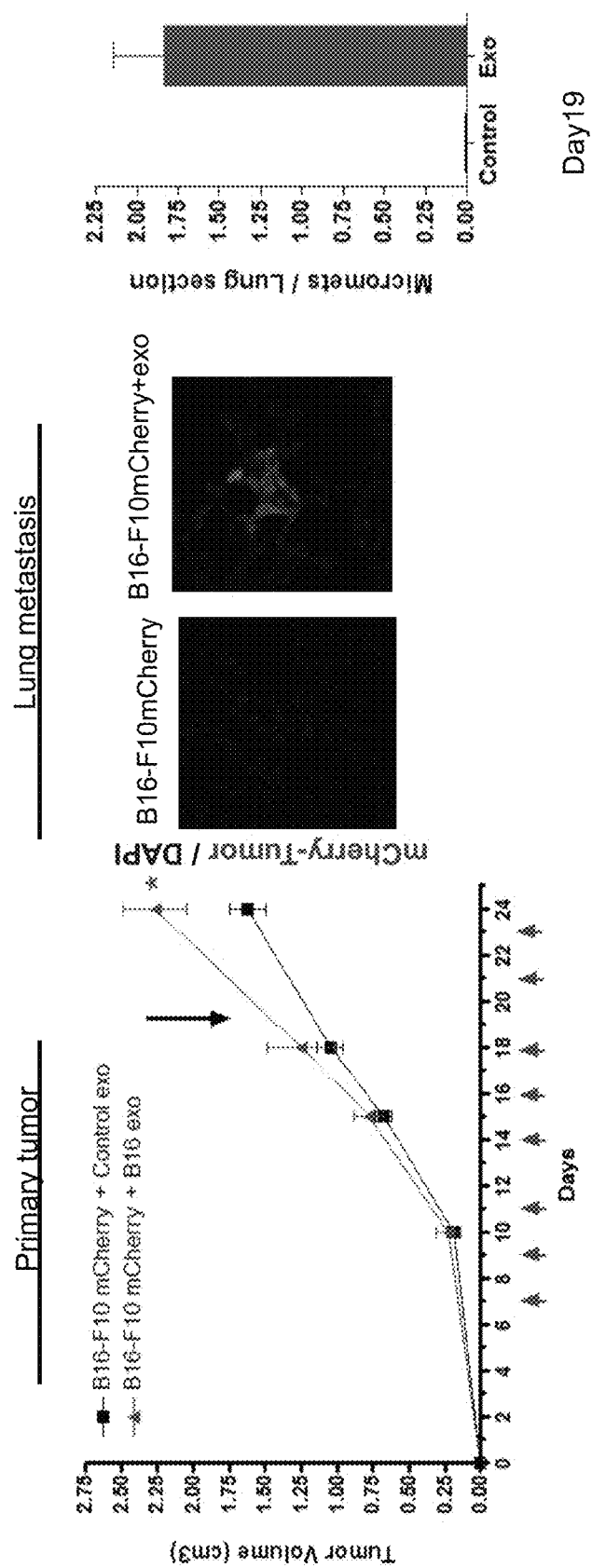

To further examine the role of tumor exosomes in metastasis, tail vein injections of B16-F10 derived exosomes were performed three days a week, starting seven days following orthotopic injection of B16-F10-mCherry cancer cells, and the kinetics of primary tumor growth and metastasis were analyzed. Mice treated with exosomes had obvious lung micrometastasis at day 19 compared to controls (FIG. 2D). Primary tumors were also larger, but this change was only observed later in the time course (FIG. 2D). To analyze the differences between exosomes from highly metastatic melanomas versus poorly metastatic lines, equal concentrations of highly metastatic B16-F10- and poorly metastatic B16-F1-derived exosomes were injected intravenously into recipient mice three times a week over 28 days. Given the lack of studies investigating the numbers of circulating exosomes in murine blood and to establish a baseline for the in vivo exosome injection experiments, NanoSight technology was used to determine the number of circulating exosomes in control and B16 melanoma bearing mice. In control, naïve, non-tumor bearing C57BL/6 mice, the average number of circulating exosomes was $115 \times 10^{10}$/ml of plasma (FIG. 8A). The total levels of circulating exosomes in mice bearing tumors <1.2 cm³ were similar to controls, but increased to $300-700 \times 10^{10}$ exosomes/ml of plasma as the tumor volume increased (FIG. 8A). Therefore, for B16 exosome injection experiments, tumor exosome numbers ranging from 5 to 20% of the total exosome number/ml of plasma were injected in C57BL/6 mice (FIG. 8A, 5 µg B16-F10 exosomes=$13.3 \times 10^{10}$ exosomes). After exosome treatment, mice were given subcutaneous implants of B16-F10-mCherry-luciferase$^+$ cells, and the effects of 'exosome-education' were observed.

Figure 2E:
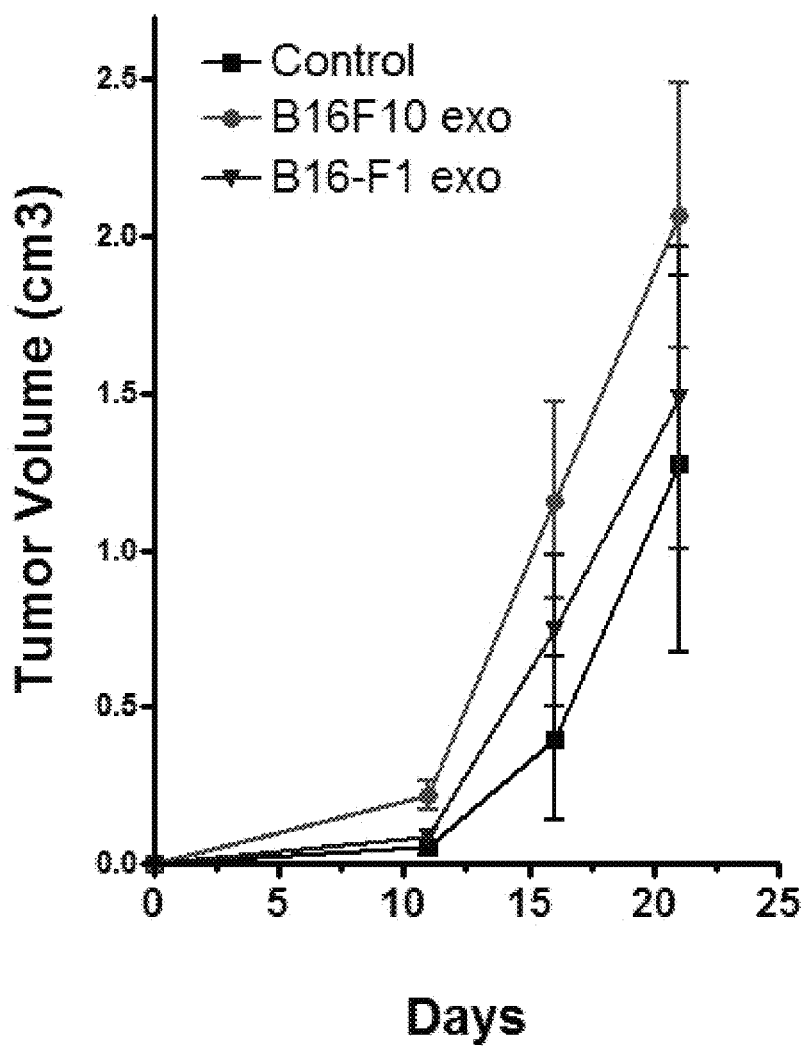
Figure 2F:
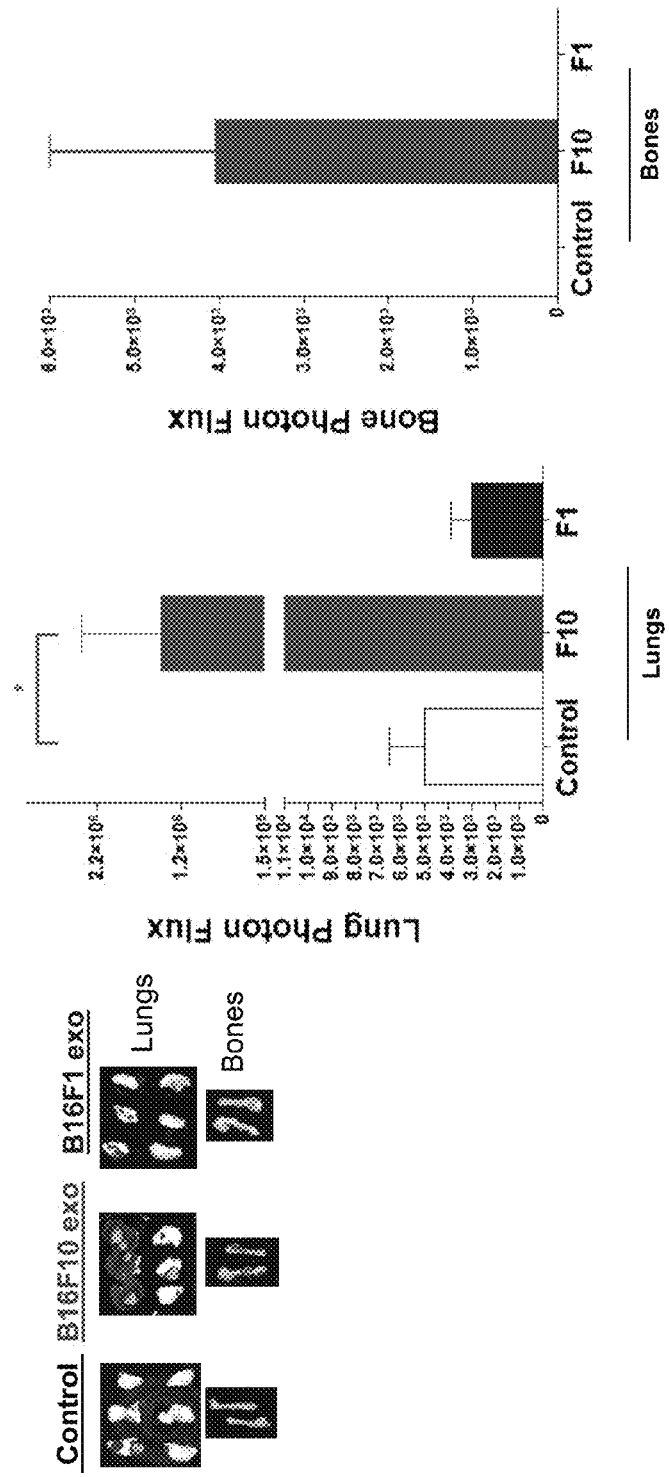
Figures 3A, 3B:
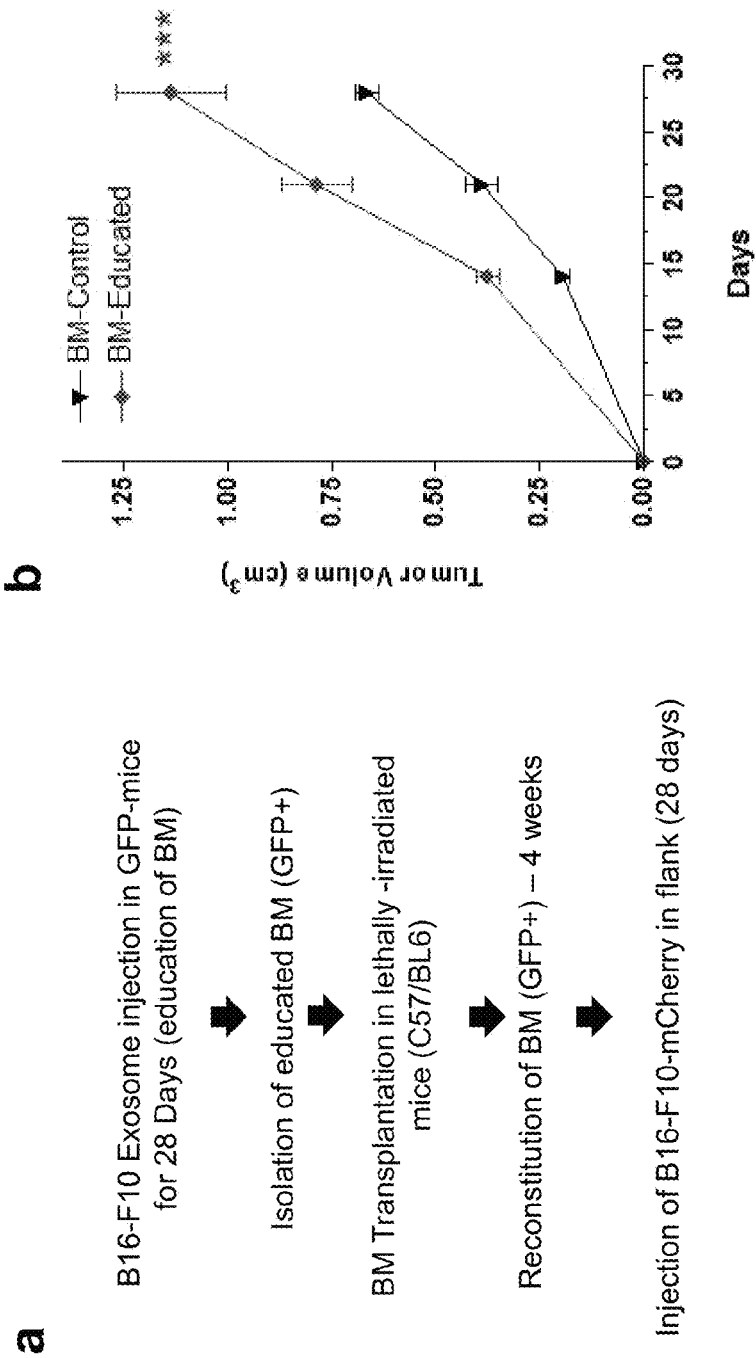
FIGS. 3A-3E show the role of tumor-derived exosomes in BM cell education and the metastatic process.

There was no significant difference in primary tumor growth observed after 21 days (FIG. 2E). Importantly, mice injected with B16-F10 exosomes had greater metastatic burden in the lung (240-fold increase measured by luciferase intensity; FIG. 2F, left graph middle bar) compared to control-treated mice or mice pre-treated with low metastatic B16-F1-derived exosomes (FIG. 2F left graph, right bar). These data suggest that qualitative differences in exosome content can mediate metastatic potential. Interestingly, the B16-F10 exosome treated animals also developed metastatic disease in atypical sites, including the bone (FIG. 2F) and brain compared to either control-treated or B16-F1-treated mice Example 3—Tumor-Derived Exosomes Enhance Metastasis by Bone Marrow Cell Education Given the importance of BMDCs in metastatic progression (Joyce & Pollard, "Microenvironmental Regulation of Metastasis," *Nat. Rev. Cancer* 9:239-252 (2009); Psaila & Lyden, "The Metastatic Niche: Adapting the Foreign Soil," *Nat. Rev. Cancer* 9:285-293 (2009), which are hereby incorporated by reference in their entirety), whether tumor-derived exosomes could 'educate' BMDCs and thereby influence the metastatic process was determined (FIG. 3A). Bone marrow from GFP mice treated with B16-F10 exosomes (BM-exosome-educated) for 28 days versus control/synthetic exosomes (BM control) was transplanted into lethally irradiated C57BL/6 WT mice. After BM reconstitution, mice were given subcutaneous implants of B16-F10mCherry cells and the contribution of "exosome-educated" BM to tumor growth and metastasis was determined. BM-exosome-educated mice had greater tumor growth compared to BM-control mice treated with synthetic exosomes (FIG. 3B) or PBS, indicating that pre-education of BM cells with tumor exosomes enhances the kinetics of primary tumor growth.

Figure 3C:
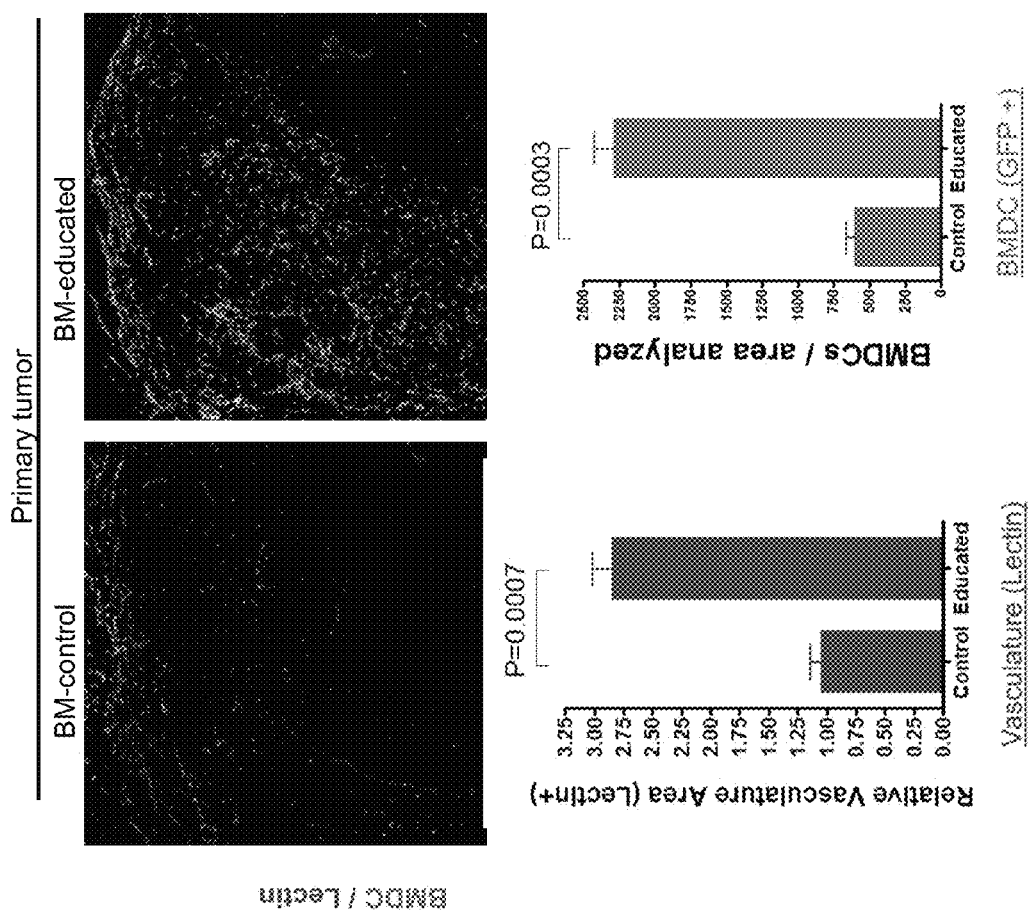
Figure 3D:
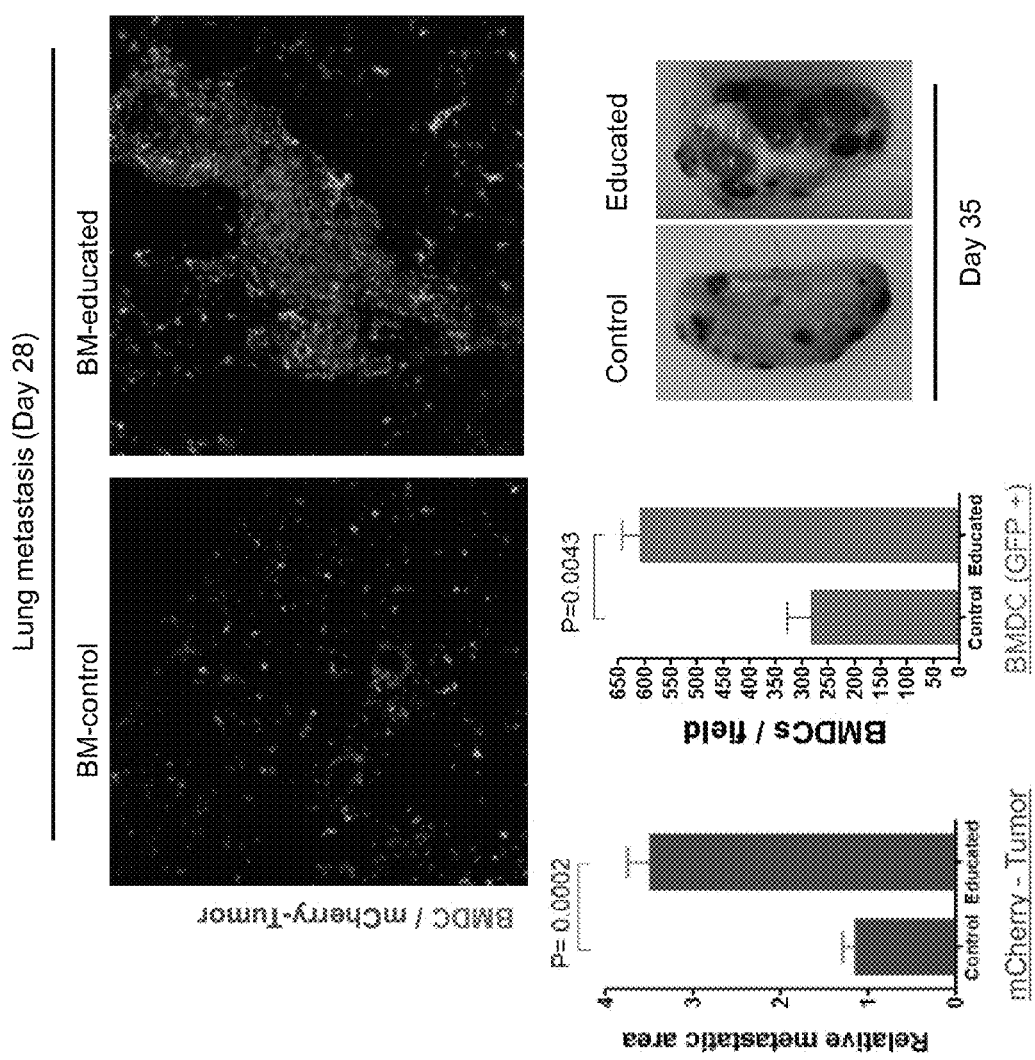

An analysis of primary tumors in these mice showed that BM cell recruitment was markedly increased in primary tumors of BM-educated mice compared to controls (FIG. 3C). Recruitment of BMDCs and tumor vasculature were enhanced by approximately 4.5-fold and 3-fold, respectively (FIG. 3C). A significant increase in the size and number of metastases at both typical (i.e., lungs and ipsilateral lymph nodes) and atypical sites (i.e., contralateral lymph nodes, mesentery, and brain) at this stage of tumorigenesis (Table 5). Quantification of lung metastases at day 28 demonstrated that BM-educated mice had a 3-fold higher metastatic burden and larger metastatic lesions compared to BM-controls (FIG. 3D). Recruitment of BMDCs to metastatic areas was also elevated approximately 3-fold in BM-educated mice (FIG. 3D). After 35 days, larger macrometastatic lesions were apparent in BM-educated mice compared to controls (FIG. 3D, lower right panels). Interestingly, analysis of BMDCs mobilized to the lung in metastatic and non-metastatic areas revealed systemic mobilization of BMDCs to metastatic organs independent of tumor cell presence, although in tumor areas the number of cells per area was significantly increased (FIG. 8B). Bone marrow cell education with B16-F10 exosomes also increased the incidence of metastases in less metastatic models, such as Lewis lung carcinoma (LLC) (FIG. 9B). In particular, mice transplanted with B16-F10 exosome-educated BM developed larger primary tumors (FIG. 9A), and the metastatic burden was increased 10-fold in the LLC model (FIG. 9B), demonstrating a crucial role for BM cell education by tumor exosomes in the regulation of tumor metastasis.

TABLE 5

Analysis of B16 metastasis by H&E staining in sections derived from different tissues of mice with B16-F10 flank tumors after transplantation with B16-F10 exosome-educated bone marrow (BM-educated) or BM-treated with control exosome particles (BM-control)

| Tissue | BM Control | BM educated |
| --- | --- | --- |
| Lung | + | +++ |
| Ipsilateral lymph nodes | + | + |
| Contralateral lymph nodes | − | ++ |
| Mesenteric metastasis | − | + |
| Brain | − | + |
| Bone marrow | − | − |

Figure 3E:
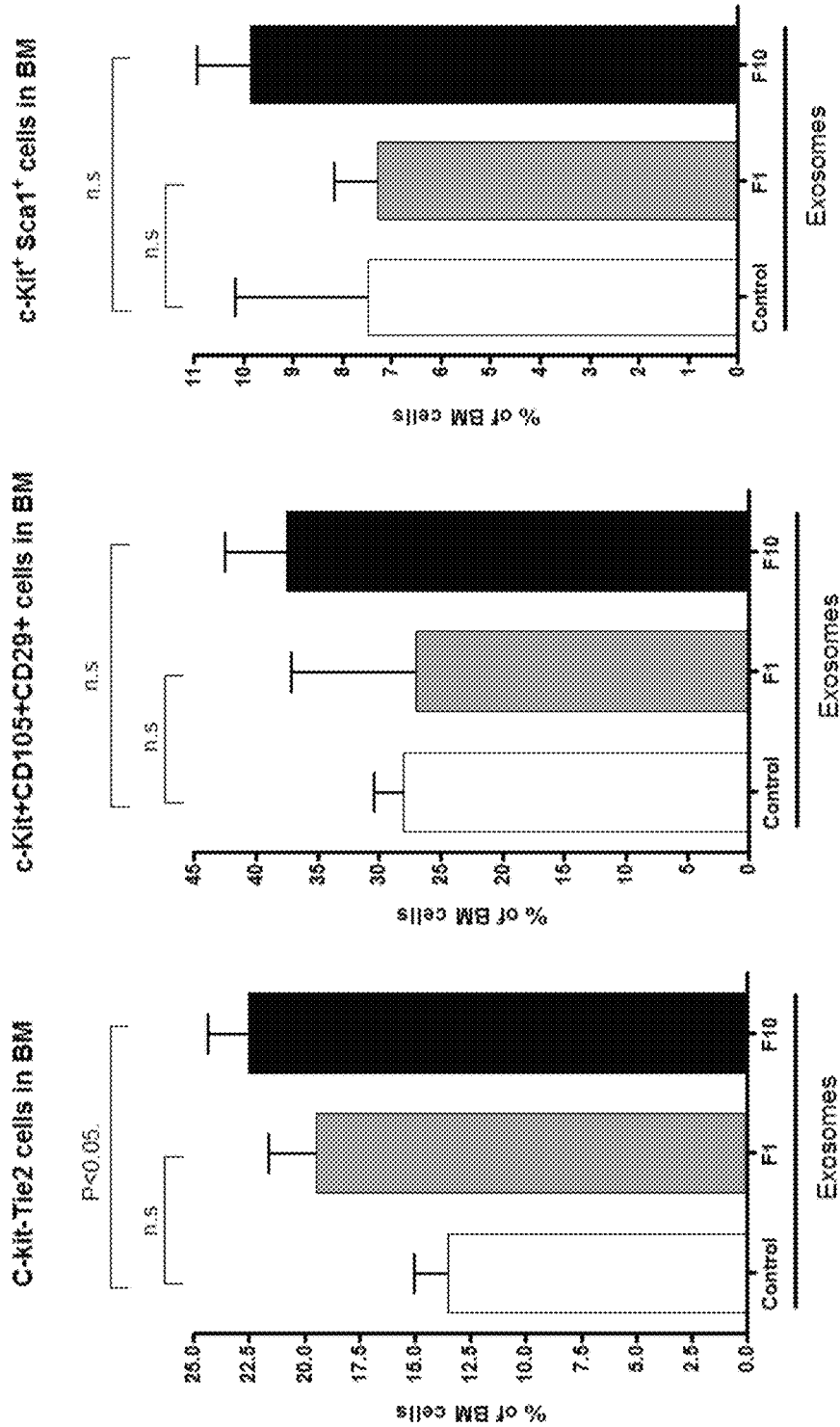

To further define the mechanisms of exosome education of BMDC, the role of B16-F10 and B16-F1 exosomes in regulating BM cell progenitor phenotype was analyzed. Bone marrow of mice treated with exosomes for 28 days as described above was isolated and analyzed by flow cytometry. Tumor exosomes promoted a 2-fold increase in the frequency of c-Kit$^+$Tie2$^+$ cells and a slight increase in CD105$^+$CD29$^+$c-Kit$^+$ cells in BM; however, the total c-Kit$^+$Sca1$^+$ population was not affected (FIG. 3E). In addition, no major differences were observed after exosome education in other BMDCs populations including CD11b, CD11b/Gr1, F4/80, or VEGFR1-expressing cells, which are commonly mobilized by growth factors and chemokines (Kaplan et al., "VEGFR1-Positive Haematopoietic Bone Marrow Progenitors Initiate the Pre-Metastatic Niche," *Nature* 438:820-827 (2005); Hiratsuka et al., "Tumour-Mediated Upregulation of Chemoattractants and Recruitment of Myeloid Cells Predetermines Lung Metastasis," *Nat. Cell. Biol.* 8:1369-1375 (2006); Hiratsuka et al., "The S100A8-Serum Amyloid A3-TLR4Paracrine Cascade Establishes a Pre-Metastatic Phase," *Nat. Cell Biol.* 10:1349-1355 (2008), which are hereby incorporated by reference in their entirety).

Example 4—MET is Horizontally Transferred and Upregulated in BM Progenitor Cells During Melanoma Progression Exosomes are known to promote horizontal transfer of molecules to recipient cells (Ratajczak et al., "Embryonic Stem Cell-Derived Microvesicles Reprogram Hematopoietic Progenitors: Evidence for Horizontal Transfer of mRNA and Protein Delivery," *Leukemia* 20:847-856 (2006); Al-Nedawi et al., "Intercellular Transfer of the Oncogenic Receptor EGFRvIII by Microvesicles Derived From Tumour Cells," *Nat. Cell Biol.* 10:619-624 (2008); Balaj et al., "Tumour Microvesicles Contain Retrotransposon Elements and Amplified Oncogene Sequences," *Nat. Commun.* 2:180 (2011), which are hereby incorporated by reference in their entirety). Given the differential effects of B16-F1 versus B16-F10 exosomes on metastatic potential (Taylor et al., "Characterization of Plasma Membrane Shedding From Murine Melanoma Cells," *Int. J. Cancer* 41:629-635 (1988), which is hereby incorporated by reference in its entirety), the proteomic profiles of these exosomes were compared and proteins that were highly expressed in the B16-F10 exosomes but present at much lower levels in the B16-F1 exosomes were identified (Table 6). Some candidates, which have a known role in tumorigenesis and metastasis include the MET oncoprotein, CD44, Hsp70 and annexin A6 (Trusolino et al., "MET Signalling: Principles and Functions in Development, Organ Regeneration and Cancer," *Nat. Rev. Mol. Cell Biol.* 11:834-848 (2010); Zoller, M., "CD44: Can a Cancer-Initiating Cell Profit From an Abundantly Expressed Molecule?" *Nat. Rev. Cancer* 11:254-267 (2011), which are hereby incorporated by reference in their entirety). Given the importance of MET signaling in migration, invasion, angiogenesis and BM cell mobilization (Trusolino et al., "MET Signalling: Principles and Functions in Development, Organ Regeneration and Cancer," *Nat. Rev. Mol. Cell Biol.* 11:834-848 (2010); Stella et al., "Targeting the MET Oncogene in Cancer and Metastases," *Expert Opin. Investig. Drugs* 19:1381-1394 (2010); Jalili et al., "The HGF/c-Met Axis Synergizes With G-CSF in the Mobilization of Hematopoietic Stem/Progenitor Cells," *Stem Cells Dev.* 19:1143-1151 (2010); Tesio et al., "Enhanced c-Met Activity Promotes G-CSF-Induced Mobilization of Hematopoietic Progenitor Cells Via ROS Signaling," *Blood* 117:419-428 (2011), which are hereby incorporated by reference in their entirety), a functional analyses of this proto-oncogene was done. It was hypothesized that MET was horizontally transferred from the melanoma tumor to BM progenitor cells through exosomes, representing a new mechanism promoting metastatic progression. The increase in MET and phospho-MET (Tyr 1234/1235) levels was verified in both B16-F10 exosomes and cells compared to B16-F1 (FIG. 4A). Analysis of MET expression in BM Lin-progenitor cells after exosome education for 28 days demonstrated that MET expression was upregulated in BM progenitor cells from mice injected with B16-F10 exosomes (FIG. 4B) but not in the B16-F1 group. Notably, CD44 levels were not affected by treatment with either B16-F10 or B16-F1 exosomes (FIG. 4B).

TABLE 6

Proteins shed in B16-F10 exosomes compared to B16-F1 by Mass Spectrometry

| PROTEIN | MW | ACCESSION |
|---|---|---|
| AF4/FMR2 family, member 2 | 140072.4 | 153792808 |
| Annexin A1 | 38710 | 124517663 |
| Annexin A11 | 54076.8 | 160707921 |
| Annexin A2 | 38651.9 | 6996913 |
| Annexin A6 | 75837.5 | 31981302 |
| Basigin isoform 2 | 29656 | 116014342 |
| Cadherin EGF LAG seven-pass G-type receptor 3 | 358252 | 125719165 |
| Catenin (cadherin associated protein), delta 1 | 104860 | 83745122 |
| CD44 antigen isoform a | 85785.7 | 85540471 |
| CD47 antigen | 35293.8 | 6754382 |
| Cell division cycle 42 homolog | 21245 | 6753364 |
| Enolase 3, beta muscle | 46995.4 | 6679651 |
| Growth arrest specific 7 | 48143.3 | 157817137 |
| Heat shock 70 kDa protein 1-like] | 70593.3 | 124339838 |
| Heat shock protein 4 | 94149.3 | 112293266 |
| Hsp90ab1 - heat shock protein 1, alpha | 84734.8 | 6754254 |
| Integrin beta 6 | 85985.1 | 10946686 |
| Junction plakoglobin | 81748.9 | 28395018 |
| Keratin 13 | 47724.3 | 6754480 |
| Keratin 17n | 50146 | 154090941 |
| Keratin complex 2, basic, gene 25 | 54621.6 | 269914157 |
| Keratin complex 2, basic, gene 35 | 56715 | 47523977 |
| Keratin complex 2, basic, gene 5 | 61728.6 | 20911031 |
| Keratin complex 2, basic, gene 6a | 59298.7 | 54607171 |
| LR8 protein | 28348.6 | 12746434 |
| Met proto-oncogene | 153450.3 | 146198696 |
| Nicastrin | 78440.7 | 224809376 |
| Protein kinase C and casein kinase substrate in neurons 2 | 55798.3 | 7106381 |
| RAB7, member RAS oncogene family | 23543.9 | 148747526 |
| Sequestosome 1 | 48132.2 | 6754954 |
| Tax1 binding protein 1 homolog | 93528.5 | 256773241 |
| TNF receptor-associated protein 1 | 80158.7 | 13385998 |
| Tumor rejection antigen gp96 | 92418.1 | 6755863 |
| Tumor susceptibility gene 101 protein | 44095.6 | 11230780 |
| Tyrosine 3-monooxygenase/tryptophan 5-monooxygenase activation protein, zeta polypeptide | 27753.7 | 6756041 |
| Vesicle amine transport protein 1 homolog (*T californica*) | 43069 | 33859662 |
| Vinculin | 116644.4 | 31543942 |

To determine the functional consequences of MET expression within exosomes, MET levels were reduced by 40% and phospho-MET levels were reduced by 80% using MET shRNAs introduced into B16-F10 cells (FIG. 10A). The potential transfer of MET from exosomes to BM progenitor cells was analyzed by exposing BM cells to fluorescently-labeled (PKH26-red dye) exosomes from B16-F10, B16-F10-shMET and B16-F1 cells. A 6.29-fold increase in c-Kit⁺MET⁺ BM progenitor cells was observed after treatment with B16-F10 exosomes compared to treatment with B16-F10-shMET, B16-F1, and control exosomes as demonstrated by FACS analysis and immunofluorescence (FIG. 4C and FIG. 10B). Additionally, 92% of the MET⁺ BM cells also expressed the fluorescent exosome-specific marker (PKH26⁺) demonstrating horizontal transfer of MET from exosomes to BM cells (FIG. 4C right inset, red line). In contrast, BM cells treated with either B16-F1 or B16-F10shMET exosomes did not express MET, while exosome uptake was not significantly affected, as denoted by PKH26-red dye fluorescence (FIG. 4C right inset, blue and green lines, respectively). In order to determine whether B16-F10 exosomes contribute to MET pathway activation, the phosphorylation of down-stream mediators of HGF/MET signaling previously demonstrated to play a role in BM progenitor cell mobilization (Jalili et al., "The HGF/c-Met Axis Synergizes With G-CSF in the Mobilization of Hematopoietic Stem/Progenitor Cells," *Stem Cells Dev.* 19:1143-1151 (2010); Tesio et al., "Enhanced c-Met Activity Promotes G-CSF-Induced Mobilization of Hematopoietic Progenitor Cells Via ROS Signaling," *Blood* 117:419-428 (2011), which are hereby incorporated by reference in their entirety), such as phospho S6-kinase (mTOR pathway) and phospho-ERK (MAPK pathway) was analyzed. A 16-hour pre-treatment of BM cells with B16-F10 exosomes promoted the phosphorylation of both S6-kinase (Ser371) and ERK (Tyr202/204) in response to HGF (5 ng/ml for 4 hours) compared to control cells that had not been treated with exosomes (FIG. 10C). In contrast, pre-treatment with B16-F1 exosomes did not promote the activation of these pathways in response to HGF, as they lack the MET receptor (FIG. 10C). Additionally, pre-treatment with a MET inhibitor (Crizotinib, 20 nM) before HGF addition blocked the phosphorylation of S6-kinase and ERK after F10 exosome treatment, demonstrating the specificity of this pathway (FIGS. 15A-15B).

'Exosome education' studies demonstrated that, compared to control and B16-F1 exosomes, B16-F10 exosomes did not alter the relative expression of MET in angiogenic progenitor cells (c-Kit⁺Tie2⁺) in BM but MET+ cells were significantly increased in the peripheral circulation (FIG. 4D) as well as in hematopoietic progenitor cells (c-Kit⁺-Sca1⁺MET⁺) (FIG. 10D), suggesting that MET expression led to enhanced BM cell mobilization. To determine the effects of exosome-dependent MET signaling on primary tumor growth and metastasis, B16-F10 tumor cells were implanted in mice educated with B16-F10 exosomes having silenced MET (B16-F10-shMET) and controls. While no difference was observed in primary tumor growth, mice educated with B16-F10-shMET exosomes had reduced lung and bone metastasis compared to mice educated with B16-F10 exosomes (FIG. 4E). This finding correlated with a decrease in angiogenic and hematopoietic precursors in the BM and peripheral blood of B16-F10-shMET exosome educated mice bearing B16-F10 tumors.

To determine the relevance of these findings to human melanoma, the levels of MET and phospho-MET in circulating exosomes isolated from stage III and IV melanoma patients (cohort previously described in FIG. 1) were measured. Higher levels of total and phospho-MET were found in both stage III and IV melanoma patients compared to control subjects (FIG. 4F). MET expression was also increased in both BM progenitor cells (CD45⁻CD117$^{low/+}$) and pro-vasculogenic/angiogenic cells (CD45⁻CD117$^{low/+}$ TIE2⁺) isolated from the peripheral blood of patients with Stage I-III and IV disease compared to control subjects (FIG. 4G and FIG. 10E). This data indicates that MET expression in circulating exosomes and BM progenitor cells is a new predictor or early marker of metastatic disease.

Example 5—Rab27a, a New Target to Reduce Exosomes and Metastasis

As Ras-related Rab proteins are key elements of the molecular machinery that controls membrane trafficking (Stenmark, H., "Rab GTPases as Coordinators of Vesicle Traffic," *Nat. Rev. Mol. Cell. Biol.* 10:513-525 (2009), which is hereby incorporated by reference in its entirety), the role of Rab genes in the exosome production pathway was examined using a panel of melanoma cell lines derived from patients. qRT-PCR was employed to analyze the expression of Rab1a, Rab5a, Rab5b, Rab7, Rab27a, and Rab27b in 30 melanoma cells lines and compare this expression to that in human breast cancer and pancreatic adenocarcinoma cell lines (FIG. 5A). Analysis of these genes revealed that cell lines secreting high levels of exosomes, such as SK-Mel28 and SK-Mel202 (FIG. 5B, black bars), expressed high levels of Rab27a, Rab5b, and Rab7 and moderate levels of Rab1a (FIG. 5A). However, melanoma cell lines such as SK-Mel191 or SK-Mel131 secreted lower amounts of exosomes (FIG. 5B, white bars), and had low or intermediate expression of these Rab transcripts (FIG. 5A), similar to what was observed for several breast (MCF-7, MDA-MB-231, SkBr3) or pancreatic carcinoma-derived cell lines (AsPc1) (FIG. 5A).

Since the RAB27 gene has recently been described as critical for exosome release (Ostrowski et al., "Rab27a and Rab27b Control Different Steps of the Exosome Secretion Pathway," *Nat. Cell Biol.* 12:19-30; (2009), which is hereby incorporated by reference in its entirety) specifically, without affecting other secretion pathways, this gene was further investigated as a possible target for blocking exosome production in melanoma cells. Analysis of Rab27a and Rab27b isoforms in melanoma cell lines demonstrated that Rab27a was the only isoform expressed in B16-F10 and SK-Mel28 cells (FIG. 5A). Expression of Rab27a was knocked down by lentiviral transduction of shRNAs in both SK-Mel28 and B16-F10 melanoma cells and the resultant exosome synthesis was examined. Knockdown of Rab27a reduced the expression of Rab27a by approximately 90% in the B16-F10 cell line and 70% in the SK-Mel28 cell line (FIG. 5C). Analysis of exosome secretion in these cell lines showed an approximately 50% reduction in exosome release in both models (FIG. 5D and FIG. 11A), demonstrating a role for Rab27a in exosome production by melanoma cells. No significant differences in total protein, protein content, exosome-specific markers or MET/phospho-MET were observed in either the melanoma cells or exosomes from either shRab27a or shScramble cells (FIGS. 11A, 11B, and 11C). Additionally, an analysis of secreted angiogenic factors from these matched cell lines (shScamble versus shRab27a B16-F10) revealed a decrease in P/GF-2, PDGF-AA and osteopontin as a consequence of reducing Rab27a levels (FIG. 5E). Analysis of B16-F10 primary tumors after flank injection demonstrated a 60% reduction in tumor volume after Rab27a knockdown (FIG. 5E). Moreover, Rab27a knockdown significantly blocked the progression of lung micro- and macrometastases (FIGS. 5E and 5F). Consistent with exosomes 'educating' the BM, the decrease in both primary tumor size and metastatic progression was associated with a decrease in BMDCs recruited to both in the primary tumor and at metastatic sites (FIG. 5F). Similarly, knockdown of Rab27a in SK-Mel28 led to a 50% reduction of primary tumor growth (FIG. 5E) and an 80% reduction in metastatic disease in the lung (FIG. 5E). Consistent with previous experiments (FIG. 8A), the total exosome numbers were never above control levels in the Rab27a knockdown tumor bearing mice, as these tumors never exceeded 1.2 cm by 21 days. These data suggest that the contribution of tumor-derived exosomes in Rab27a knockdown tumor bearing mice was minimal in the circulation and therefore insufficient to educate and mobilize bone marrow derived cells (FIG. 5G).

The growth of lung metastases following tail vein injection (lung colonization) was examined, and both B16-F10 and SK-Mel28 Rab27 knockdown cells had a 90% and 70%, reduction, respectively, in metastatic lung colonies (FIG. 11D). Furthermore, after injection of increasing concentrations of exosomes isolated from B16-F10-shScramble and B16-F10-shRab27a cell lines into mice followed by flank injection of tumor cells, a dose-dependent increase in metastatic burden was observed (FIGS. 12A-12B). These data indicate that quantitative differences in exosome production can alter the metastatic potential. Collectively, these data suggest that Rab27a knockdown in melanoma models reduced exosome production and circulating exosome levels, preventing the recruitment of specific BMDCs that are necessary for metastatic progression.

Example 6—the Protein Content of Circulating Exosomes is Increased in a Variety of Cancers Example 1 above demonstrates the levels of exosome proteins is higher in patients with Stage IV melanoma disease compared to normal controls as well as patients with less advanced disease (FIG. 6B). To further validate these data in other cancer patients, the protein content of exosomes isolated from lung, colon, pancreas and glioblastoma cancer patients was analyzed. The protein content per exosome is increased in these cancer patients as compared to controls (FIGS. 13A-13B). Similarly, the proteins per milliliter of plasma in the exosomes isolated from cancer patients was increased (FIGS. 14A-14B). These data suggest that there is a qualitative difference in protein content in exosomes isolated from patients with metastatic disease.

Discussion of Examples 1-6

Increasing evidence has emerged indicating that exosomes are mediators of tumorigenesis including pre-metastatic niche formation, recruitment of myeloid derived suppressor cells and preparation of sentinel lymph nodes for future metastasis (Ratajczak et al., "Membrane-Derived Microvesicles: Important and Underappreciated Mediators of Cell-to-Cell Communication," Leukemia 20:1487-1495 (2006); Liu et al., "Contribution of MyD88 to the Tumor Exosome-Mediated Induction of Myeloid Derived Suppressor Cells," Am. J. Pathol. 176:2490-2499 (2010); Al-Nedawi et al., "Intercellular Transfer of the Oncogenic Receptor EGFRvIII by Microvesicles Derived From Tumour Cells," Nat. Cell Biol. 10:619-624 (2008); Skog et al., "Glioblastoma Microvesicles Transport RNA and Proteins That Promote Tumour Growth and Provide Diagnostic Biomarkers," Nat. Cell Biol. 10:1470-1476 (2008); Hood et al., "Exosomes Released by Melanoma Cells Prepare Sentinel Lymph Nodes for Tumor Metastasis," Cancer Res. 71:3792-3801 (2011); Jung et al., "CD44v6 Dependence of Premetastatic Niche Preparation by Exosomes," Neoplasia 11:1093-1105 (2009); Lima et al., "Tumor-Derived Microvesicles Modulate the Establishment of Metastatic Melanoma in a Phosphatidylserine-Dependent Manner," Cancer Lett. 283:168-175 (2009), which are hereby incorporated by reference in their entirety). The role of exosomes in malignant melanoma has recently been explored revealing increased expression of CD63 or caveolin-1 in melanoma patients compared to healthy controls (Logozzi et al., "High Levels of Exosomes Expressing CD63 and Caveolin-1 in Plasma of Melanoma Patients," PLoS One 4:e5219 (2009), which is hereby incorporated by reference in its entirety). However, the molecular and cellular mechanisms underlying these associations have not been determined.

As described herein, exosomes play a role in tumor progression and pre-metastatic niche formation that is distinct from that of tumor-derived growth factors, extracellular proteins and chemokines such as VEGF-A, P/GF, TGF-β, TNF-α, LOX and Tenascin C (Kaplan et al., "VEGFR1-Positive Haematopoietic Bone Marrow Progenitors Initiate the Pre-Metastatic Niche," Nature 438:820-827 (2005); Erler et al., "Hypoxia-Induced Lysyl Oxidase is a Critical Mediator of Bone Marrow Cell Recruitment to Form the Premetastatic Niche," Cancer Cell 15:35-44 (2009); Hiratsuka et al., "Tumour-Mediated Upregulation of Chemoattractants and Recruitment of Myeloid Cells Predetermines Lung Metastasis," Nat. Cell. Biol. 8:1369-1375 (2006); Hiratsuka et al., "The S100A8-Serum Amyloid A3-TLR4 Paracrine Cascade Establishes a Pre-Metastatic Phase," Nat. Cell Biol. 10:1349-1355 (2008); Oskarsson et al., "Breast Cancer Cells Produce Tenascin C as a Metastatic Niche Component to Colonize the Lungs," Nat. Med. 17:867-874 (2011); Psaila et al., "Priming the 'Soil' for Breast Cancer Metastasis: The Pre-Metastatic Niche," Breast Dis. 26:65-74 (2006), which are hereby incorporated by reference in their entirety). Tumor-derived exosomes circulate in the plasma promoting the 'education' and mobilization of BM cells to the peripheral circulation, primary tumor, and metastatic microenvironments where they support tumor vasculogenesis, invasion, and metastatic progression. Furthermore, tumor-derived exosomes also recruit BMDCs indirectly by the up-regulation of pro-inflammatory molecules, such as S100a8, S100a9 and TNF-α at pre-metastatic sites in the lung. Thus tumor-derived exosomes appear to be responsible for the recruitment of BMDCs to pre-metastatic niches via direct and indirect mechanisms. Multiple cell types, including fibroblasts, endothelial cells, and BM progenitor cells, contribute to the generation of tumor and metastatic microenvironments, (Joyce & Pollard, "Microenvironmental Regulation of Metastasis," Nat. Rev. Cancer 9:239-252 (2009); Guise, T., "Examining the Metastatic Niche: Targeting the Microenvironment," Semin. Oncol. 37 Suppl 2:S2-14 (2010), which are hereby incorporated by reference in their entirety) and may be influenced by horizontal transfer of molecules (i.e. proteins and miRNAs) by exosomes (Ratajczak et al., "Embryonic Stem Cell-Derived Microvesicles Reprogram Hematopoietic Progenitors: Evidence for Horizontal Transfer of mRNA and Protein Delivery," Leukemia 20:847-856 (2006); Balaj et al., "Tumour Microvesicles Contain Retrotransposon Elements and Amplified Oncogene Sequences," Nat. Commun. 2:180 (2011); Aliotta et al., "Microvesicle Entry Into Marrow Cells Mediates Tissue-Specific Changes in mRNA by Direct Delivery of mRNA and Induction of Transcription," Exp. Hematol. 38:233-245 (2010); Aliotta et al., "Alteration of Marrow Cell Gene Expression, Protein Production, and Engraftment Into Lung by Lung-Derived Microvesicles: A Novel Mechanism for Phenotype Modulation," Stem Cells 25:2245-2256 (2007), which are hereby incorporated by reference in their entirety).

The work described herein demonstrates that tumor exosomes derived from highly metastatic melanoma cell lines (B16-F10) increased the metastatic behavior of primary tumors, while tumor exosomes derived from low-metastatic melanoma cells (B16-F1) did not alter the incidence of metastases.

As shown herein, MET and phospho-MET are preferentially expressed in highly metastatic B16-F10- and human primary melanoma cell line-derived exosomes compared to the low-metastatic B16-F1 exosomes. Exosome-derived MET was transferred to BM progenitor cells, promoting their 'education' to a pro-vasculogenic phenotype and enhancing their mobilization to the peripheral circulation (FIGS. 4A-4E). Interestingly B16-F10-derived exosomes activated HGF-dependent mTOR and MAPK signaling in BM cells (FIG. 10C), suggesting a crucial role for MET activation in BM cell mobilization during metastasis. Reducing MET expression in tumor-derived exosomes led to decreased horizontal transfer and expression of this receptor in BM cells, diminishing the pro-vasculogenic 'education' and egress of these cells to the circulation. Therefore, tumor-derived exosome composition (e.g. MET expression) 'educates' specific BM progenitor cell populations and, thus, has a direct impact on metastatic propensity and outcome.

Boccacio et. al., have previously described the MET oncogene as playing dual roles in cancer formation (Boccaccio & Comoglio, "Invasive Growth: A MET-Driven Genetic Programme for Cancer and Stem Cells," *Nat. Rev. Cancer* 6:637-645 (2006), which is hereby incorporated by reference in its entirety). First, as a transforming oncogene, MET can regulate clonal selection in tumor onset. Second, MET signaling leads to tumor cell proliferation, survival, motility and invasion, and metastasis in a large number of solid and hematologic malignancies (Peruzzi & Bottaro, "Targeting the c-Met Signaling Pathway in Cancer," *Clin. Cancer Res.* 12:3657-3660 (2006); Birchmeier et al., "Met, Metastasis, Motility and More," *Nat. Rev. Mol. Cell Biol.* 4:915-925 (2003); Scott et al., "Proinvasion Metastasis Drivers in Early-Stage Melanoma Are Oncogenes," *Cancer Cell* 20:92-103 (2011); Christensen et al., "c-Met as a Target for Human Cancer and Characterization of Inhibitors for Therapeutic Intervention," *Cancer Lett.* 225:1-26 (2005), which are hereby incorporated by reference in their entirety). A third role for exosome-packaged MET involves it acting as an effector of exosome function, through which exosomes from highly metastatic melanoma dictate the generation of pro-metastatic phenotypes of BM hematopoietic progenitor cells that enhance metastatic progression. Although the melanoma-derived exosomes influenced the BM progenitor cell population predominantly, it is possible that exosomes from other tumor types may 'educate' other bone marrow stem and progenitor populations.

Tumor-derived exosomes can reprogram BMDCs (e.g., increase in the frequency of c-Kit$^+$Tie2$^+$ BM progenitor cells), resulting in increased tumor neovascularization (FIG. 3). In addition to Tie2-expressing endothelial cells and hematopoietic progenitor cells (HPCs), myeloid lineage cells known as Tie2-expressing monocytes (TEMs) (De Palma et al., "Tie2-Expressing Monocytes: Regulation of Tumor Angiogenesis and Therapeutic Implications," *Trends Immunol.* 28:519-524 (2007); Coffelt et al., "Angiopoietin-2 Regulates Gene Expression in TIE2-Expressing Monocytes and Augments Their Inherent Proangiogenic Functions," *Cancer Res.* 70:5270-5280 (2010), which are hereby incorporated by reference in their entirety) have been shown to be essential for vasculogenesis and angiogenesis (De Palma et al., "Tie2 Identifies a Hematopoietic Lineage of Proangiogenic Monocytes Required for Tumor Vessel Formation and a Mesenchymal Population of Pericyte Progenitors," *Cancer Cell* 8:211-226 (2005), which is hereby incorporated by reference in its entirety). Notably, MET was also found upregulated in mobilized c-Kit$^+$Tie2$^+$ and Lin$^-$Kit$^+$Sca-1$^+$ BM progenitor cells but not in BM (FIG. 4D). These findings are consistent with data from other studies demonstrating that MET over-expression in BM cells can lead to BM cell mobilization (Jalili et al., "The HGF/c-Met Axis Synergizes With G-CSF in the Mobilization of Hematopoietic Stem/Progenitor Cells," *Stem Cells Dev.* 19:1143-1151 (2010); Tesio et al., "Enhanced c-Met Activity Promotes G-CSF-Induced Mobilization of Hematopoietic Progenitor Cells Via ROS Signaling," *Blood* 117:419-428 (2011), which are hereby incorporated by reference in their entirety). The Examples herein also determined that B16-F10 exosome-educated BM promoted metastatic progression with increased tumor burden and evidence of disease in sites rarely involved (e.g. mesentery, contralateral lymph nodes, and brain). In addition, mice educated with B16-F10 exosomes and then implanted with cells of the less metastatic LLC model exhibited enhanced metastatic disease throughout the lung. Interestingly, the BM in mice 'educated' with the low-metastatic B16-F1 exosomes, which lacked the MET receptor, reduced metastasis (not statistically significant) in the implanted highly metastatic B16-F10 primary tumors.

The molecular mechanisms of exosome biogenesis and secretion are poorly described and the expression pattern of molecules regulating exosome secretion in specific diseases is not yet well understood. Here, is described for the first time the analysis of 6 different genes potentially related to exosome secretion in 30 melanoma cell lines derived from melanoma patients (FIG. 5). Melanoma cell lines that secrete high levels of exosomes express high levels of Rab27a, Rab5b, and Rab7 and moderate levels of Rab1a. Rab27a has been implicated in the abnormal regulation of protein trafficking in melanoma, and Rab27 isoforms have been found to control exosome pathways in other systems (Ostrowski et al., "Rab27a and Rab27b Control Different Steps of the Exosome Secretion Pathway," *Nat. Cell Biol.* 12:19-30; (2009); Akavia et al., "An Integrated Approach to Uncover Drivers of Cancer," *Cell* 143:1005-1017 (2010), which are hereby incorporated by reference in their entirety). As shown herein, melanoma cells treated with Rab27a shRNA exhibited decreased exosome production as well as decreased levels of pro-angiogenic factors (P/GF-2, osteopontin and PDGF-AA) from tumor cells, hindering BMDC mobilization and thereby preventing tumor growth and nearly abrogating metastasis (FIG. 5). Interestingly, Rab27a and Rab27b overexpression has been correlated with increased invasion and metastatic phenotype in breast cancer cell lines indicating that Rab27a proteins may play an active role in malignancy (Wang et al., "Enhanced Expression of Rab27A Gene by Breast Cancer Cells Promoting Invasiveness and the Metastasis Potential by Secretion of Insulin-Like Growth Factor-II," *Mol. Cancer Res.* 6:372-382 (2008); Hendrix et al., "Effect of the Secretory Small GTPase Rab27B on Breast Cancer Growth, Invasion, and Metastasis," *J. Nat'l Cancer Inst.* 102:866-880 (2010), which are hereby incorporated by reference in their entirety). Therefore, Rab27a should be considered as a potential target for novel combination therapies designed to prevent melanoma metastasis by blocking release of tumor-derived exosomes and/or soluble angiogenic factors and inhibiting the recruitment of specific BMDCs. Of note, Rab proteins such as Rab27a, Rab5, or Rab7, were not present in the exosomes isolated from melanoma patients, in contrast to human melanoma cells. This observation indicates that, while Rab proteins may be important for exosome synthesis, they are not necessarily packaged into the exosomes themselves.

The studies described herein involving melanoma patients supports a model in which the specific protein composition of circulating plasma exosomes could be used as a molecular signature in the clinical setting, not only as an indicator of widespread metastatic disease, but also as a predictive factor for metastatic potential. In a prospective blinded study, exosomes from patients with Stage I to Stage IV melanoma were compared to normal controls (FIGS. 1B and 1C). The results indicated that exosomes derived from Stage IV melanoma patients, compared to exosomes from Stage I patients and normal controls, expressed higher levels of TYRP2, VLA-4, Hsp70, a specific Hsp90 isoform and MET oncoprotein (FIG. 1 and FIG. 4). These findings support the identification of a novel 'melanoma signature' that could be used to diagnose distant metastatic disease and potentially monitor treatment response. Additionally, TYRP2 and MET are highly expressed in the exosomes derived from patients with Stage III disease with lymph node involvement. Based on a retrospective study (FIG. 1D), it was determined that the co-expression of TYRP2 and the MET oncoprotein predicted disease progression. Furthermore, MET expression is elevated in circulating $CD45^-CD117^{low/+}$ and pro-vasculogenic/angiogenic $CD45^-CD117^{low/+}TIE2^+$ progenitors in the blood of metastatic melanoma patients compared to normal controls (FIG. 4). Thus, a novel panel of exosomal proteins and BM progenitor cells in the blood of patients representative of metastatic disease have been identified that have prognostic value for patients with melanoma.

Membrane microvesicles of cancer cells have previously been suggested to contribute to a horizontal propagation of oncogenes and genetic material (Al-Nedawi et al., "Intercellular Transfer of the Oncogenic Receptor EGFRvIII by Microvesicles Derived From Tumour Cells," *Nat. Cell Biol.* 10:619-624 (2008); Balaj et al., "Tumour Microvesicles Contain Retrotransposon Elements and Amplified Oncogene Sequences," *Nat. Commun.* 2:180 (2011), which are hereby incorporated by reference in their entirety). For example, exosomes have been described to transfer their contents (mRNA, small RNAs, and proteins) to recipient cells in vitro (Valadi et al., "Exosome-Mediated Transfer of mRNAs and microRNAs is a Novel Mechanism of Genetic Exchange Between Cells," *Nat. Cell Biol.* 9:654-659 (2007); Ratajczak et al., "Embryonic Stem Cell-Derived Microvesicles Reprogram Hematopoietic Progenitors: Evidence for Horizontal Transfer of mRNA and Protein Delivery," *Leukemia* 20:847-856 (2006); Hao et al., "Epigenetic Transfer of Metastatic Activity by Uptake of Highly Metastatic B16 Melanoma Cell-Released Exosomes," *Exp. Oncol.* 28:126-131 (2006); Balaj et al., "Tumour Microvesicles Contain Retrotransposon Elements and Amplified Oncogene Sequences," *Nat. Commun.* 2:180 (2011); Aliotta et al., "Microvesicle Entry Into Marrow Cells Mediates Tissue-Specific Changes in mRNA by Direct Delivery of mRNA and Induction of Transcription," *Exp. Hematol.* 38:233-245 (2010), which are hereby incorporated by reference in their entirety). However, the work described in the Examples herein is the first to demonstrate that transfer of the MET oncoprotein from tumor-derived exosomes to non-tumor cell types, specifically BM stem and progenitor cells that collaborate in the metastatic process in vivo. Importantly, it has been demonstrated that exosomes can alter the BM in a durable or 'permanent' manner in that these BM cells retain the 'educated' phenotype following engraftment into a new host (FIG. 3). Thus, it is likely that exosomes could also induce epigenetic and genetic changes that alter the gene expression profile of BM progenitor cells and these changes would be maintained following BM transplantation. This data has important clinical implications since patients with a prior cancer diagnosis may also have permanent exosome-educated BM cells that are primed to support the metastatic potential of a secondary cancer.

Herein is described a novel mechanism that controls metastatic progression through the crosstalk between tumor-derived exosomes and BM progenitor cells. Specifically, exosome-mediated transfer of the oncoprotein MET was identified as a key regulator of BM 'education', mobilization, and metastatic progression. Collectively, this data indicate that tumor-derived exosomes promote BMDC mobilization through MET upregulation, favoring a pro-metastatic outcome. From a simple blood test, the tumor-derived exosomal signature can be used as a potential metastatic indicator. In addition to blocking exosome production in tumor cells, novel therapies designed to target the unique proteins expressed on exosomes, preventing exosomal protein transfer to BM progenitor cells and thus their 'education' during the metastatic process are warranted.

Although the invention has been described in detail for the purpose of illustration, it is understood that such detail is solely for that purpose, and variations can be made therein by those skilled in the art without departing from the spirit and scope of the invention which is defined in the following claims.

What is claimed is:

1. A method of measuring total protein content per exosome in a subject having metastatic cancer comprising:
   obtaining a sample from the subject having metastatic cancer;
   isolating exosomes from the sample;
   passing the isolated exosomes through a machine suitable for counting the number of isolated exosomes from the sample;
   contacting the isolated exosomes with reagents suitable to measure total protein content in the isolated exosomes; and
   measuring the total protein content per exosome based on said passing and said contacting.

2. A method of predicting metastasis in a subject having melanoma comprising:
   obtaining isolated exosomes from the subject;
   contacting the isolated exosomes with two or more antibodies selected from the group consisting of an anti-MET antibody, an anti-TYRP2 antibody, an anti-VLA-4 antibody, an anti-Hsp-90 antibody, and an anti-Hsp-70 antibody, wherein said antibodies bind to their respective target protein, if expressed by the isolated exosomes, to form two or more different antibody-target protein complexes;
   detecting the two or more different antibody-target protein complexes formed as a result of said contacting;
   quantifying amounts of the two or more different antibody-target protein complexes formed based on said detecting;
   determining the difference in the quantified amounts of the two or more different antibody-target protein complexes formed in the isolated exosomes and amounts of the two or more different antibody-target protein complexes in a reference exosome sample; and predicting metastasis in the subject having melanoma based on said determining, wherein an increased amount of the two or more different antibody-target protein complexes in the isolated exosomes relative to the reference exosome sample predicts metastasis in the subject.

3. A method of predicting the occurrence of metastatic melanoma in a subject, said method comprising:

obtaining a peripheral blood cell sample from a subject having melanoma;

contacting the peripheral blood cell sample with a collection of antibodies, said collection comprising an anti-MET antibody, an anti-CD45 antibody, and an anti-CD117 antibody, wherein the collection of antibodies bind to their respective target proteins, if present in the sample;

detecting cells in the sample that are positive for CD117 and MET expression (CD117$^+$/MET$^+$), but negative for CD45 expression (CD45$^-$) based on said contacting;

quantifying the number of cells in the sample that are CD117$^+$/MET$^+$/CD45$^-$ based on said detecting;

determining the difference between the number of cells in the peripheral blood cell sample from the subject that are CD117$^+$/MET$^+$/CD45$^-$ and the number of cells that are CD117$^+$/MET$^+$/CD45$^-$ in a reference peripheral blood cell sample; and predicting the occurrence of metastatic melanoma in said subject based on said determining, wherein an increase in the number of peripheral cells that are CD117$^+$/MET$^+$/CD45$^-$ in the sample from the subject relative to the reference cell sample predicts the occurrence of metastatic melanoma.

4. The method according to claim 3, wherein the collection of antibodies further comprises an anti-TIE2 antibody and said predicting involves detecting and quantifying the number of cells in the peripheral blood sample that are positive for CD117, MET, and TIE2 but negative for CD45, wherein an increase in the number of cells positive for CD117, MET, and TIE2 but negative for CD45 in the peripheral blood sample relative to the reference sample predicts the occurrence of metastatic disease.

5. A method of monitoring metastatic disease treatment in a subject comprising:

obtaining a first and then a second sample of isolated exosomes, at different points in time, from the subject being treated for a metastatic disease;

contacting the isolated exosomes in the first and second samples with two or more antibodies selected from the group consisting of an anti-MET antibody, an anti-TYRP2 antibody, an anti-VLA-4 antibody, an anti-Hsp-90 antibody, and an anti-Hsp-70 antibody, wherein said antibodies bind to their respective target protein, if expressed by isolated exosomes of the first and second samples, to form two or more different antibody-target protein complexes;

detecting the two or more different antibody-target protein complexes formed as a result of said contacting in each of the first and second samples of isolated exosomes:

quantifying the amount of the two or more different antibody-target protein complexes formed based on said detecting in each of the first and second samples of isolated exosomes;

determining the difference between quantified amounts of the two or more different antibody-target protein complexes formed in the first sample of isolated exosomes and amounts of the corresponding two or more different antibody-target protein complexes formed in the second sample of isolated exosomes; and identifying whether the subject is responding to the metastatic disease treatment based on said determining, wherein a decrease in the quantified amounts of the two or more different antibody-target protein complexes formed in the second sample of isolated exosomes compared to the first sample of isolated exosomes indicates the subject is responding favorably to the metastatic disease treatment, and wherein no change in the quantified amounts of the two or more different antibody-target protein complexes formed in second sample of isolated exosomes compared to the first sample of isolated exosomes indicates the subject is not responding favorably to the metastatic disease treatment, said method further comprising modifying the course of treatment for the subject upon a determination that the subject is not responding favorably to the metastatic disease treatment.

6. The method according to claim 2, wherein the amounts of the two or more different antibody-target protein complexes in the reference exosome sample are the average amounts of the two or more different antibody-target protein complexes in two or more samples from healthy, cancer-free subjects.

7. The method according to claim 2, wherein the reference exosome sample is a sample obtained from the subject at an earlier time point.

8. The method according to claim 2, wherein said detecting is carried out by enzyme linked immunosorbent assay.

9. The method according to claim 3, wherein the number of cells positive for CD117 and MET expression but negative for CD45 expression in the reference cell sample is the average number of cells positive for CD117 and MET expression but negative for CD45 expression in two or more cell samples from healthy, cancer-free subjects.

10. The method according to claim 3, wherein the reference cell sample is a sample obtained from the subject at an earlier time point.

11. The method according to claim 3, wherein said detecting is carried out by flow cytometry analysis.

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial
<220> FEATURE:
<223> OTHER INFORMATION: Human Rab27a shRNA

<400> SEQUENCE: 1
cccagtgtac tttaccaata ta                                            22

<210> SEQ ID NO 2
<211> LENGTH: 22

```
<212> TYPE: DNA
<213> ORGANISM: Artificial
<220> FEATURE:
<223> OTHER INFORMATION: Human Rab27a shRNA

<400> SEQUENCE: 2
cagggaagac cagtgtactt ta                                            22

<210> SEQ ID NO 3
<211> LENGTH: 22
<212> TYPE: DNA
<213> ORGANISM: Artificial
<220> FEATURE:
<223> OTHER INFORMATION: Mouse Rab27a shRNA

<400> SEQUENCE: 3
acaggagagg tttcgtagct ta                                            22

<210> SEQ ID NO 4
<211> LENGTH: 22
<212> TYPE: DNA
<213> ORGANISM: Artificial
<220> FEATURE:
<223> OTHER INFORMATION: Scramble shRNA

<400> SEQUENCE: 4
atctcgcttg ggcgagagta ag                                            22

<210> SEQ ID NO 5
<211> LENGTH: 22
<212> TYPE: DNA
<213> ORGANISM: Artificial
<220> FEATURE:
<223> OTHER INFORMATION: Mouse MET shRNA

<400> SEQUENCE: 5
ccagactttt catacaagaa ta                                            22

<210> SEQ ID NO 6
<211> LENGTH: 22
<212> TYPE: DNA
<213> ORGANISM: Artificial
<220> FEATURE:
<223> OTHER INFORMATION: Mouse MET shRNA

<400> SEQUENCE: 6
ccctatgtag atcctgtaat aa                                            22
```